US008822451B2

United States Patent
Ruah et al.

(10) Patent No.: US 8,822,451 B2
(45) Date of Patent: Sep. 2, 2014

(54) MODULATORS OF ATP-BINDING CASSETTE TRANSPORTERS

(75) Inventors: Sara S. Hadida Ruah, La Jolla, CA (US); Anna R. Hazlewood, San Diego, CA (US); Peter D. J. Grootenhuis, San Diego, CA (US); Ashvani Kumar Singh, San Diego, CA (US); Thomas Cleveland, San Diego, CA (US); Frederick F. Van-Goor, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 1706 days.

(21) Appl. No.: 11/438,636

(22) Filed: May 22, 2006

(65) Prior Publication Data

US 2007/0105833 A1  May 10, 2007

Related U.S. Application Data

(60) Provisional application No. 60/683,982, filed on May 24, 2005.

(51) Int. Cl.
*C07D 239/42* (2006.01)
*C07D 403/04* (2006.01)
*A61K 31/505* (2006.01)

(52) U.S. Cl.
USPC ............... 514/217.06; 514/227.8; 514/235.8; 514/252.14; 514/275; 540/481; 540/601; 544/60; 544/122; 544/295; 544/331; 544/332

(58) Field of Classification Search
USPC ............ 544/60, 122, 295, 331, 332; 540/481, 540/601; 514/217.06, 227.8, 235.8, 252.14, 514/275
See application file for complete search history.

(56) References Cited

U.S. PATENT DOCUMENTS

2005/0113423 A1   5/2005  Vangoor et al.
2005/0282824 A1*  12/2005  Li .................................. 514/256

FOREIGN PATENT DOCUMENTS

| WO | 0064424 A2 | 11/2000 |
| WO | 0248148 A2 | 6/2002 |
| WO | 2004087679 A1 | 10/2004 |
| WO | 2005079800 A | 9/2005 |
| WO | WO 2005/079800 | * 9/2005 |

OTHER PUBLICATIONS

International Search Report mailed Jun. 5, 2007 for application No. PCT/US2006/019712.

* cited by examiner

*Primary Examiner* — Deepak Rao
(74) *Attorney, Agent, or Firm* — Nancy K. Brennan

(57) ABSTRACT

4-amido-pyrimidine compounds, derivatives and compositions thereof, and synthetic methods described herein are useful for modulating ATP-Binding Cassette ("ABC") transporters or fragments thereof, including Cystic Fibrosis Transmembrane Conductance Regulator ("CFTR"). The present invention also relates to methods of treating ABC transporter mediated diseases using such modulators.

23 Claims, No Drawings

MODULATORS OF ATP-BINDING CASSETTE TRANSPORTERS

CROSS-REFERENCE TO RELATED APPLICATIONS

This application claims the benefit under 35 U.S.C. §119 to U.S. Provisional application Ser. No. 60/683,982, filed May 24, 2005 and entitled "MODULATORS OF ATP-BINDING CASSETTE TRANSPORTERS". The entire contents of each of the above priority application are incorporated herein by reference.

FIELD OF THE INVENTION

The present invention relates to modulators of ATP-Binding Cassette ("ABC") transporters or fragments thereof, including Cystic Fibrosis Transmembrane Conductance Regulator ("CFTR"), compositions thereof, and methods therewith. The present invention also relates to methods of treating ABC transporter mediated diseases using such modulators.

BACKGROUND OF THE INVENTION

ABC transporters are a family of membrane transporter proteins that regulate the transport of a wide variety of pharmacological agents, potentially toxic drugs, and xenobiotics, as well as anions. ABC transporters are homologous membrane proteins that bind and use cellular adenosine triphosphate (ATP) for their specific activities. Some of these transporters were discovered as multi-drug resistance proteins (like the MDR1-P glycoprotein, or the multi-drug resistance protein, MRP1), defending malignant cancer cells against chemotherapeutic agents. To date, 48 ABC Transporters have been identified and grouped into 7 families based on their sequence identity and function.

ABC transporters regulate a variety of important physiological roles within the body and provide defense against harmful environmental compounds. Because of this, they represent important potential drug targets for the treatment of diseases associated with defects in the transporter, prevention of drug transport out of the target cell, and intervention in other diseases in which modulation of ABC transporter activity may be beneficial.

One member of the ABC transporter family commonly associated with disease is the cAMP/ATP-mediated anion channel, CFTR. CFTR is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in Cystic Fibrosis ("CF"), the most common fatal genetic disease in humans. Cystic Fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, more than 1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ☐F508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$— ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the Na⁺—K⁺-ATPase pump and Cl— channels expressed on the basolateral surface of the cell. Secondary active transport of chloride from the luminal side leads to the accumulation of intracellular chloride, which can then passively leave the cell via Cl⁻ channels, resulting in a vectorial transport. Arrangement of Na⁺/2Cl⁻/K⁺ co-transporter, Na⁺—K⁺-ATPase pump and the basolateral membrane K⁺ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to Cystic Fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome.

COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as Cystic Fibrosis and Sjögren's syndrome. Increasing anion secretion via CFTR would enhance fluid transport from the comeal endothelial cells and secretory glands surrounding the eye to increase comeal hydration. This would help to alleviate the symptoms associated with dry eye disease. Sjögren's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. Infact, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. The diseases associated with the first class of ER malfunction are Cystic fibrosis (due to misfolded ☐F508-CFTR as discussed above), Hereditary emphysema (due to a1-antitrypsin; non Piz variants), Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses (due to Lysosomal processing enzymes), Sandhof/Tay-Sachs (due to β-Hexosaminidase), Crigler-Najjar type II (due to UDP-glucuronyl-sialyc-transferase), Polyendocrinopathy/Hyperinsulemia, Diabetes mellitus (due to Insulin receptor), Laron dwarfism (due to Growth hormone receptor), Myleoperoxidase deficiency, Primary hypoparathyroidism (due to Preproparathyroid hormone), Melanoma (due to Tyrosinase). The diseases associated with the latter class of ER malfunction are Glycanosis CDG type 1, Hereditary emphysema (due to ☐1-Antitrypsin (PiZ variant), Congenital hyperthyroidism, Osteogenesis imperfecta (due to Type I, II, IV procollagen), Hereditary hypofibrinogenemia (due to Fibrinogen), ACT deficiency (due to α1-Antichymotrypsin), Diabetes insipidus (DI), Neurophyseal DI (due to Vasopvessin hormone/V2-receptor), Neprogenic DI (due to Aquaporin II), Charcot-Marie Tooth syndrome (due to Peripheral myelin protein 22), Perlizaeus-Merzbacher disease, neurodegenerative diseases such as Alzheimer's disease (due to βAPP and presenilins), Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease (due to lysosomal ☐-galactosidase A) and Straussler-Scheinker syndrome (due to Prp processing defect).

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). 16 million travelers to developing countries from industrialized nations every year develop diarrhea, with the severity and number of cases of diarrhea varying depending on the country and area of travel.

Diarrhea in barn animals and pets such as cows, pigs and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrheal causing bacteria is enterotoxogenic *E. coli* (ETEC) having the K99 pilus antigen. Common viral causes of diarrhea include rotavirus and coronavirus. Other infectious agents include cryptosporidium, giardia lamblia, and salmonella, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial organisms at one time. This dramatically increases the severity of the disease.

Accordingly, there is a need for modulators of an ABC transporter activity, and compositions thereof, that can be used to modulate the activity of the ABC transporter in the cell membrane of a mammal.

There is a need for methods of treating ABC transporter mediated diseases using such modulators of ABC transporter activity.

There is a need for methods of modulating an ABC transporter activity in an ex vivo cell membrane of a mammal.

There is a need for modulators of CFTR activity that can be used to modulate the activity of CFTR in the cell membrane of a mammal.

There is a need for methods of treating CFTR-mediated diseases using such modulators of CFTR activity.

There is a need for methods of modulating CFTR activity in an ex vivo cell membrane of a mammal.

SUMMARY OF THE INVENTION

It has now been found that compounds of this invention, and pharmaceutically acceptable compositions thereof, are useful as modulators of ABC transporter activity, such as CFTR activity. These compounds have the general formula I:

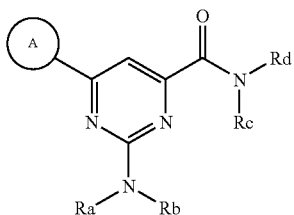

wherein ring A, and substituents Ra, Rb, Rc, and Rd are described below.

These compounds and pharmaceutically acceptable compositions are useful for treating or lessening the severity of a variety of diseases, disorders, or conditions, including, but not limited to, Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

DETAILED DESCRIPTION OF THE INVENTION

I. Definitions

As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

The term "modulating" as used herein means increasing or decreasing, e.g. activity, by a measurable amount. Compounds that modulate ABC Transporter activity, such as CFTR activity, by increasing the activity of the ABC Transporter, e.g., a CFTR anion channel, are called agonists. Compounds that modulate ABC Transporter activity, such as CFTR activity, by decreasing the activity of the ABC Transporter, e.g., CFTR anion channel, are called antagonists. An agonist interacts with an ABC Transporter, such as CFTR anion channel, to increase the ability of the receptor to transduce an intracellular signal in response to endogenous ligand binding. An antagonist interacts with an ABC Transporter, such as CFTR, and competes with the endogenous ligand(s) or substrate(s) for binding site(s) on the receptor to decrease the ability of the receptor to transduce an intracellular signal in response to endogenous ligand binding.

The phrase "treating or reducing the severity of an ABC Transporter mediated disease" refers both to treatments for diseases that are directly caused by ABC Transporter and/or CFTR activities and alleviation of symptoms of diseases not directly caused by ABC Transporter and/or CFTR anion channel activities. Examples of diseases whose symptoms may be affected by ABC Transporter and/or CFTR activity include, but are not limited to, Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B. and March, J., John Wiley & Sons, New York: 2001, the entire contents of which are hereby incorporated by reference.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-SO$_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-SO$_2$—, cycloaliphatic-SO$_2$—, or aryl-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-SO$_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-SO$_2$—, aliphaticamino-SO$_2$—, or cycloaliphatic-SO$_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refers to an amido group such as —N(R$^X$)—C(O)—R$^Y$ or —C(O)—N(R$^X$)$_2$, when used terminally, and —C(O)—N(R$^X$)— or —N(R$^X$)—C(O)— when used internally, wherein R$^X$ and R$^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen, alkyl, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—. R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic) carbonyl]; sulfonyl [e.g., aliphatic-$SO_2$— or amino-$SO_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl) carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl) aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy) alkyl)aryl; (((dialkyl)amino)alkyl)aryl; (nitroalkyl)aryl; (((alkylsulfonyl)amino)alkyl)aryl; ((heterocycloaliphatic) carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2] octyl, bicyclo[3.3.1]nonyl, bicyclo[3.3.2.]decyl, bicyclo[2.2.2]octyl, adamantyl, azacycloalkyl, or ((aminocarbonyl) cycloalkyl)cycloalkyl. A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl. A cycloalkyl or cycloalkenyl group can be optionally substituted with one or more substituents such as aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-$SO_2$— and aryl-$SO_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, "cyclic moiety" includes cycloaliphatic, heterocycloaliphatic, aryl, or heteroaryl, each of which has been defined previously.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b] thiopheneyl, 2-oxa-bicyclo[2.2.2]octyl, 1-aza-bicyclo[2.2.2]

octyl, 3-aza-bicyclo[3.2.1]octyl, anad 2,6-dioxa-tricyclo [3.3.1.0$^{3,7}$]nonyl. A monocyclic heterocycloalkyl group can be fused with a phenyl moiety such as tetrahydroisoquinoline. A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicycloheteroaliphatics are numbered according to standard chemical nomenclature.

A heterocycloalkyl or heterocycloalkenyl group can be optionally substituted with one or more substituents such as aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl,cinnolyl, phthalazyl, quinazolyl, quinoxalyl, isoquinolyl, 4H-quinolizyl, benzo-1, 2,5-thiadiazolyl, or 1,8-naphthyridyl.

Without limitation, monocyclic heteroaryls include furyl, thiophenyl, 2H-pyrrolyl, pyrrolyl, oxazolyl, thiazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfmyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl) amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaraliphatic (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$ wherein R$^X$ and R$^Y$ have been defined above and R$^Z$ can be aliphatic, aryl, araliphatic, heterocycloaliphatic, heteroaryl, or heteroaraliphatic.

As used herein, a "carboxy" group refers to —COOH, —COOR$^X$, —OC(O)H, —OC(O)R$^X$ when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplarly sulfinyl groups include aliphatic-S(O)—, aryl-S(O)—, (cycloaliphatic(aliphatic))—S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—R$^X$ or —SO—O—R$^X$, when used terminally and —O—S(O)— or —S(O)—O—when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, an "aminoalkyl" refers to the structure (R$^X$)$_2$N— alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N(R$^X$R$^Y$))N(R$^X$R$^Y$) or —NR$^X$—C(=NR$^X$)NR$^X$R$^Y$ wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent to at the end of the substituent bound to the rest of the chemical structure. Alkylcarboxy (e.g., alkyl-C(O)O— or alkyl-OC(O)—) and alkylcarboxyaryl (e.g., alkyl-C(O)O—aryl- or alkyl-O(CO)-aryl-) are examples of carboxy groups used internally.

As used herein, "cyclic group" includes mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-6. A branched aliphatic chain is a straight aliphatic chain that is substituted with one or more aliphatic groups. A branched aliphatic chain has the structure —[CHQ]$_v$— where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_2$, and $R_3$, and other variables contained therein formulae I encompass specific groups, such as alkyl and aryl. Unless otherwise noted, each of the specific groups for the variables Ra, Rb, Rc, Rd, and other variables contained therein can be optionally substituted with one or more substituents described herein. Each substituent of a specific group is further optionally substituted with one to three of halo, cyano, oxo, alkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkxoy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays.

II. Compounds

Compounds useful for modulating ABC Transporter and CFTR activity have the generic structure of formula I:

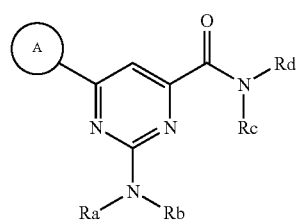

or a pharmaceutically acceptable salt thereof, wherein:

Each Ra is independently H, an optionally substituted aliphatic, an optionally substituted aryl, an optionally substituted aralkyl, an optionally substituted heteroaralkyl, an optionally substituted heteroaryl, an optionally substituted cycloaliphatic, or an optionally substituted cycloheteroaliphatic.

Each Rb is independently an optionally substituted aliphatic, an optionally substituted aryl, an optionally substituted aralkyl, an optionally substituted heteroaralkyl, an optionally substituted heteroaryl, an optionally substituted cycloaliphatic, an optionally substituted cycloheteroaliphatic,

in which w is 1, 2, 3, 4, or 5 and the phenyl is optionally substituted with 1-4 of Re, or Ra and Rb together with the nitrogen atom to which they are bound form an optionally substituted heterocycloaliphatic, an optionally substituted heteroaryl.

Each Rc is independently H, an optionally substituted heterocycloaliphatic, an optionally substituted cycloaliphatic, or an unsubstituted aliphatic.

Each Rd is independently H, an optionally substituted aliphatic, an optionally substituted aryl, an optionally substituted aralkyl, an optionally substituted heteroaralkyl, an optionally substituted heteroaryl, an optionally substituted cycloaliphatic, an optionally substituted cycloheteroaliphatic, or Rc and Rd together with the nitrogen atom to which they are bound form an optionally substituted heterocycloaliphatic.

Ring A is an aryl or heteroaryl, each optionally substituted with 1-4 Re.

Each Re is independently carboxy, amino, nitro, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, sulfonyl, sulfinyl, sulfanyl, sulfoxy, sulfamoyl, sulfamide, ketal, carbamoyl, cyano, halo, urea, thiourea, haloalkyl, or —Z—Rf, in which each alkyl, cycloalkyl, heterocycloalkyl, aryl, and heteroaryl portion of the Re substituents is optionally substituted with 1-3 of Rg, or two Re, on adjacent A ring atoms, together with the A ring atoms to which they are bound form a heterocycloaliphatic ring.

Each Z is absent, —O—, or —S—.

Each Rf is independently hydrogen, alkyl, carboxyalkyl, hydroxyalkyl, alkenyl, alkynyl, cycloalkyl, (cycloalkyl)alkyl, heterocycloalkyl, (heterocycloalkyl)alkyl, aryl, heteroaryl, aralkyl, heteroaralkyl, aroyl, heteroaroyl, alkoxycarbonyl, alkylcarbonyl, aminocarbonyl, or acyl, in which each alkyl, alkenyl, alkynyl, cycloalkyl, heterocycloalkyl, aryl, and heteroaryl portion of the Rf substituents is optionally substituted with 1-3 of Rg.

Each Rg is independently halo, cyano, alkoxy, hydroxyl, nitro, haloalkyl, and alkyl.

However, in several embodiments, ring A is not a 3,4,5-trimethoxyphenyl when Rd is an alkyl substituted with 4-methyl-1-piperazinyl; ring A is not 7-chloro-2-(4-fluorophenyl)pyrazolo[1,5-a]pyridine-3-yl or 7-cyclopentylamino-2-(4-fluorophenyl)pyrazolo[1,5-a]pyridine-3-yl; Rd is not {1-[(3,5-difluorophenyl)methyl)]-2-hydroxy-4-(1H-pyrazol-3-yl)butyl} when Rc is H, Ra and Rb are both alkyl, and Ring A is oxazolyl.

A subgeneric grouping of Compounds useful for modulating ABC Transporter and CFTR activity have the structure of formula II:

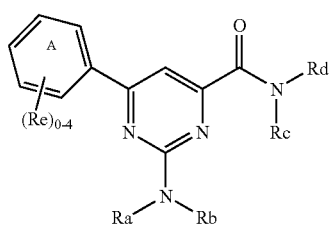

II wherein the variables Ra, Rb, Rc, Rd, and Re are defined above and with the proviso that Ring A is not a 3,4,5-trimethoxyphenyl when Rd is an alkyl substituted with 4-methyl-1-piperazinyl.

A further subgeneric grouping of Compounds useful for modulating ABC Transporter and CFTR activity have the structure of formula III:

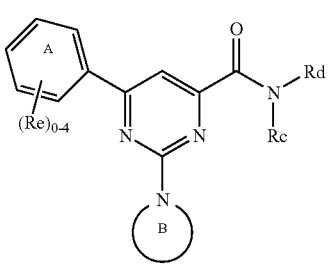

III wherein ring B is an optionally substituted heterocycloaliphatic and the variables Rc, Rd, and Re are defined above.

Embodiments of compounds of formula I, II, and III include the following aspects.

A. Ring A

Different aspects of Ring A include the following:

Ring A is aryl, such as phenyl. Ring A is bicyclic aryl, such as naphthyl, and azulenyl. In a specific aspect, Ring A is naphthyl. Embodiments of the aspects in which Ring A is aryl include the following. Ring A is an aryl optionally substituted with 1-4 of Re. Ring A is an aryl substituted with at least one Re substituent. Ring A is an aryl substituted with at least one Re substituent ortho or meta relative to the point of attachment between Ring A and the pyrimidine. Ring A is an aryl substituted with at least one Re substituent ortho, para, or meta relative to the point of attachment between Ring A and the pyrimidine. Ring A is an aryl substituted with at least one Re substituent ortho relative to the point of attachment between Ring A and the pyrimidine. Ring A is an aryl substituted with at least one Re substituent para relative to the point of attachment between Ring A and the pyrimidine. Ring A is an aryl substituted with at least one Re substituent meta relative to the point of attachment between Ring A and the pyrimidine. Ring A is an aryl including at least two Re substituents. Ring A is an aryl including at least two Re substituents one of which is ortho relative to the point of attachment between Ring A and the pyrimidine.

Ring A is heteroaryl. Ring A is a monocyclic heteroaryl, such as a pyrrolyl, furanyl, oxazolyl, thiazolyl, pyrazolyl, thiophenyl, pyridazinyl, pyrazinyl, pyrimidinyl, or pyridinyl. Ring A is thiophenyl, furanyl, pyrimidinyl, or pyridinyl. Ring A is thiophenyl. Ring A is a bicyclic heteroaryl, such as indolizinyl, indolyl, isoindolyl, indazolyl, benzimidazolyl, purinyl, isoquinolinyl, benzofuranyl, quinolinyl, benzothiophenyl, or benzodioxolanyl. Ring A is benzothiophenyl, benzodioxolanyl. Ring A is a heteroaryl optionally substituted with 1-4 of Re. Ring A is a heteroaryl substituted with at least one Re substituent. Ring A is an aryl substituted with at least one Re substituent ortho, para, or meta relative to the point of attachment between Ring A and the pyrimidine. Ring A is an aryl substituted with at least one Re substituent ortho relative to the point of attachment between Ring A and the pyrimidine. Ring A is an aryl substituted with at least one Re substituent para relative to the point of attachment between Ring A and the pyrimidine. Ring A is an aryl substituted with at least one Re substituent meta relative to the point of attachment between Ring A and the pyrimidine. Ring A is a heteroaryl including at least two Re substituents. Ring A is a heteroaryl including at least two Re substituents one of which is ortho relative to the point of attachment between Ring A and the pyrimidine.

B. Substituent Re

Different aspects of the Re substituents include the following:

The Re substituents, if present, are each independently carboxy, amino, nitro, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, sulfonyl, sulfinyl, sulfanyl, sulfoxy, sulfamoyl, sulfamide, ketal, or carbamoyl, cyano, halo, urea, thiourea, haloalkyl, in which each alkyl, cycloalkyl, heterocycloalkyl, aryl, and heteroaryl portion of the Re substituents is optionally substituted with 1-3 of halo, cyano, alkoxy, hydroxyl, nitro, haloalkyl, and alkyl.

The Re substituents, if present, are each independently carboxy, nitro, cyano, halo, haloalkyl, in which each alkyl, cycloalkyl, heterocycloalkyl, aryl, and heteroaryl portion of the Re substituents is optionally substituted with 1-3 of halo, cyano, alkoxy, hydroxyl, nitro, haloalkyl, and alkyl.

The Re substituents, if present, are each independently amino, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, urea, thiourea, in which each alkyl, cycloalkyl, heterocycloalkyl, aryl, and heteroaryl portion of the Re substituents is optionally substituted with 1-3 of halo, cyano, alkoxy, hydroxyl, nitro, haloalkyl, and alkyl.

The Re substituents, if present, are each independently alkylsulfanyl, sulfoxy, sulfamoyl, sulfamide, ketal, or carbamoyl, in which each alkyl, cycloalkyl, heterocycloalkyl, aryl, and heteroaryl portion of the Re substituents is optionally substituted with 1-3 of halo, cyano, alkoxy, hydroxyl, nitro, haloalkyl, and alkyl.

The Re substituents, if present, are independently —Z—Rf, in which each Z is absent, —O—, or —S—, and each Rf is independently hydrogen, alkyl, carboxyalkyl, hydroxyalkyl, alkenyl, alkynyl, cycloalkyl, (cycloalkyl)alkyl, heterocycloalkyl, (heterocycloalkyl)alkyl, aryl, heteroaryl, aralkyl, heteroaralkyl, aroyl, heteroaroyl, alkoxycarbonyl, alkylcarbonyl, aminocarbonyl, or acyl, in which each alkyl, alkenyl, alkynyl, cycloalkyl, heterocycloalkyl, aryl, and heteroaryl portion of the Rf substituents is optionally substituted with 1-3 of halo, cyano, alkoxy, hydroxyl, nitro, haloalkyl, and alkyl.

The Re substituents, if present, are independently —Z—Rf, in which Z is absent and each Rf is independently hydrogen, alkyl, carboxyalkyl, hydroxyalkyl, alkenyl, alkynyl, (cycloalkyl)alkyl, (heterocycloalkyl)alkyl, aralkyl, heteroaralkyl, aroyl, heteroaroyl, in which each alkyl, alkenyl, alkynyl, cycloalkyl, heterocycloalkyl, aryl, and heteroaryl portion of the Rf substituents is optionally substituted with 1-3 of halo, cyano, alkoxy, hydroxyl, nitro, haloalkyl, and alkyl.

The Re substituents, if present, are independently —Z—Rf, in which Z is absent and each Rf is independently cycloalkyl, heterocycloalkyl, aryl, heteroaryl, alkoxycarbonyl, alkylcarbonyl, aminocarbonyl, or acyl, in which each alkyl, alkenyl, alkynyl, cycloalkyl, heterocycloalkyl, aryl, and heteroaryl portion of the Rf substituents is optionally substituted with 1-3 of halo, cyano, alkoxy, hydroxyl, nitro, haloalkyl, and alkyl.

The Re substituents, if present, are independently alkyl, hydroxyalkyl, haloalkyl, haloalkoxy, alkoxy, halo, hydroxy, alkoxycarbonyl, alkylcarbonylamino, aryloxy, sulfoxy, carboxy, acyl, or alkylcarbonyl. The Ring A Re substituents are independently chloro, bromo, phenoxy, —CF$_3$, alkoxy (such as methoxy, ethoxy), —C(O)Oalkyl (such as —C(O)O—methyl, —C(O)O-ethyl, —C(O)O-propyl, and —C(O)O-isopropyl), alkyl (such as methyl, ethyl, propyl, butyl, and isopropyl), haloalkoxy (such as CF$_3$O—), hydroxylalkyl (such as HO-methyl-, HO-ethyl-, and HO-propyl), alkylcarbonylamino (such as methyl-C(O)—NH—, ethyl-C(O)—NH—, propyl-C(O)—NH—, and isopropyl-C(O)—NH—), —S(O)$_2$alkyl (such as —S(O)$_2$methyl, —S(O)$_2$ethyl, —S(O)$_2$butyl, and —S(O)$_2$propyl), and —S(O)$_2$aryl.

Two Re substituents, if present on adjacent A ring atoms, together with the ring atoms to which they are bound form a heterocycloaliphatic (such as a dioxolane ring).

C. Substituents Ra and Rb

Different aspects of Ra include the following:

Ra is hydroxyalkyl, alkyloxyalkyl, (heterocycloalkyl)alkyl, (cycloalkyl)alkyl, alkyloxycarbonylalkyl, aminoalkyl, carboxyalkyl, (cycloalkyloxy)alkyl, (heterocycloalkyloxy)alkyl, (aryloxy)alkyl, (heteroaryloxy)alkyl, (aralkyloxy)alkyl, (heteroarylalkoxy)alkyl, (aminocarbonyl)alkyl, (alkylcarbonylamino)alkyl, (cycloalkylcarbonylamino)alkyl, (cycloalkyl-alkylcarbonylamino)alkyl, (arylcarbonylamino)alkyl, (aralkylcarbonylamino)alkyl, (heterocycloalkyl-carbonylamino)alkyl, (heterocycloalkyl-alkylcarbonylamino)alkyl, (heteroarylcarbonylamino)alkyl, (heteroaralkylcarbonylamino)alkyl, (urea)alkyl, (thiourea)alkyl, (sulfamoyl)alkyl, (sulfamide)alkyl, (alkoxycarbonyl)alkyl, or (alkylcarbonyloxy)alkyl.

Ra is H.

Ra is an optionally substituted aliphatic, such as an optionally substituted alkyl, an optionally substituted alkenyl, or an optionally substituted alkynyl. Ra is an optionally substituted alkenyl. Ra is an alkenyl. Ra is propenyl, butenyl, or pentenyl. Ra is an alkenyl substituted with one or more of hydroxyl, amino, halo, cyano, oxo. Ra is an optionally substituted alkyl. Ra is an optionally substituted methyl, an optionally substituted ethyl, an optionally substituted propyl, an optionally substituted butyl, and optionally substituted pentyl. Ra is an alkyl substituted with one or more of hydroxyl, alkoxy, amino, halo, cyano, oxo. Ra is methyl substituted with one or more of hydroxyl, alkoxy, amino, halo, cyano, oxo. Ra is ethyl substituted with one or more of hydroxyl, alkoxy, amino, halo, cyano, oxo. Ra is propyl substituted with one or more of hydroxyl, alkoxy, amino, halo, cyano, oxo. Ra is butyl substituted with one or more of hydroxyl, alkoxy, amino, halo, cyano, oxo. Ra is a hydroxyl alkyl (such as HO-methyl, HO-ethyl, HO-butyl, and HO-propyl). Ra is an alkoxyalkyl (such as methoxymethyl-, methoxyethyl-, methyoxypropyl-, methyoxybutyl-, ethoxymethyl-, ethoxyethyl-, ethoxypropyl-, ethoxybutyl-, propoxymethyl-, propoxyethyl-, and propoxypropyl-. Ra is a cyanoalkyl (such as NC-methyl, NC-ethyl, NC-propyl, and NC-butyl). Ra is a carboxyalkyl (such as methyl-O(O)C-methyl-, methyl-O(O)C-ethyl-, methyl-O(O)C-propyl-, methyl-O(O)C-butyl-, ethyl-O(O)C-methyl-, ethyl-O(O)C-ethyl-, ethyl-O(O)C-propyl, ethyl-O(O)C-butyl, propyl-O(O)C-methyl-, propyl-O(O)C-ethyl, and propyl-O(O)C-propyl).

Ra is an optionally substituted aryl, an optionally substituted aralkyl, an optionally substituted heteroaralkyl, an optionally substituted heteroaryl, an optionally substituted cycloaliphatic, or an optionally substituted cycloheteroaliphatic. Ra is an optionally substituted aralkyl (such as an optionally substituted benzyl and an optionally substituted phenethyl). Ra is an optionally substituted heteroaralkyl (such as an optionally substituted furylmethyl, an optionally substituted pyridinylmethyl, and an optionally substituted pyridinylethyl).

Different aspects of Rb include the following.

Rb is an optionally substituted aliphatic such as an optionally substituted alkyl, and optionally substituted alkenyl, or an optionally substituted alkynyl. Rb is an optionally substituted alkenyl. Rb is an alkenyl. Rb is propenyl, butenyl, or pentenyl. Rb is an alkenyl substituted with one or more of hydroxyl, amino, halo, cyano, and oxo. Rb is an optionally substituted alkyl. Rb is an optionally substituted methyl, an optionally substituted ethyl, an optionally substituted propyl, an optionally substituted butyl, and optionally substituted pentyl. Rb is an alkyl substituted with one or more of hydroxyl, alkoxy, amino, halo, cyano, oxo. Rb is methyl substituted with one or more of hydroxyl, alkoxy, amino, halo, cyano, and oxo. Rb is ethyl substituted with one or more of hydroxyl, alkoxy, amino, halo, cyano, oxo. Rb is propyl substituted with one or more of hydroxyl, alkoxy, amino, halo, cyano, oxo. Rb is butyl substituted with one or more of hydroxyl, alkoxy, amino, halo, cyano, oxo. Rb is a hydroxyl alkyl (such as HO-methyl, HO-ethyl, HO-butyl, and HO-propyl). Rb is an alkoxyalkyl (such as methoxymethyl-, methoxyethyl-, methyoxypropyl-, methyoxybutyl-, ethoxymethyl-, ethoxyethyl-, ethoxypropyl-, ethoxybutyl-, propoxymethyl-, propoxyethyl-, and propoxypropyl-. Rb is cyanoalkyl (such as NC-methyl, NC-ethyl, NC-propyl, and NC-butyl). Rb is carboxyalkyl (such as methyl-O(O)C-methyl-, methyl-O(O)C-ethyl-, methyl-O(O)C-propyl-, methyl-O(O)C-butyl-, ethyl-O(O)C-methyl-, ethyl-O(O)C-ethyl-, ethyl-O(O)C-propyl, ethyl-O(O)C-butyl, propyl-O(O)C-methyl-, propyl-O(O)C-ethyl, and propyl-O(O)C-propyl).

Rb is an optionally substituted aryl, an optionally substituted aralkyl, an optionally substituted heteroaralkyl, an optionally substituted heteroaryl, an optionally substituted cycloaliphatic, or an optionally substituted cycloheteroaliphatic. Rb is an optionally substituted aralkyl (such as an optionally substituted benzyl and an optionally substituted phenethyl). Rb is an optionally substituted heteroaralkyl (such as an optionally substituted furylmethyl, an optionally substituted pyridinylmethyl, and an optionally substituted pyridinylethyl).

Rb is

in which w is 1, 2, 3, 4, or 5 and the phenyl is optionally substituted with 1-4 of Re. Rb is

in which w is 1 and the phenyl is optionally substituted with 1-4 of Re. Rb is

in which w is 3 and the phenyl is optionally substituted with 1-4 of Re.

Different aspects of Ra and Rb include the following.

Ra and Rb, together with the nitrogen atom to which they are bound, form an optionally substituted heterocycloaliphatic or an optionally substituted heteroaryl. Ra and Rb, together with the nitrogen atom to which they are bound, form an optionally substituted heterocycloaliphatic (such as an optionally substituted azacyclooctane, an optionally substituted azepinyl, an optionally substituted piperidine, an optionally substituted pyrrolidine, an optionally substituted tetrahydropyridine, an optionally substituted pyrroline, an optionally substituted piperazine, an optionally substituted azetidine, an optionally substituted morpholino, an optionally substituted thiomorpholino, an optionally substituted perhydroquinoline, an optionally substituted tetrahydroisoquinoline, and an optionally substituted thiapyrrolidine). Ra and Rb, together with the nitrogen atom to which they are bound, form an optionally substituted 8 membered heterocycloaliphatic. Ra and Rb, together with the nitrogen atom to which they are bound, form an optionally substituted 7 membered heterocycloaliphatic. Ra and Rb, together with the nitrogen atom to which they are bound, form an optionally substituted 6 membered heterocycloaliphatic. Ra and Rb, together with the nitrogen atom to which they are bound, form an optionally substituted 5 membered heterocycloaliphatic. Ra and Rb, together with the nitrogen atom to which they are bound, form a heterocycloaliphatic substituted with 1-3 of halo, haloalkyl, alkyl, alkyloxycarbonyl, alkylcarbonyl, aminocarbonyl, hydroxyalkyl, sulfoxy, sulfanyl, sulfonyl, sulfinyl, an optionally substituted aryl, an optionally substituted alkoxy, an optionally substituted aralkyl, an optionally aroyl, an optionally substituted heterocycloaliphatic, or an optionally substituted heteroaryl. Ra and Rb, together with the nitrogen atom to which they are bound, form a heterocycloaliphatic substituted with 1-3 of aryl (such as phenyl), acetyl, aralkyl (such as benzyl), hydroxyalkyl (such as HO-methyl and HO-ethyl), heterocycloaliphatic (such as dioxolanyl or 2-oxo-1,3-dihydrobenzoimidazol-1-yl), an optionally substituted heteroaryl (such as 2-oxo-benzimidazolyl), phenyl-C(O)—, 4-halo-phenyl-C(O)—, an optionally substituted phenyl (such as 4-cyanophenyl-, 4-hydroxyphenyl), and phenylS(O)$_2$—.

Ra and Rb, together with the nitrogen atom to which they are bound, form an optionally substituted heteroaryl (such as imidazoline, pyrrole, pyrazole, tetrahydroquinoline).

Ra and Rb are both optionally substituted aliphatic. Ra and Rb are both optionally substituted alkyl. Ra and Rb are both alkyl. Ra and Rb are both ethyl.

In some embodiments, both Ra and Rb are H.

D. Substituents Rc and Rd

Different aspects of Rd include the following.

Rd is H or an optionally substituted aliphatic. Rd is H. Rd is an optionally substituted alkyl (such as an optionally substituted methyl, an optionally substituted ethyl, an optionally substituted propyl, and an optionally substituted butyl). Rd is methyl, ethyl, propyl, isopropyl, or butyl.

Rd is an optionally substituted aralkyl (such as an optionally substituted benzyl and an optionally substituted phenethyl). Rd is an optionally substituted heteroaralkyl (such as an optionally substituted furylmethyl, an optionally substituted pyridinylmethyl, and an optionally substituted pyridinylethyl). Rd is an optionally substituted heteroaryl (such as an optionally substituted pyridinyl, an optionally substituted pyrrolyl, and an optionally substituted furyl). Rd is an optionally substituted aryl (such as an optionally substituted phenyl). Rd is an optionally substituted cycloaliphatic (such as an optionally substituted cyclopentyl and an optionally substituted cyclohexyl). Rd is an optionally substituted heterocycloaliphatic (such as an optionally substituted piperidine).

Different aspects of Rc include the following.

Rc is H. Rc is an optionally substituted heterocycloaliphatic (such as an optionally substituted piperidine). Rc is an optionally substituted cycloaliphatic (such as an optionally substituted cyclopentyl and an optionally substituted cyclohexyl). Rc is an unsubstituted aliphatic. Rc is an unsubstituted alkyl. Rc is methyl, ethyl, propyl, or butyl.

Different aspects of Rc and Rd include the following.

Rc and Rd together with the nitrogen atom to which they are bound form an optionally substituted heterocycloaliphatic. Rc and Rd together with the nitrogen atom to which they are bound form an optionally substituted pyrroline, pyrrolidine, imidazoline, imidazolidine, piperidine, piperazine, tertrahydropyridine, morpholine, and thiomorpholine.

Rc and Rd are both H.

Specific compounds useful for modulating ABC Transporter and/or CFTR activity are based upon generic formula I and subgeneric formulae II and III may include different combinations of each aspect and embodiment described above. For instance, specific compounds or subgeneric groupings of compounds may include different combinations of the aspects described above.

In certain embodiments, the compounds useful for modulating ABC Transporter and/or CFTR activity have the structure listed in Table 1.

TABLE 1

Specific Compounds

1
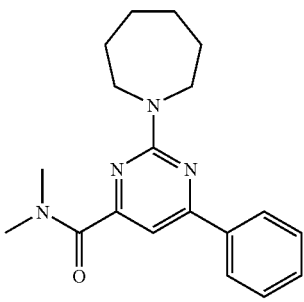 [SMILES: CN(C)C(=O)c1cc(-c2ccccc2)nc(N2CCCCCC2)n1]

2
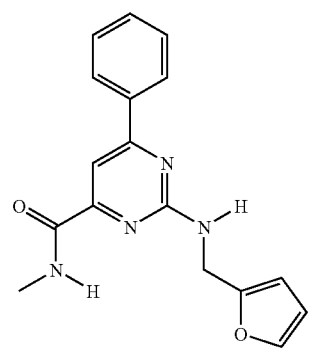 [SMILES: CNC(=O)c1cc(-c2ccccc2)nc(NCc2ccco2)n1]

3
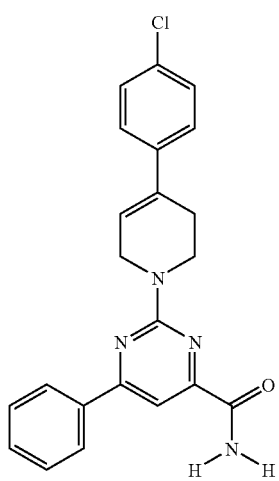 [SMILES: NC(=O)c1cc(-c2ccccc2)nc(N2CC=C(c3ccc(Cl)cc3)CC2)n1]

TABLE 1-continued

Specific Compounds

4
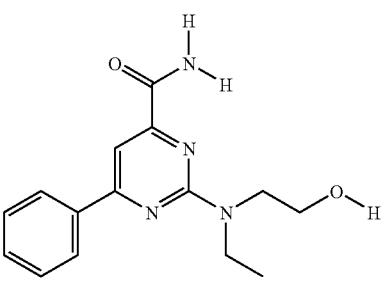 [SMILES: CCN(CCO)c1nc(C(N)=O)cc(-c2ccccc2)n1]

5
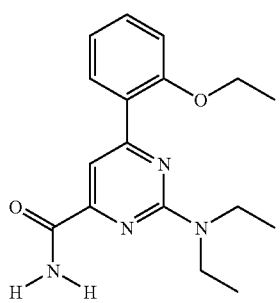 [SMILES: CCOc1ccccc1-c1cc(C(N)=O)nc(N(CC)CC)n1]

6
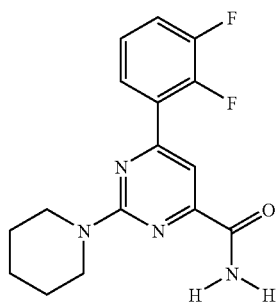 [SMILES: NC(=O)c1cc(-c2cccc(F)c2F)nc(N2CCCCC2)n1]

7
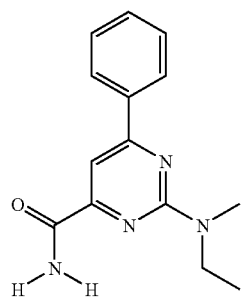 [SMILES: CCN(C)c1nc(C(N)=O)cc(-c2ccccc2)n1]

TABLE 1-continued
Specific Compounds
8
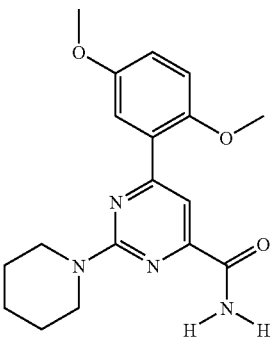 [SMILES: COc1ccc(OC)c(-c2cc(C(N)=O)nc(N3CCCCC3)n2)c1]
9
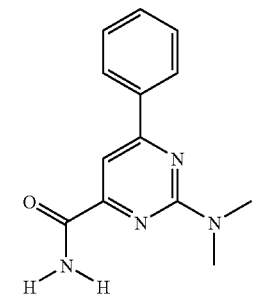 [SMILES: CN(C)c1nc(C(N)=O)cc(-c2ccccc2)n1]
10
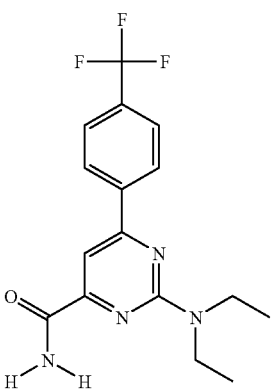 [SMILES: CCN(CC)c1nc(C(N)=O)cc(-c2ccc(C(F)(F)F)cc2)n1]
11
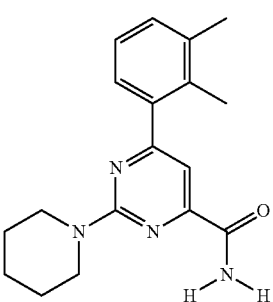 [SMILES: Cc1cccc(-c2cc(C(N)=O)nc(N3CCCCC3)n2)c1C]
TABLE 1-continued
Specific Compounds
12
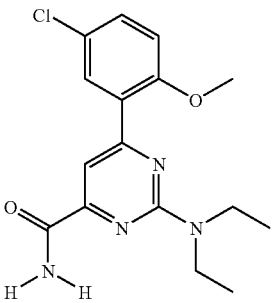
13
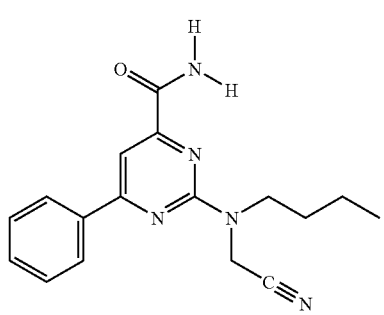 [SMILES: CCCCN(CC#N)c1nc(C(N)=O)cc(-c2ccccc2)n1]
14
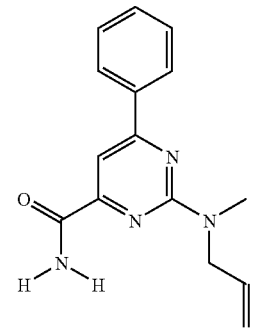 [SMILES: C=CCN(C)c1nc(C(N)=O)cc(-c2ccccc2)n1]
15
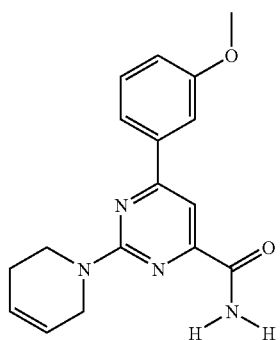 [SMILES: COc1cccc(-c2cc(C(N)=O)nc(N3CC=CCC3)n2)c1]

TABLE 1-continued
Specific Compounds
16
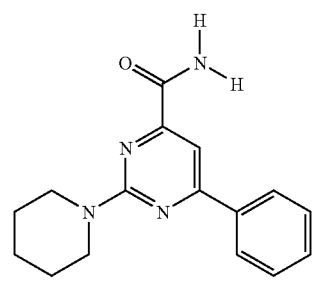 [SMILES: NC(=O)c1cc(-c2ccccc2)nc(N2CCCCC2)n1]
17
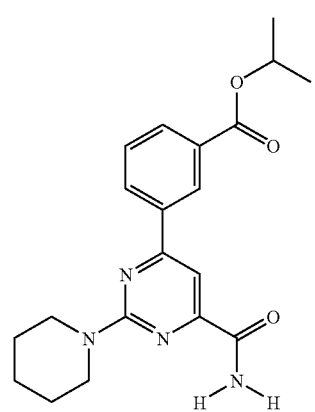 [SMILES: CC(C)OC(=O)c1cccc(-c2cc(C(N)=O)nc(N3CCCCC3)n2)c1]
18
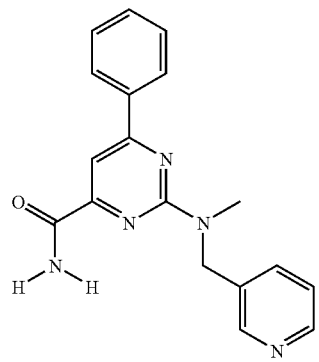 [SMILES: CN(Cc1cccnc1)c1nc(C(N)=O)cc(-c2ccccc2)n1]
19
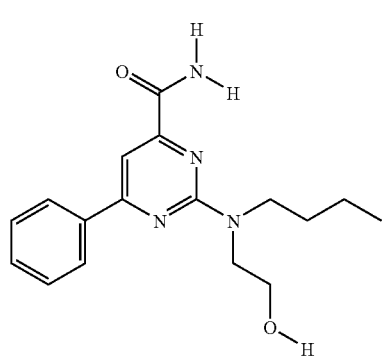 [SMILES: CCCCN(CCO)c1nc(C(N)=O)cc(-c2ccccc2)n1]
TABLE 1-continued
Specific Compounds
20
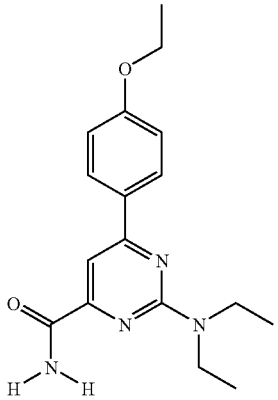 [SMILES: CCOc1ccc(-c2cc(C(N)=O)nc(N(CC)CC)n2)cc1]
21
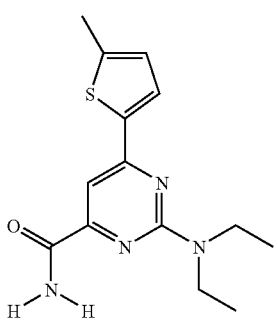 [SMILES: CCN(CC)c1nc(C(N)=O)cc(-c2ccc(C)s2)n1]
22
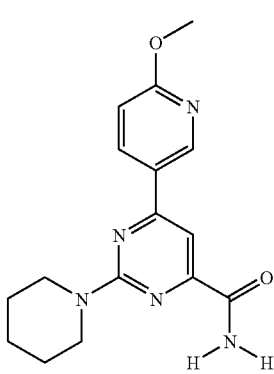 [SMILES: COc1ccc(-c2cc(C(N)=O)nc(N3CCCCC3)n2)cn1]
23
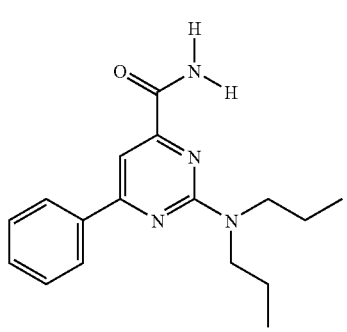 [SMILES: CCCN(CCC)c1nc(C(N)=O)cc(-c2ccccc2)n1]

TABLE 1-continued
Specific Compounds
24
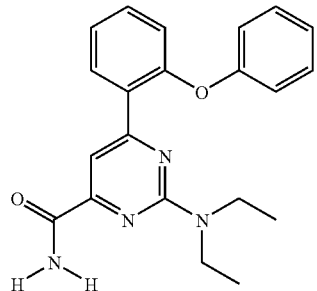 [SMILES: CCN(CC)c1nc(C(N)=O)cc(-c2ccccc2Oc2ccccc2)n1]
25
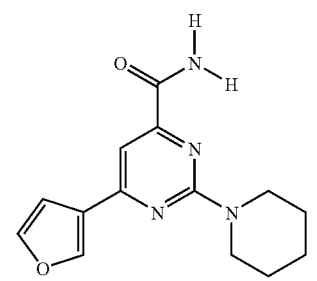 [SMILES: NC(=O)c1cc(-c2ccoc2)nc(N2CCCCC2)n1]
26
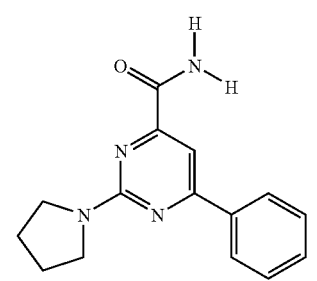 [SMILES: NC(=O)c1cc(-c2ccccc2)nc(N2CCCC2)n1]
27
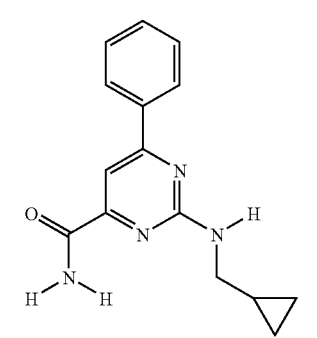 [SMILES: NC(=O)c1cc(-c2ccccc2)nc(NCC2CC2)n1]
TABLE 1-continued
Specific Compounds
28
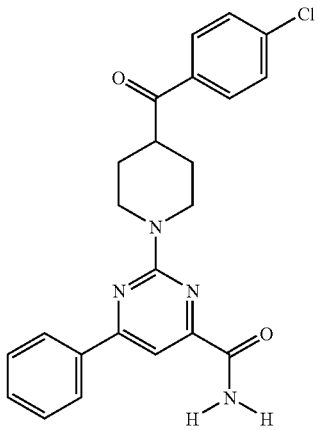 [SMILES: NC(=O)c1cc(-c2ccccc2)nc(N2CCC(C(=O)c3ccc(Cl)cc3)CC2)n1]
29
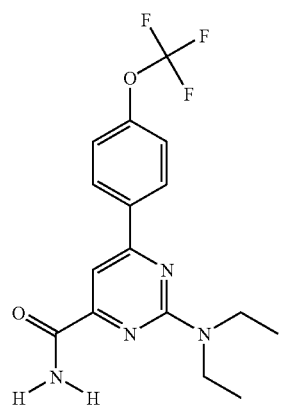 [SMILES: CCN(CC)c1nc(C(N)=O)cc(-c2ccc(OC(F)(F)F)cc2)n1]
30
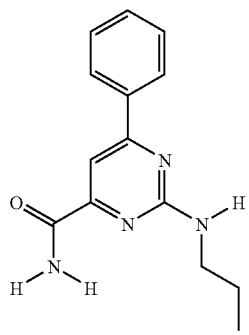 [SMILES: CCCNc1nc(C(N)=O)cc(-c2ccccc2)n1]
31
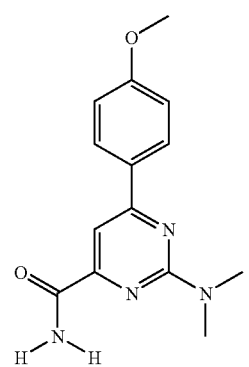 [SMILES: COc1ccc(-c2cc(C(N)=O)nc(N(C)C)n2)cc1]

TABLE 1-continued
Specific Compounds
32
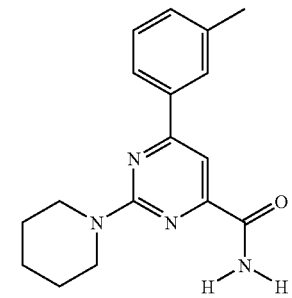 [SMILES: Cc1cccc(-c2cc(C(N)=O)nc(N3CCCCC3)n2)c1]
33
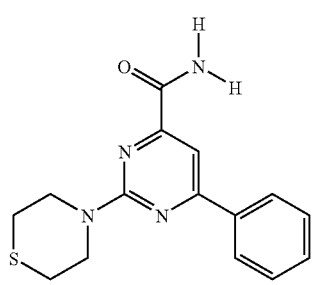 [SMILES: NC(=O)c1cc(-c2ccccc2)nc(N2CCSCC2)n1]
34
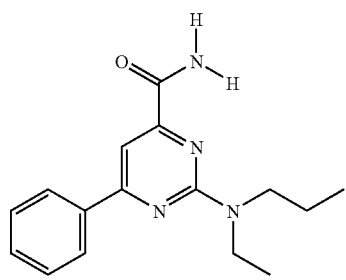 [SMILES: CCCN(CC)c1nc(C(N)=O)cc(-c2ccccc2)n1]
35
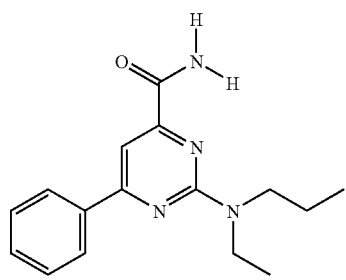 [SMILES: CCCN(CC)c1nc(C(N)=O)cc(-c2ccccc2)n1]
36
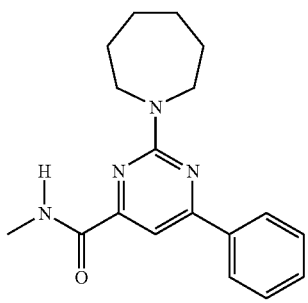 [SMILES: CNC(=O)c1cc(-c2ccccc2)nc(N2CCCCCC2)n1]
37
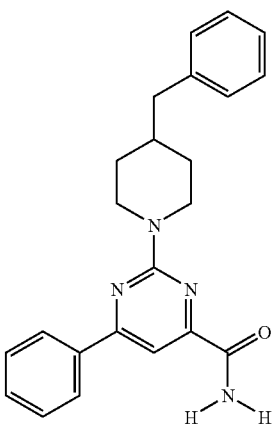 [SMILES: NC(=O)c1cc(-c2ccccc2)nc(N2CCC(Cc3ccccc3)CC2)n1]
38
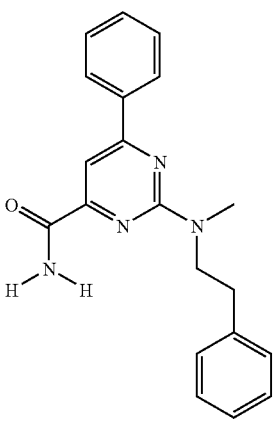 [SMILES: CN(CCc1ccccc1)c1nc(C(N)=O)cc(-c2ccccc2)n1]
39
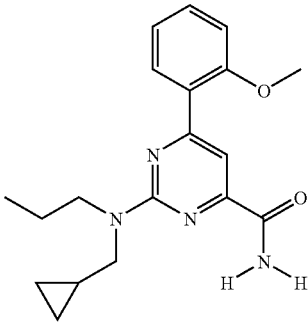 [SMILES: CCCN(CC1CC1)c1nc(C(N)=O)cc(-c2ccccc2OC)n1]

TABLE 1-continued
Specific Compounds
40
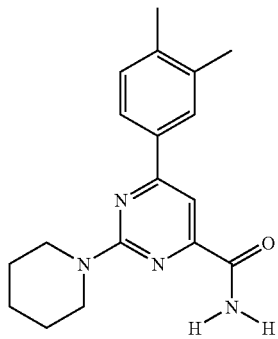 [SMILES: Cc1ccc(-c2cc(C(N)=O)nc(N3CCCCC3)n2)cc1C]
41
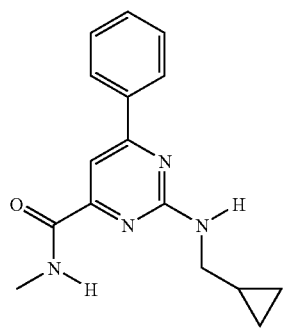 [SMILES: CNC(=O)c1cc(-c2ccccc2)nc(NCC2CC2)n1]
42
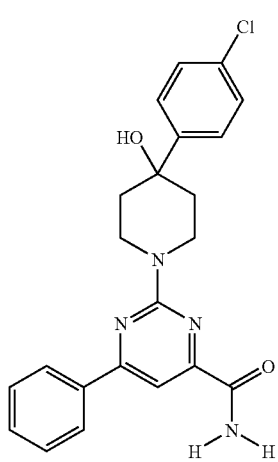 [SMILES: NC(=O)c1cc(-c2ccccc2)nc(N2CCC(O)(c3ccc(Cl)cc3)CC2)n1]
43
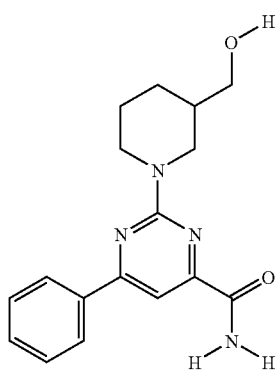 [SMILES: NC(=O)c1cc(-c2ccccc2)nc(N2CCCC(CO)C2)n1]
TABLE 1-continued
Specific Compounds
44
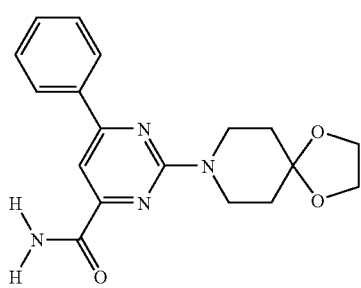 [SMILES: NC(=O)c1cc(-c2ccccc2)nc(N2CCC3(CC2)OCCO3)n1]
45
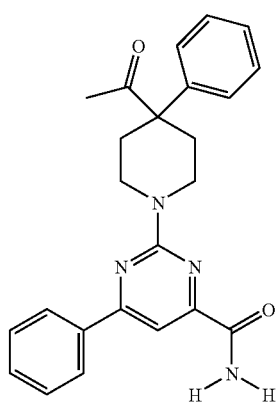 [SMILES: CC(=O)C1(c2ccccc2)CCN(c2nc(C(N)=O)cc(-c3ccccc3)n2)CC1]
46
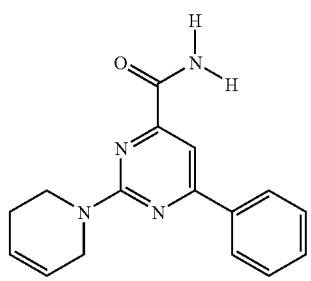 [SMILES: NC(=O)c1cc(-c2ccccc2)nc(N2CC=CCC2)n1]
47
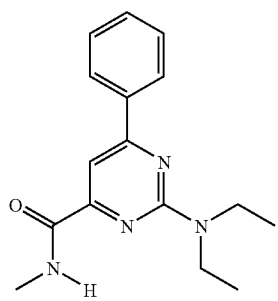

TABLE 1-continued
Specific Compounds
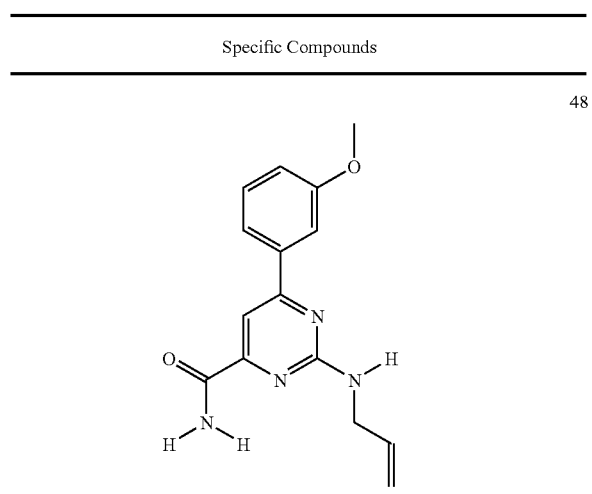
48
49
50
51
52
53
54
55
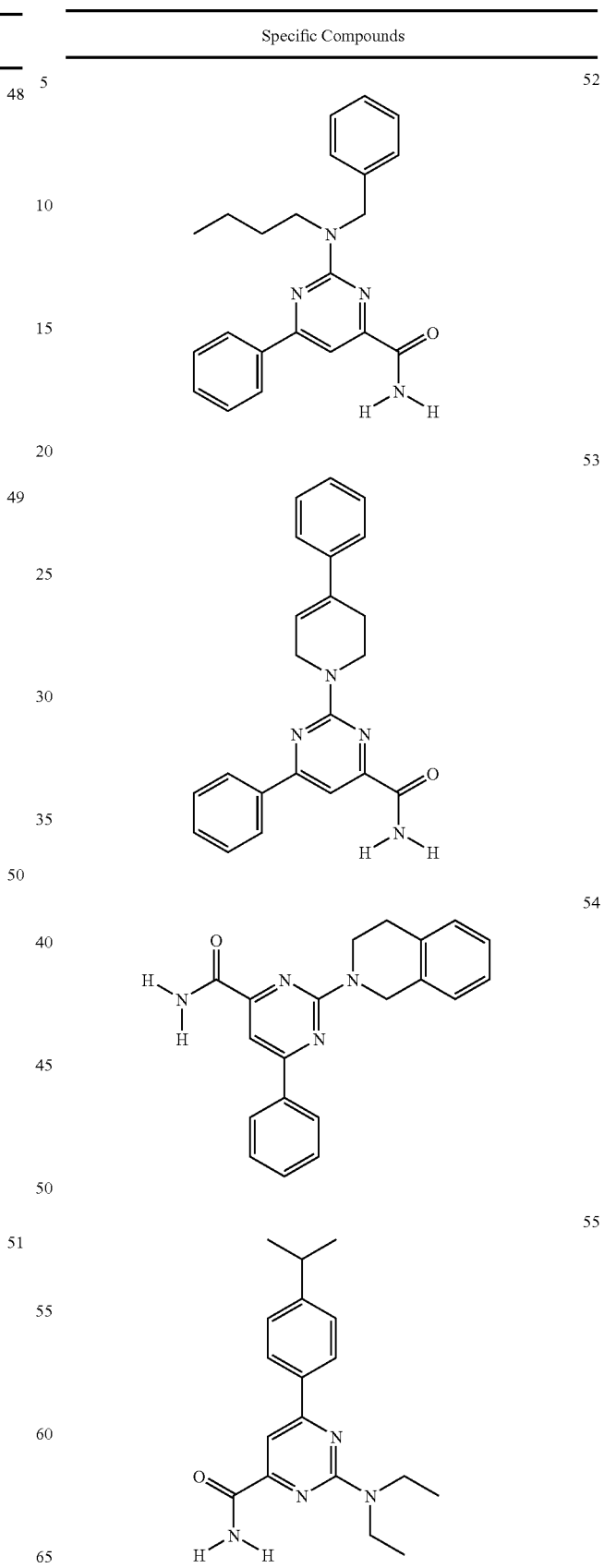

TABLE 1-continued
Specific Compounds
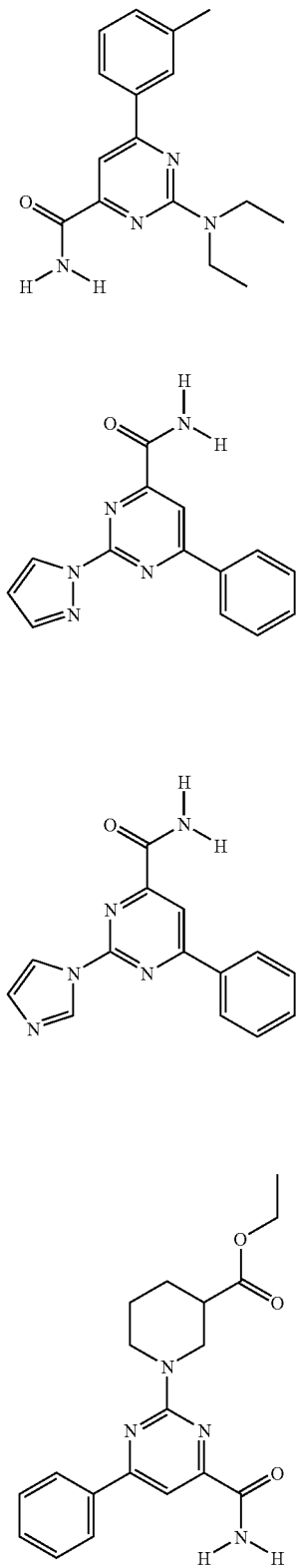
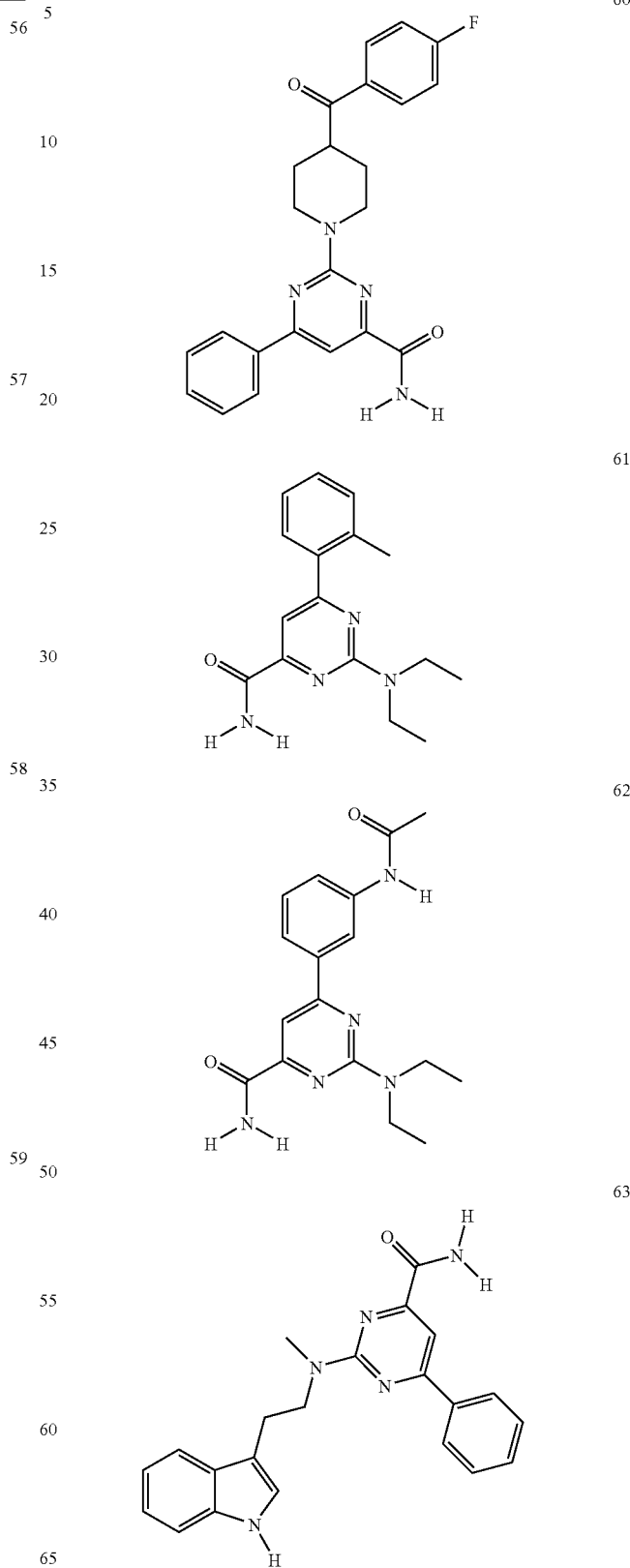

TABLE 1-continued
Specific Compounds
64
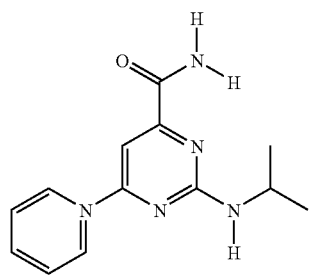
65
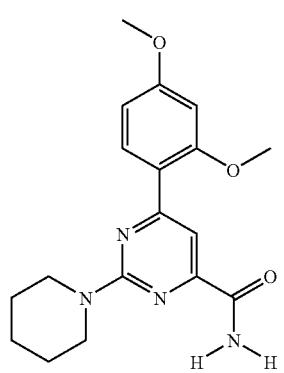 [SMILES: COc1ccc(-c2cc(C(N)=O)nc(N3CCCCC3)n2)c(OC)c1]
66
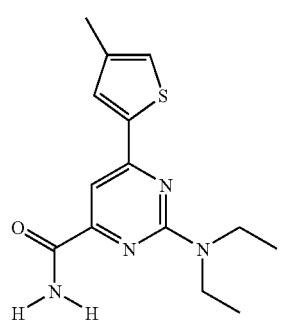 [SMILES: CCN(CC)c1nc(C(N)=O)cc(-c2cc(C)cs2)n1]
67
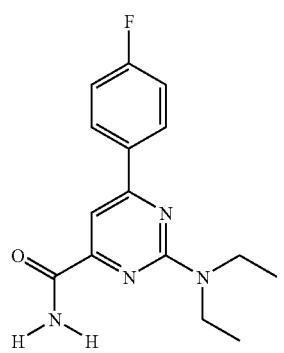 [SMILES: CCN(CC)c1nc(C(N)=O)cc(-c2ccc(F)cc2)n1]
TABLE 1-continued
Specific Compounds
68
69
70
71
72

TABLE 1-continued
Specific Compounds
73 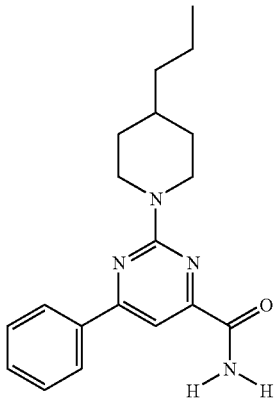 [SMILES: CCCC1CCN(c2nc(C(N)=O)cc(-c3ccccc3)n2)CC1]
74 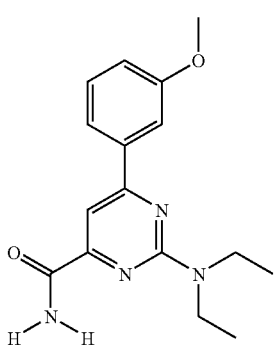 [SMILES: CCN(CC)c1nc(C(N)=O)cc(-c2cccc(OC)c2)n1]
75 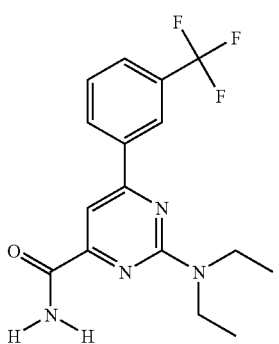 [SMILES: CCN(CC)c1nc(C(N)=O)cc(-c2cccc(C(F)(F)F)c2)n1]
76 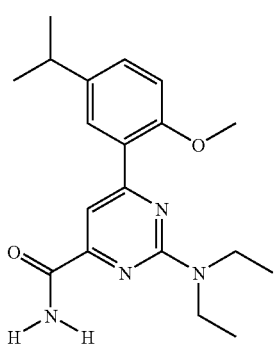 [SMILES: CCN(CC)c1nc(C(N)=O)cc(-c2cc(C(C)C)ccc2OC)n1]
TABLE 1-continued
Specific Compounds
77 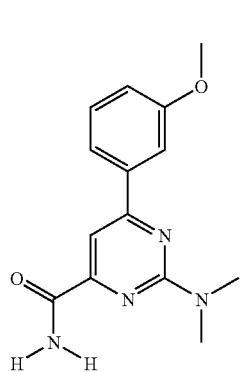 [SMILES: COc1cccc(-c2cc(C(N)=O)nc(N(C)C)n2)c1]
78 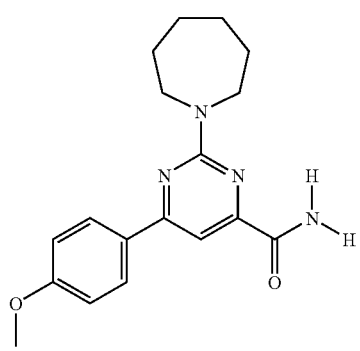 [SMILES: COc1ccc(-c2cc(C(N)=O)nc(N3CCCCCC3)n2)cc1]
79 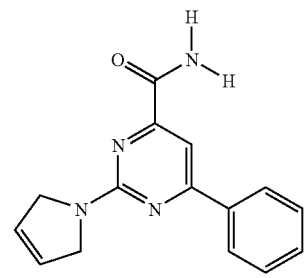 [SMILES: NC(=O)c1cc(-c2ccccc2)nc(N2CC=CC2)n1]
80 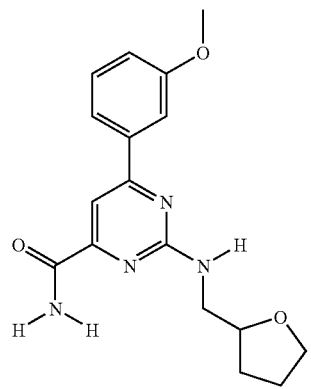 [SMILES: COc1cccc(-c2cc(C(N)=O)nc(NCC3CCCO3)n2)c1]

TABLE 1-continued
Specific Compounds
81
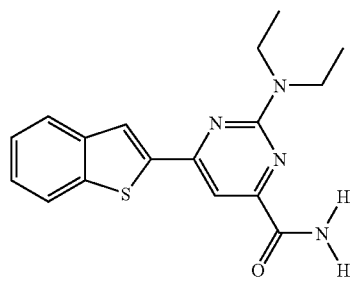 [SMILES: CCN(CC)c1nc(C(N)=O)cc(-c2cc3ccccc3s2)n1]
82
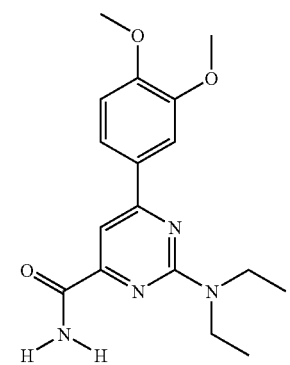 [SMILES: CCN(CC)c1nc(C(N)=O)cc(-c2ccc(OC)c(OC)c2)n1]
83
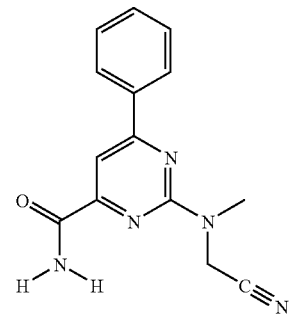 [SMILES: CN(CC#N)c1nc(C(N)=O)cc(-c2ccccc2)n1]
84
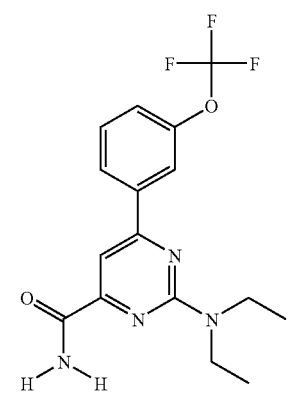 [SMILES: CCN(CC)c1nc(C(N)=O)cc(-c2cccc(OC(F)(F)F)c2)n1]
85
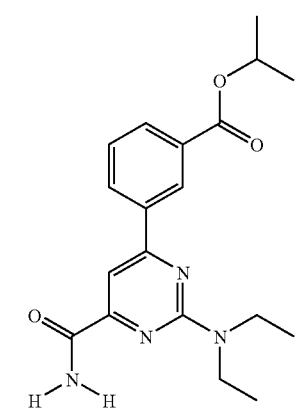 [SMILES: CCN(CC)c1nc(C(N)=O)cc(-c2cccc(C(=O)OC(C)C)c2)n1]
86
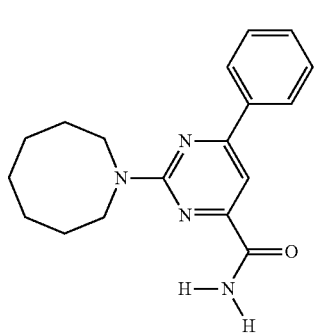 [SMILES: NC(=O)c1cc(-c2ccccc2)nc(N2CCCCCCC2)n1]
87
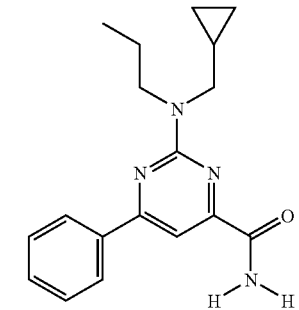 [SMILES: CCCN(CC1CC1)c1nc(C(N)=O)cc(-c2ccccc2)n1]
88

TABLE 1-continued

Specific Compounds

TABLE 1-continued
Specific Compounds
97
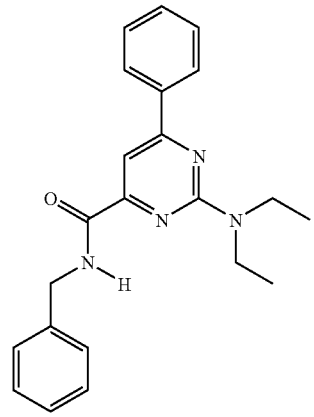 [SMILES: CCN(CC)c1nc(C(=O)NCc2ccccc2)cc(-c2ccccc2)n1]
98
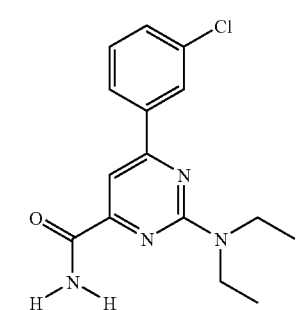 [SMILES: CCN(CC)c1nc(C(N)=O)cc(-c2cccc(Cl)c2)n1]
99
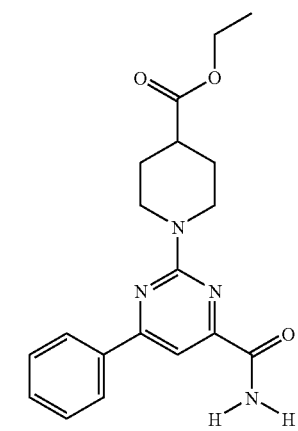 [SMILES: CCOC(=O)C1CCN(c2nc(C(N)=O)cc(-c3ccccc3)n2)CC1]
100
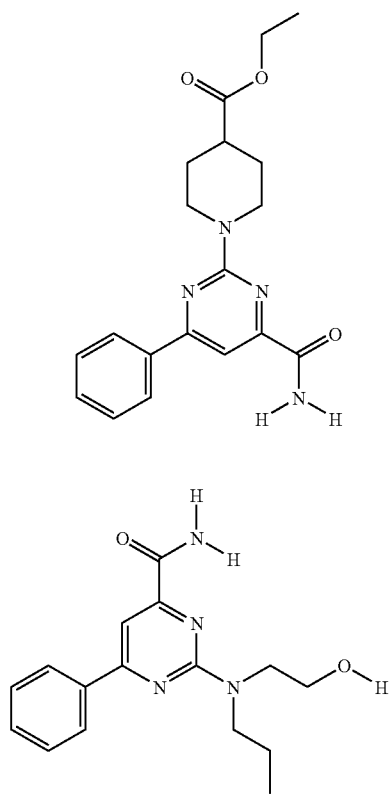
TABLE 1-continued
Specific Compounds
101
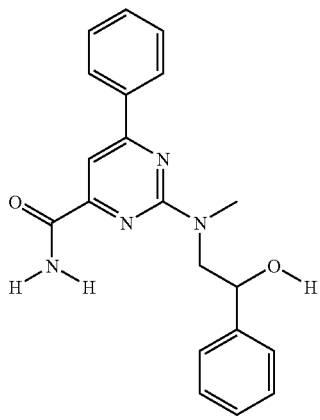 [SMILES: CN(CC(O)c1ccccc1)c1nc(C(N)=O)cc(-c2ccccc2)n1]
102
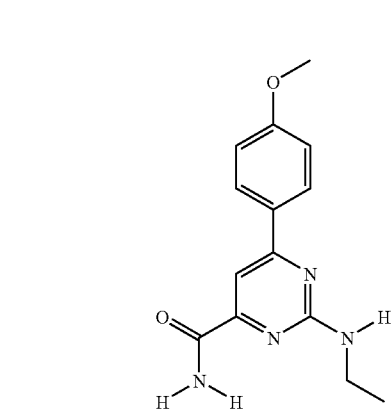 [SMILES: CCNc1nc(C(N)=O)cc(-c2ccc(OC)cc2)n1]
103
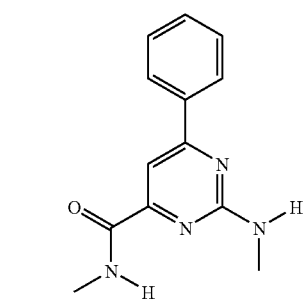 [SMILES: CNC(=O)c1cc(-c2ccccc2)nc(NC)n1]
104
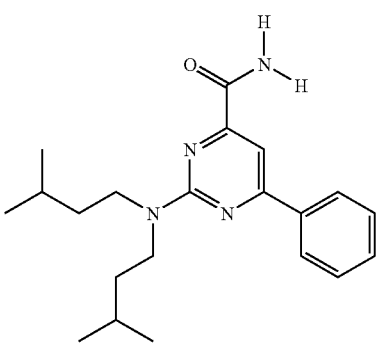 [SMILES: CC(C)CCN(CCC(C)C)c1nc(C(N)=O)cc(-c2ccccc2)n1]

TABLE 1-continued
Specific Compounds
105
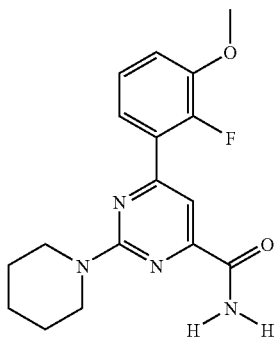 [SMILES: COc1cccc(-c2cc(C(N)=O)nc(N3CCCCC3)n2)c1F]
106
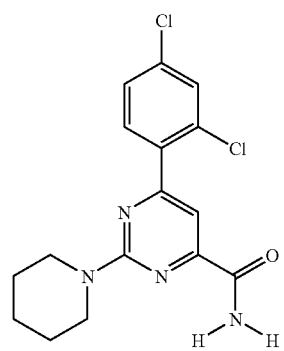 [SMILES: NC(=O)c1cc(-c2ccc(Cl)cc2Cl)nc(N2CCCCC2)n1]
107
108
TABLE 1-continued
Specific Compounds
109
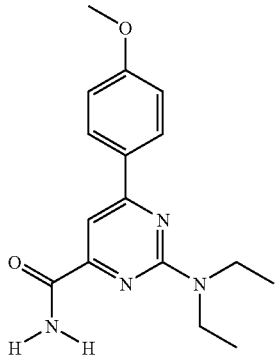 [SMILES: CCN(CC)c1nc(C(N)=O)cc(-c2ccc(OC)cc2)n1]
110
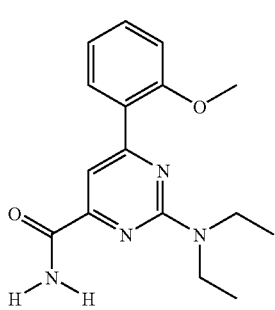 [SMILES: CCN(CC)c1nc(C(N)=O)cc(-c2ccccc2OC)n1]
111
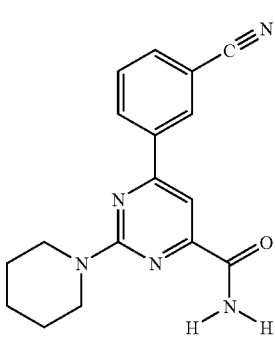 [SMILES: N#Cc1cccc(-c2cc(C(N)=O)nc(N3CCCCC3)n2)c1]
112
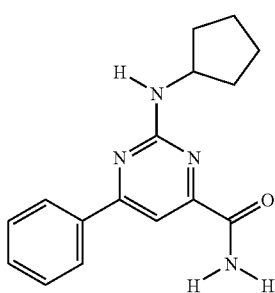 [SMILES: NC(=O)c1cc(-c2ccccc2)nc(NC2CCCC2)n1]

TABLE 1-continued
Specific Compounds
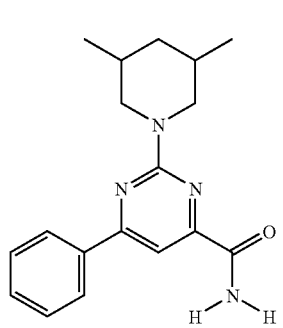 [SMILES: CC1CC(C)CN(c2nc(C(N)=O)cc(-c3ccccc3)n2)C1]
113
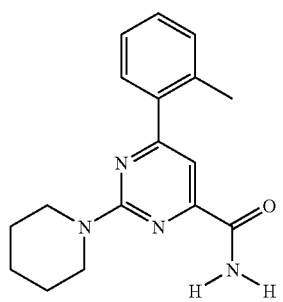 [SMILES: Cc1ccccc1-c1cc(C(N)=O)nc(N2CCCCC2)n1]
114
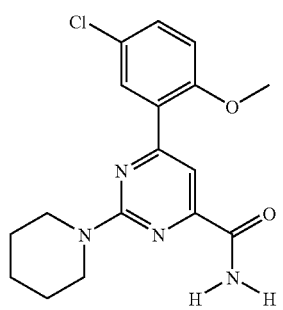
115
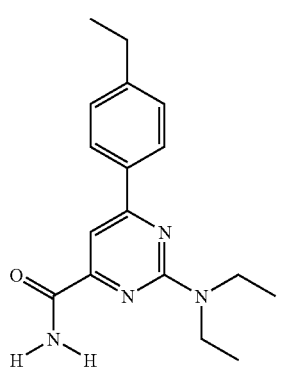 [SMILES: CCc1ccc(-c2cc(C(N)=O)nc(N(CC)CC)n2)cc1]
116
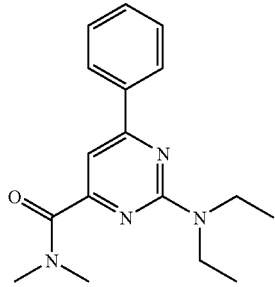 [SMILES: CCN(CC)c1nc(C(=O)N(C)C)cc(-c2ccccc2)n1]
117
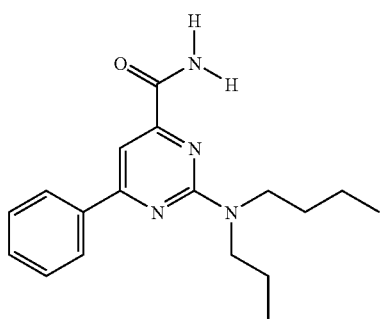 [SMILES: CCCCN(CCC)c1nc(C(N)=O)cc(-c2ccccc2)n1]
118
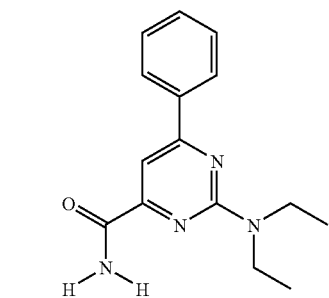 [SMILES: CCN(CC)c1nc(C(N)=O)cc(-c2ccccc2)n1]
119
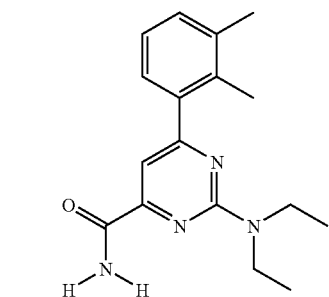 [SMILES: CCN(CC)c1nc(C(N)=O)cc(-c2cccc(C)c2C)n1]
120
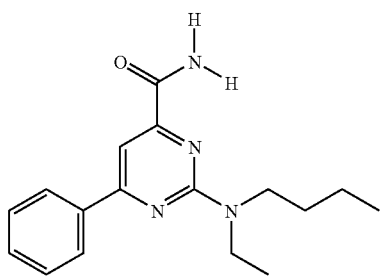 [SMILES: CCCCN(CC)c1nc(C(N)=O)cc(-c2ccccc2)n1]
121

TABLE 1-continued
Specific Compounds
122
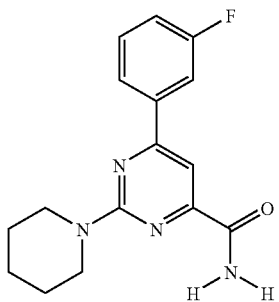 [SMILES: NC(=O)c1cc(-c2cccc(F)c2)nc(N2CCCCC2)n1]
123
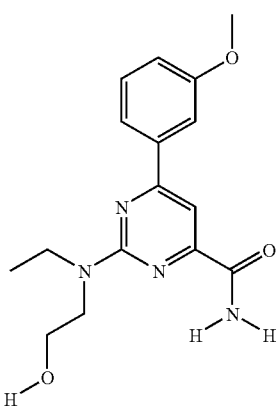 [SMILES: CCN(CCO)c1nc(C(N)=O)cc(-c2cccc(OC)c2)n1]
124
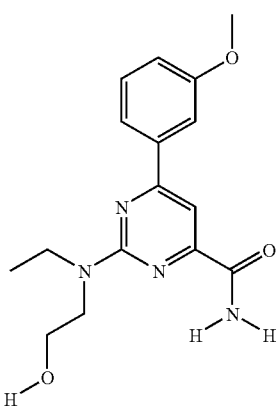 [SMILES: CCN(CCO)c1nc(C(N)=O)cc(-c2cccc(OC)c2)n1]
125
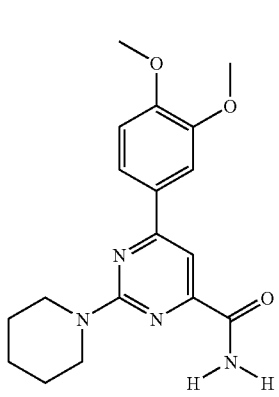 [SMILES: COc1ccc(-c2cc(C(N)=O)nc(N3CCCCC3)n2)cc1OC]
TABLE 1-continued
Specific Compounds
126
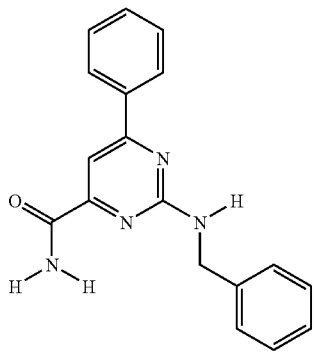 [SMILES: NC(=O)c1cc(-c2ccccc2)nc(NCc2ccccc2)n1]
127
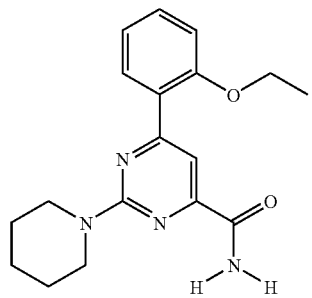 [SMILES: CCOc1ccccc1-c1cc(C(N)=O)nc(N2CCCCC2)n1]
128
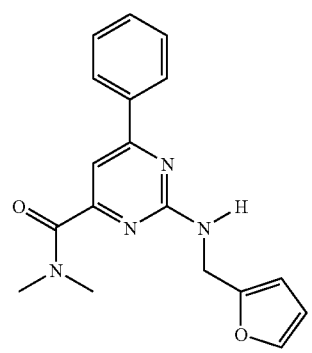 [SMILES: CN(C)C(=O)c1cc(-c2ccccc2)nc(NCc2ccco2)n1]
129
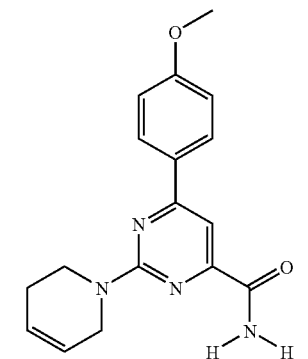 [SMILES: COc1ccc(-c2cc(C(N)=O)nc(N3CC=CCC3)n2)cc1]

TABLE 1-continued
Specific Compounds
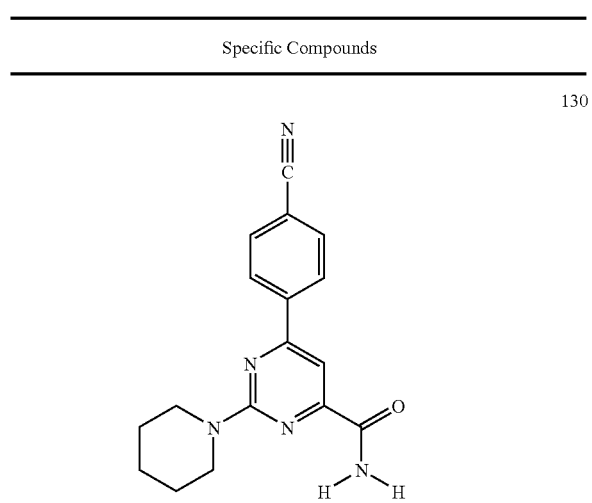
130
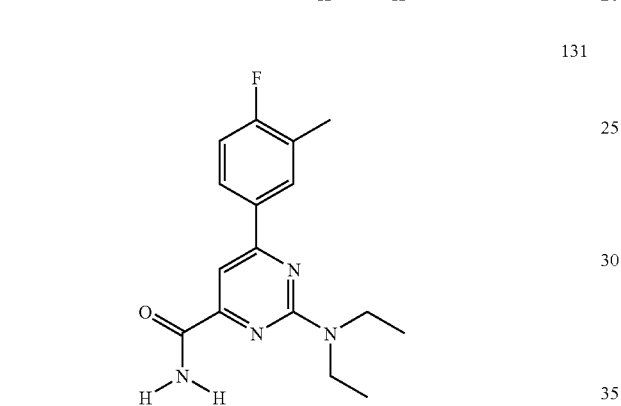
131
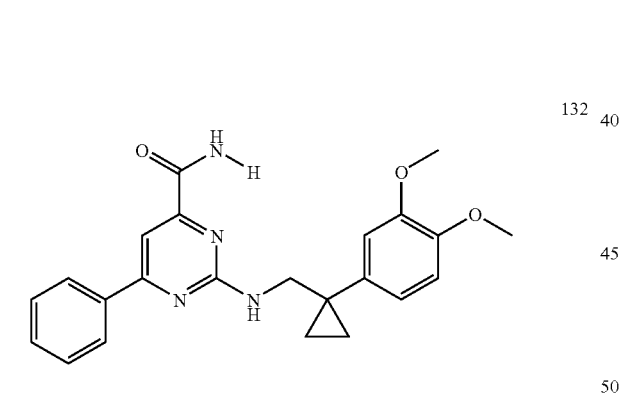
132
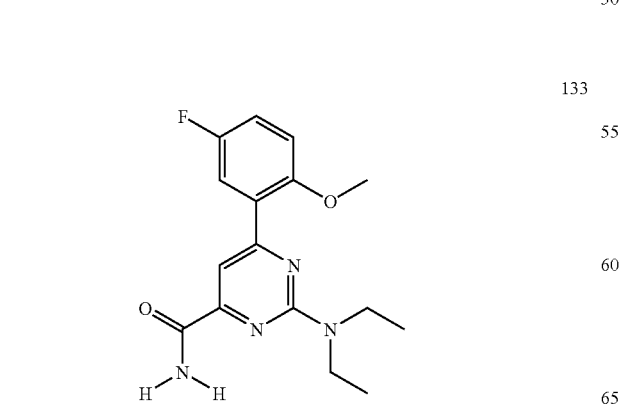
133
TABLE 1-continued
Specific Compounds
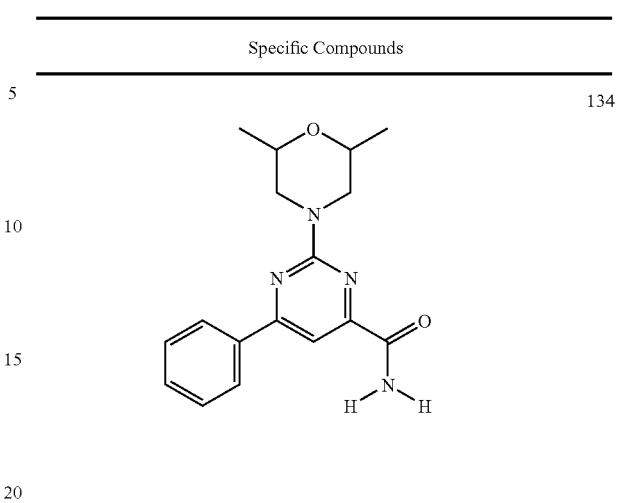
134
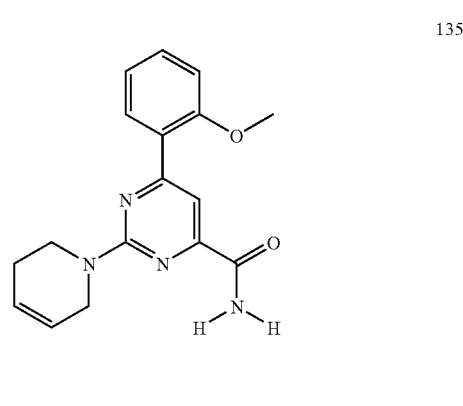
135
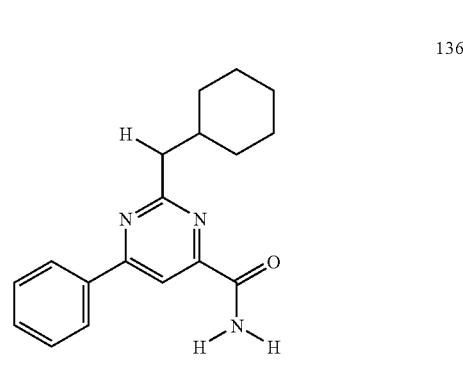
136
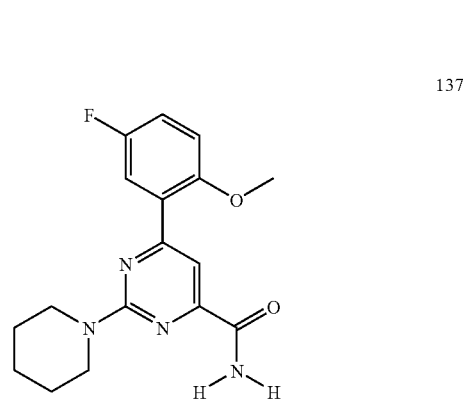
137

TABLE 1-continued
Specific Compounds
138 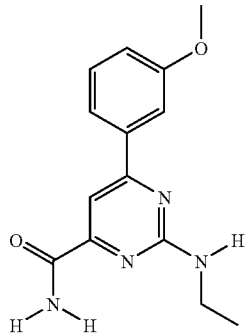 [SMILES: CCNc1nc(C(N)=O)cc(-c2cccc(OC)c2)n1]
139 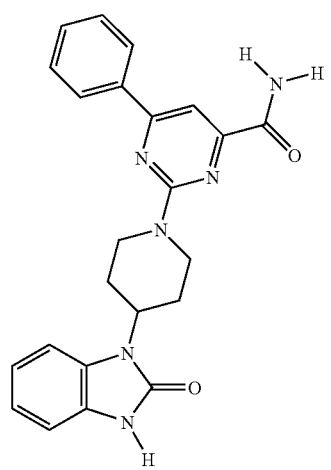 [SMILES: NC(=O)c1cc(-c2ccccc2)nc(N2CCC(n3c(=O)[nH]c4ccccc43)CC2)n1]
140 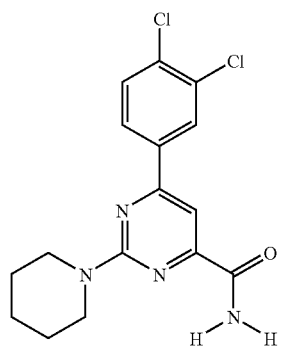 [SMILES: NC(=O)c1cc(-c2ccc(Cl)c(Cl)c2)nc(N2CCCCC2)n1]
141 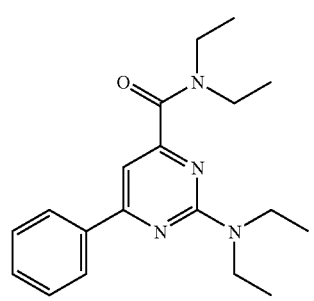 [SMILES: CCN(CC)C(=O)c1cc(-c2ccccc2)nc(N(CC)CC)n1]
TABLE 1-continued
Specific Compounds
142 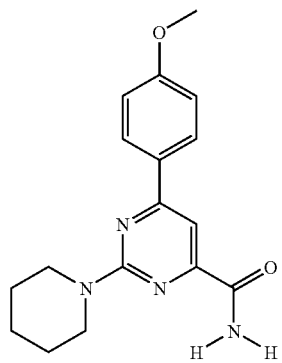
143 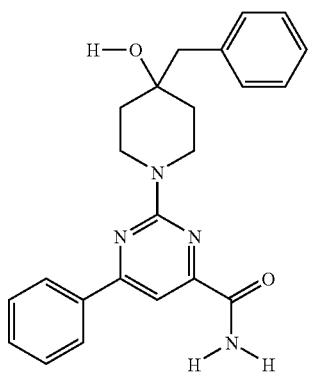 [SMILES: NC(=O)c1cc(-c2ccccc2)nc(N2CCC(O)(Cc3ccccc3)CC2)n1]
144 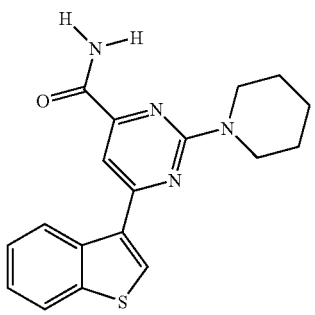 [SMILES: NC(=O)c1cc(-c2csc3ccccc23)nc(N2CCCCC2)n1]
145 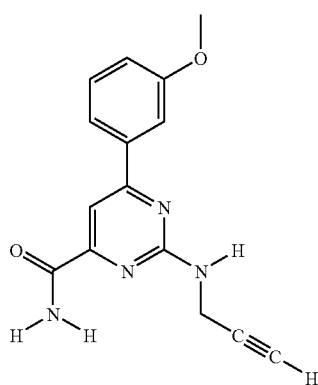 [SMILES: C#CCNc1nc(C(N)=O)cc(-c2cccc(OC)c2)n1]

TABLE 1-continued
Specific Compounds
146
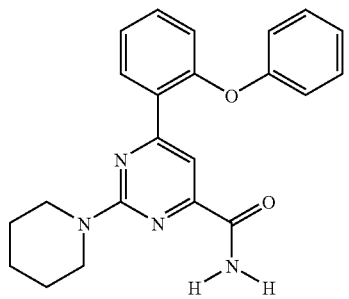 [SMILES: NC(=O)c1cc(-c2ccccc2Oc2ccccc2)nc(N2CCCCC2)n1]
147
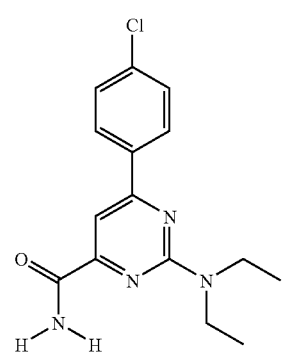 [SMILES: CCN(CC)c1nc(C(N)=O)cc(-c2ccc(Cl)cc2)n1]
148
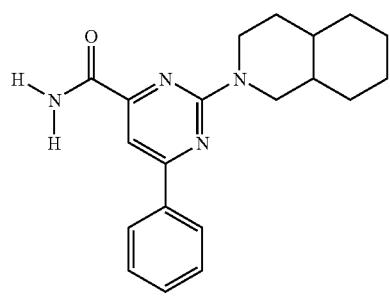 [SMILES: NC(=O)c1cc(-c2ccccc2)nc(N2CCC3CCCCC3C2)n1]
149
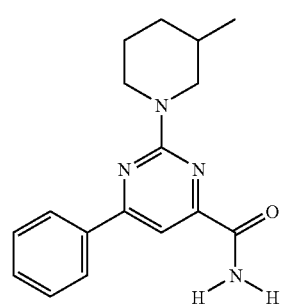 [SMILES: CC1CCCN(c2nc(C(N)=O)cc(-c3ccccc3)n2)C1]
TABLE 1-continued
Specific Compounds
150
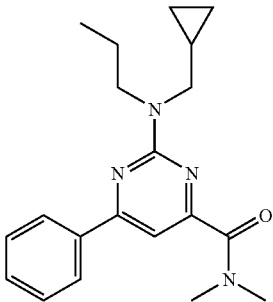 [SMILES: CCCN(CC1CC1)c1nc(C(=O)N(C)C)cc(-c2ccccc2)n1]
151
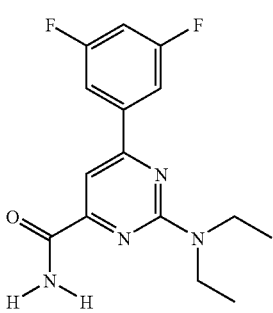 [SMILES: CCN(CC)c1nc(C(N)=O)cc(-c2cc(F)cc(F)c2)n1]
152
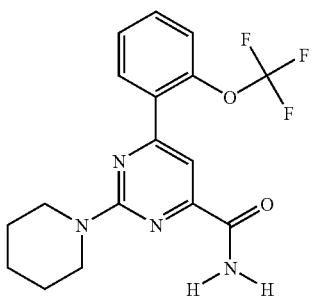 [SMILES: NC(=O)c1cc(-c2ccccc2OC(F)(F)F)nc(N2CCCCC2)n1]
153
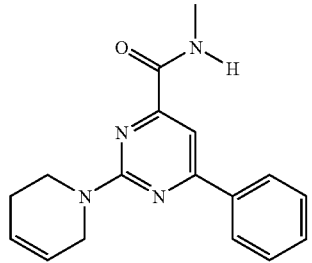 [SMILES: CNC(=O)c1cc(-c2ccccc2)nc(N2CC=CCC2)n1]
154
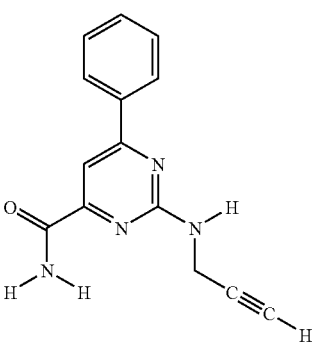 [SMILES: C#CCNc1nc(C(N)=O)cc(-c2ccccc2)n1]

TABLE 1-continued
Specific Compounds
155 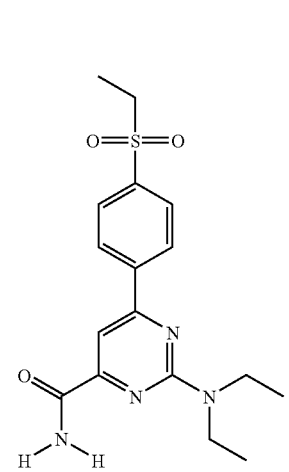 [SMILES: CCN(CC)c1nc(C(N)=O)cc(-c2ccc(S(=O)(=O)CC)cc2)n1]
156 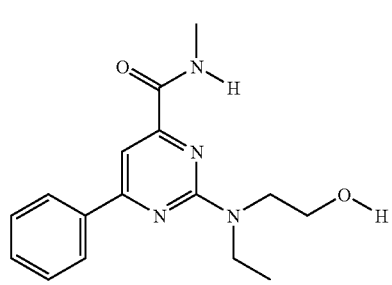 [SMILES: CCN(CCO)c1nc(C(=O)NC)cc(-c2ccccc2)n1]
157 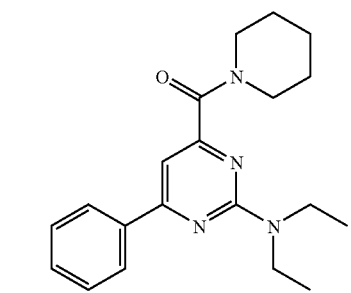 [SMILES: CCN(CC)c1nc(C(=O)N2CCCCC2)cc(-c2ccccc2)n1]
158 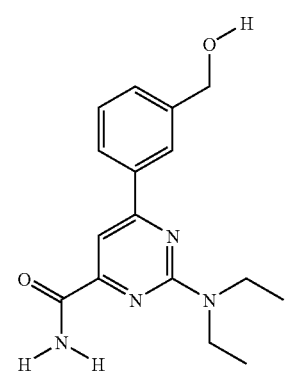 [SMILES: CCN(CC)c1nc(C(N)=O)cc(-c2cccc(CO)c2)n1]
TABLE 1-continued
Specific Compounds
159 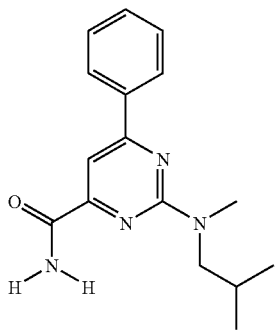 [SMILES: CC(C)CN(C)c1nc(C(N)=O)cc(-c2ccccc2)n1]
160 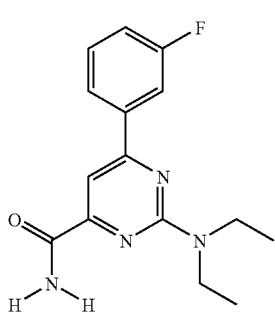 [SMILES: CCN(CC)c1nc(C(N)=O)cc(-c2cccc(F)c2)n1]
161 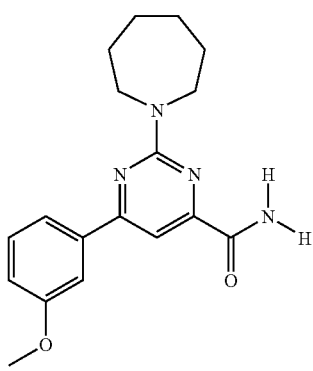 [SMILES: COc1cccc(-c2cc(C(N)=O)nc(N3CCCCCC3)n2)c1]
162 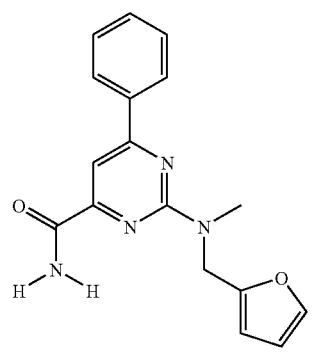 [SMILES: CN(Cc1ccco1)c1nc(C(N)=O)cc(-c2ccccc2)n1]

TABLE 1-continued
Specific Compounds
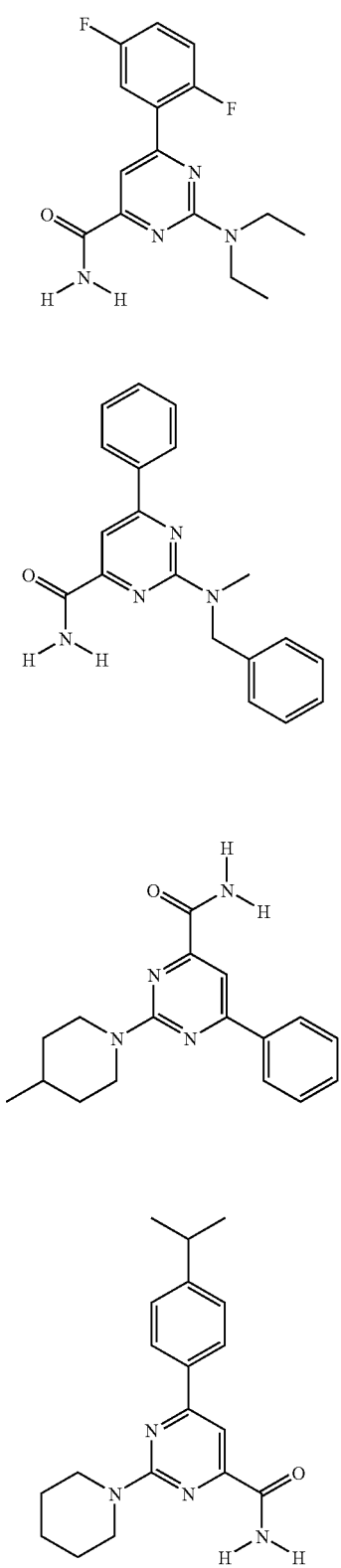
163
164
165
166
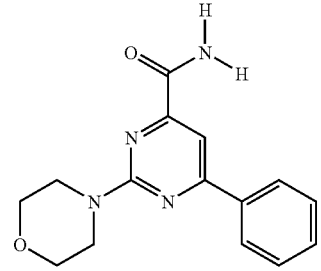 [SMILES: NC(=O)c1cc(-c2ccccc2)nc(N2CCOCC2)n1]
167
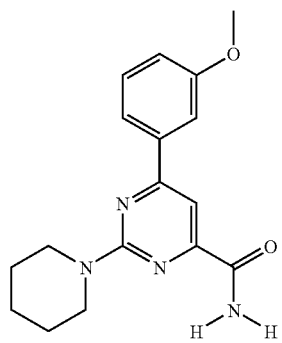
168
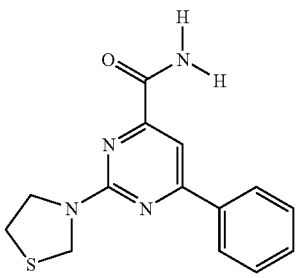
169
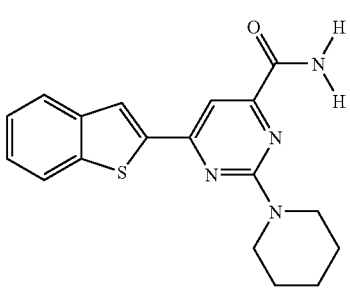 [SMILES: NC(=O)c1cc(-c2cc3ccccc3s2)nc(N2CCCCC2)n1]
170
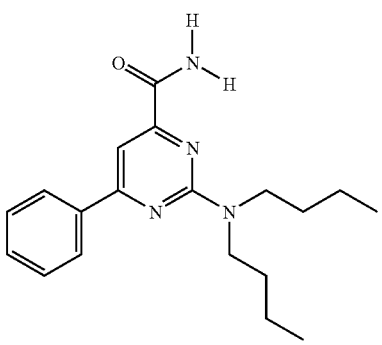 [SMILES: CCCCN(CCCC)c1nc(C(N)=O)cc(-c2ccccc2)n1]
171

TABLE 1-continued
Specific Compounds
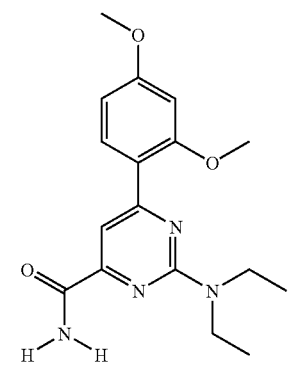 [SMILES: CCN(CC)c1nc(C(N)=O)cc(-c2ccc(OC)cc2OC)n1]
172
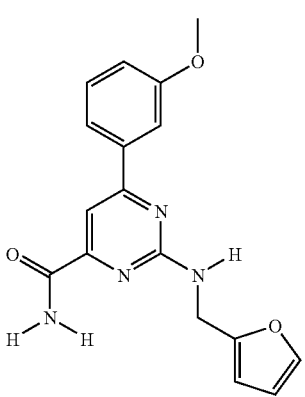 [SMILES: COc1cccc(-c2cc(C(N)=O)nc(NCc3ccco3)n2)c1]
173
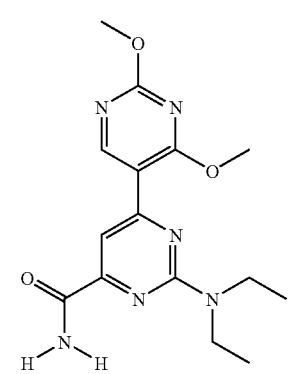 [SMILES: CCN(CC)c1nc(C(N)=O)cc(-c2cnc(OC)nc2OC)n1]
174
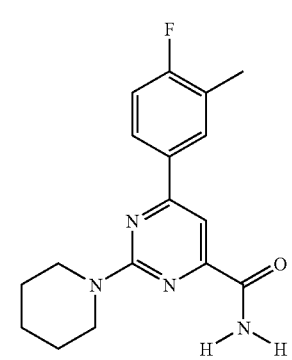 [SMILES: Cc1cc(-c2cc(C(N)=O)nc(N3CCCCC3)n2)ccc1F]
175
TABLE 1-continued
Specific Compounds
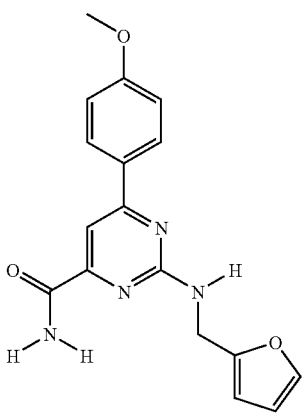 [SMILES: COc1ccc(-c2cc(C(N)=O)nc(NCc3ccco3)n2)cc1]
176
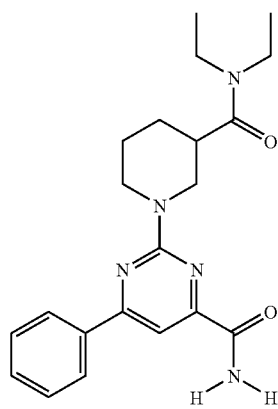 [SMILES: CCN(CC)C(=O)C1CCCN(c2nc(C(N)=O)cc(-c3ccccc3)n2)C1]
177
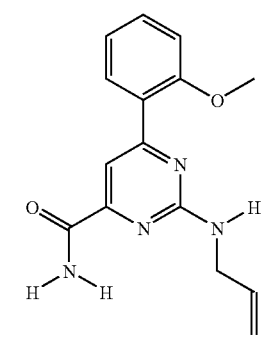 [SMILES: C=CCNc1nc(C(N)=O)cc(-c2ccccc2OC)n1]
178
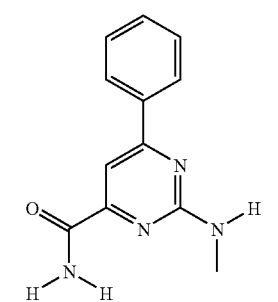
179

TABLE 1-continued
Specific Compounds
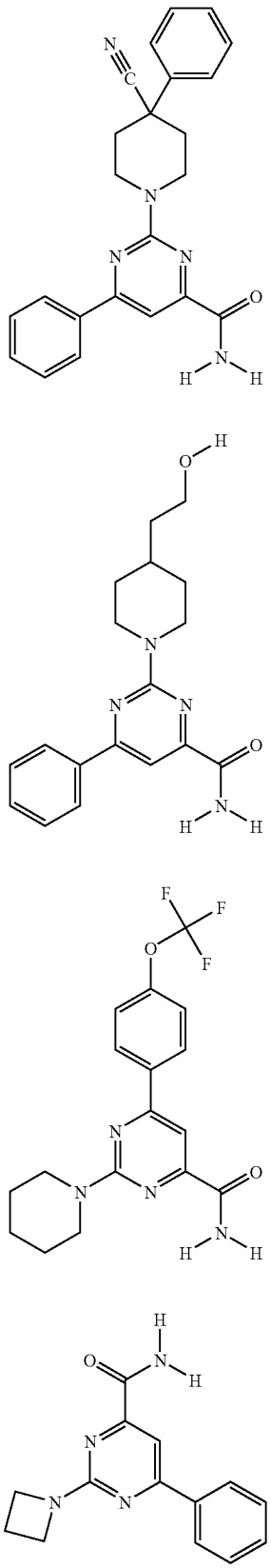
180
181
182
183
184
185
186
187

TABLE 1-continued
Specific Compounds
188
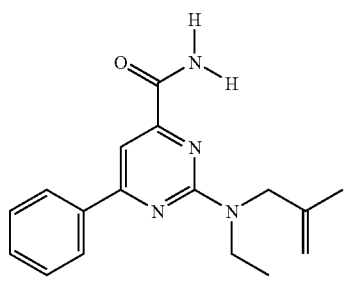 [SMILES: C=C(C)CN(CC)c1nc(C(N)=O)cc(-c2ccccc2)n1]
189
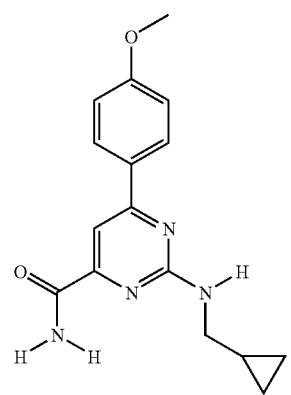 [SMILES: COc1ccc(-c2cc(C(N)=O)nc(NCC3CC3)n2)cc1]
190
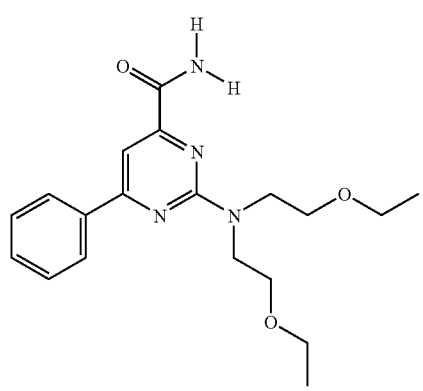 [SMILES: CCOCCN(CCOCC)c1nc(C(N)=O)cc(-c2ccccc2)n1]
191
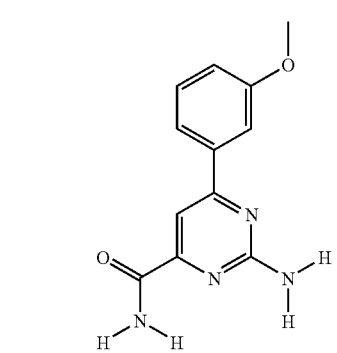 [SMILES: COc1cccc(-c2cc(C(N)=O)nc(N)n2)c1]
TABLE 1-continued
Specific Compounds
192
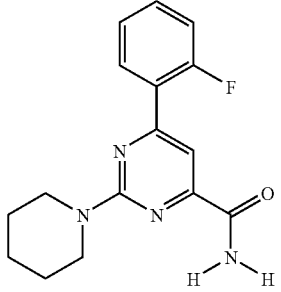 [SMILES: NC(=O)c1cc(-c2ccccc2F)nc(N2CCCCC2)n1]
193
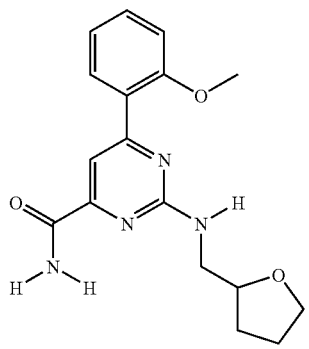 [SMILES: COc1ccccc1-c1cc(C(N)=O)nc(NCC2CCCO2)n1]
194
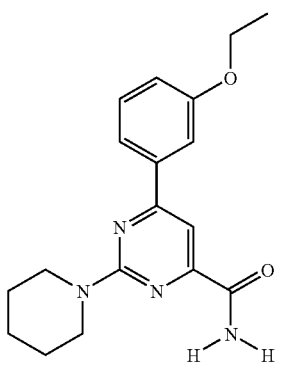 [SMILES: CCOc1cccc(-c2cc(C(N)=O)nc(N3CCCCC3)n2)c1]
195
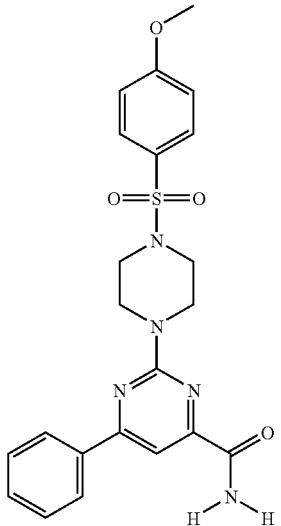 [SMILES: COc1ccc(S(=O)(=O)N2CCN(c3nc(C(N)=O)cc(-c4ccccc4)n3)CC2)cc1]

TABLE 1-continued
Specific Compounds
196 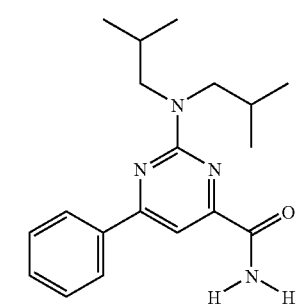 [SMILES: CC(C)CN(CC(C)C)c1nc(C(N)=O)cc(-c2ccccc2)n1]
197 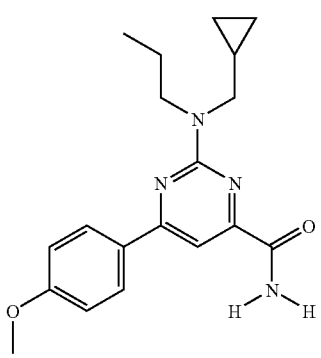 [SMILES: CCCN(CC1CC1)c1nc(C(N)=O)cc(-c2ccc(OC)cc2)n1]
198 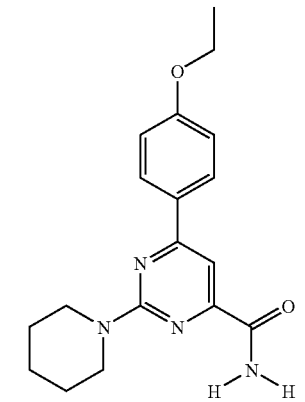 [SMILES: CCOc1ccc(-c2cc(C(N)=O)nc(N3CCCCC3)n2)cc1]
199 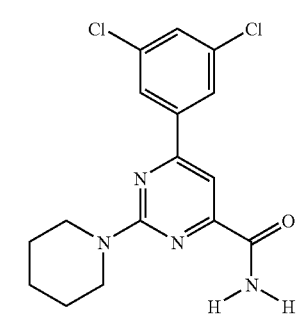 [SMILES: NC(=O)c1cc(-c2cc(Cl)cc(Cl)c2)nc(N2CCCCC2)n1]
TABLE 1-continued
Specific Compounds
200 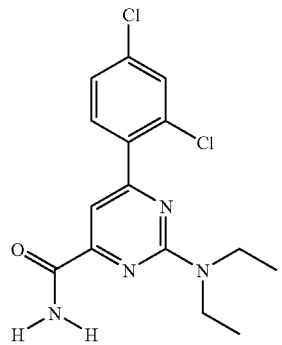
201 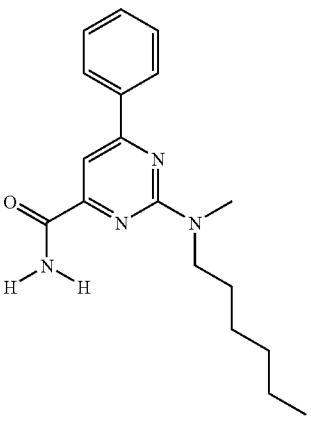 [SMILES: CCCCCCN(C)c1nc(C(N)=O)cc(-c2ccccc2)n1]
202 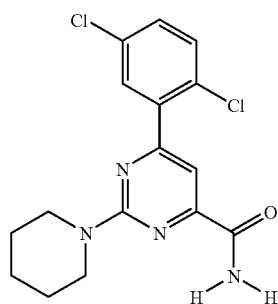 [SMILES: NC(=O)c1cc(-c2cc(Cl)ccc2Cl)nc(N2CCCCC2)n1]
203 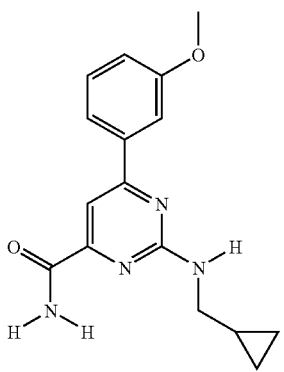 [SMILES: COc1cccc(-c2cc(C(N)=O)nc(NCC3CC3)n2)c1]

TABLE 1-continued
Specific Compounds
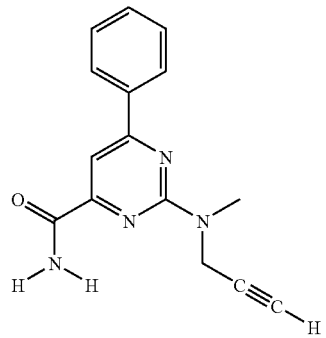 [SMILES: C#CCN(C)c1nc(C(N)=O)cc(-c2ccccc2)n1] 204
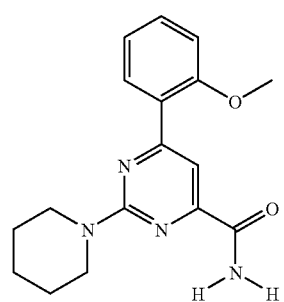 [SMILES: COc1ccccc1-c1cc(C(N)=O)nc(N2CCCCC2)n1] 205
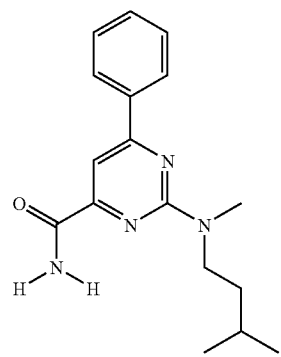 [SMILES: CC(C)CCN(C)c1nc(C(N)=O)cc(-c2ccccc2)n1] 206
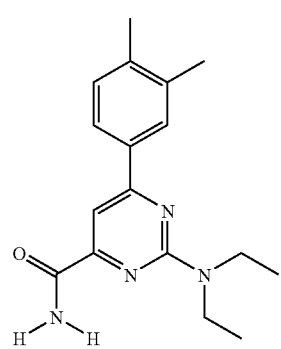 [SMILES: CCN(CC)c1nc(C(N)=O)cc(-c2ccc(C)c(C)c2)n1] 207
TABLE 1-continued
Specific Compounds
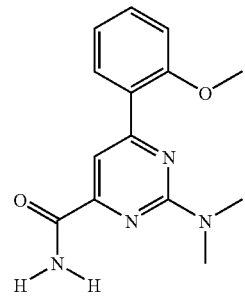 [SMILES: COc1ccccc1-c1cc(C(N)=O)nc(N(C)C)n1] 208
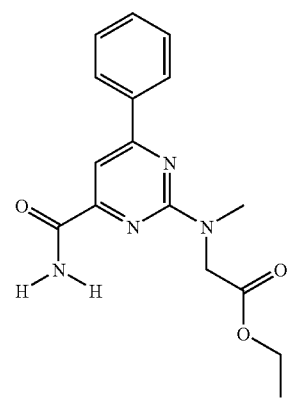 [SMILES: CCOC(=O)CN(C)c1nc(C(N)=O)cc(-c2ccccc2)n1] 209
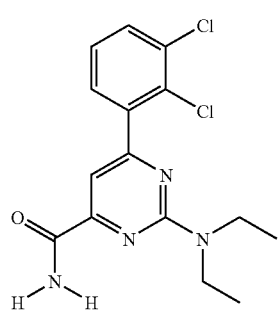 [SMILES: CCN(CC)c1nc(C(N)=O)cc(-c2cccc(Cl)c2Cl)n1] 210
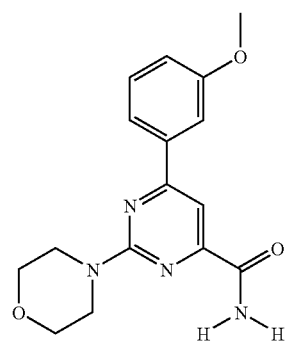 [SMILES: COc1cccc(-c2cc(C(N)=O)nc(N3CCOCC3)n2)c1] 211

TABLE 1-continued
Specific Compounds
212
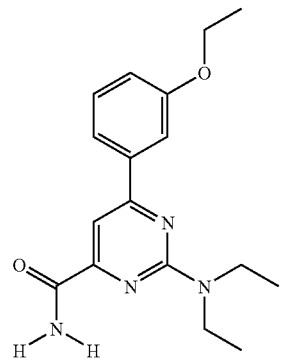 [SMILES: CCOc1cccc(-c2cc(C(N)=O)nc(N(CC)CC)n2)c1]
213
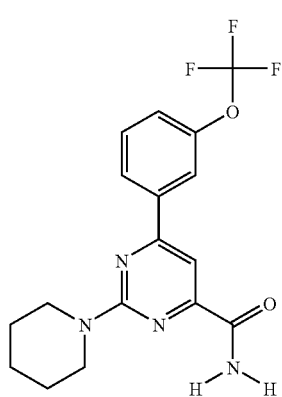 [SMILES: NC(=O)c1cc(-c2cccc(OC(F)(F)F)c2)nc(N2CCCCC2)n1]
214
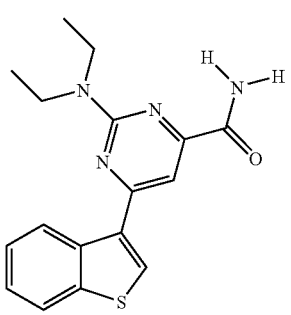 [SMILES: CCN(CC)c1nc(C(N)=O)cc(-c2csc3ccccc23)n1]
215
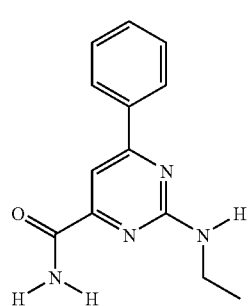 [SMILES: CCNc1nc(C(N)=O)cc(-c2ccccc2)n1]
TABLE 1-continued
Specific Compounds
216
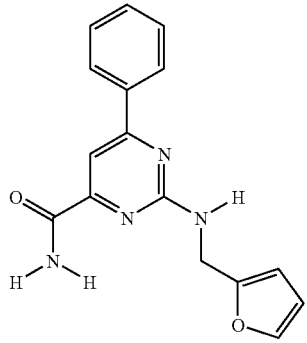
217
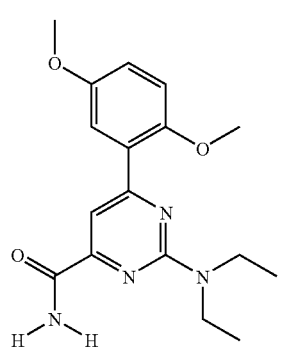 [SMILES: CCN(CC)c1nc(C(N)=O)cc(-c2cc(OC)ccc2OC)n1]
218
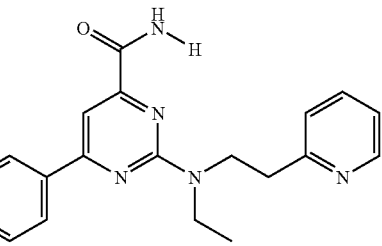
219
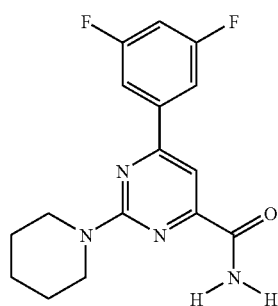 [SMILES: NC(=O)c1cc(-c2cc(F)cc(F)c2)nc(N2CCCCC2)n1]

TABLE 1-continued
Specific Compounds
220 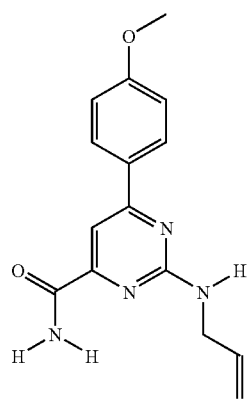 [SMILES: C=CCNc1nc(C(N)=O)cc(-c2ccc(OC)cc2)n1]
221 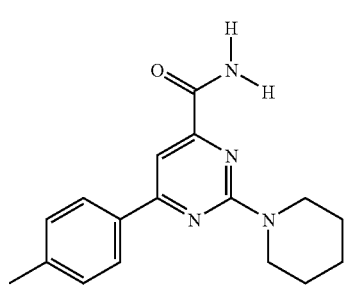 [SMILES: Cc1ccc(-c2cc(C(N)=O)nc(N3CCCCC3)n2)cc1]
222 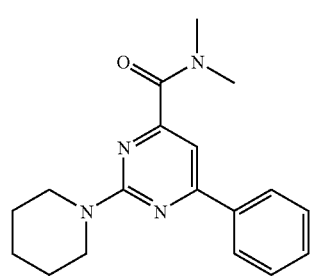 [SMILES: CN(C)C(=O)c1cc(-c2ccccc2)nc(N2CCCCC2)n1]
223 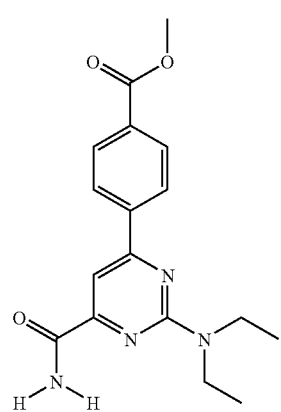 [SMILES: CCN(CC)c1nc(C(N)=O)cc(-c2ccc(C(=O)OC)cc2)n1]
TABLE 1-continued
Specific Compounds
224 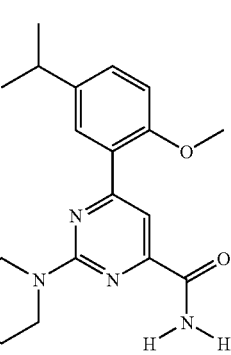
225 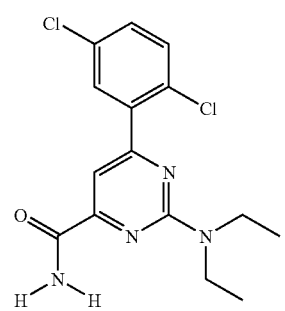 [SMILES: CCN(CC)c1nc(C(N)=O)cc(-c2cc(Cl)ccc2Cl)n1]
226 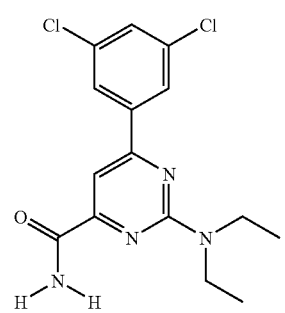 [SMILES: CCN(CC)c1nc(C(N)=O)cc(-c2cc(Cl)cc(Cl)c2)n1]
227 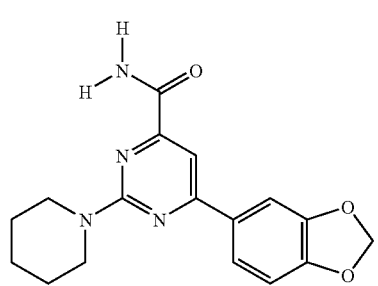 [SMILES: NC(=O)c1cc(-c2ccc3c(c2)OCO3)nc(N2CCCCC2)n1]

TABLE 1-continued
Specific Compounds
228
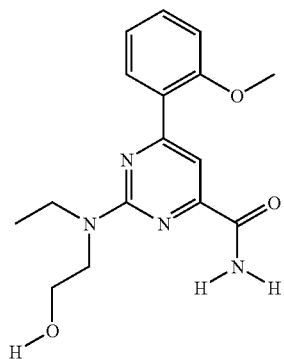 [SMILES: CCN(CCO)c1nc(C(N)=O)cc(-c2ccccc2OC)n1]
229
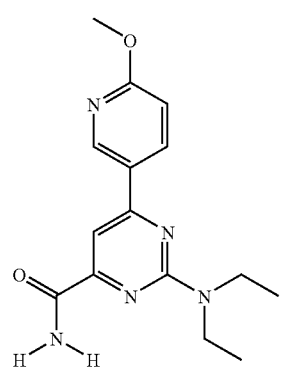 [SMILES: CCN(CC)c1nc(C(N)=O)cc(-c2ccc(OC)nc2)n1]
230
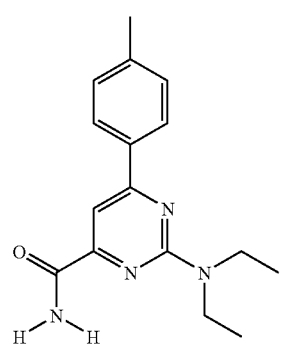 [SMILES: CCN(CC)c1nc(C(N)=O)cc(-c2ccc(C)cc2)n1]
231
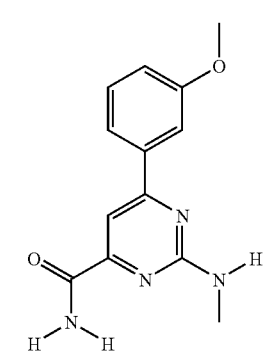 [SMILES: CNc1nc(C(N)=O)cc(-c2cccc(OC)c2)n1]
TABLE 1-continued
Specific Compounds
232
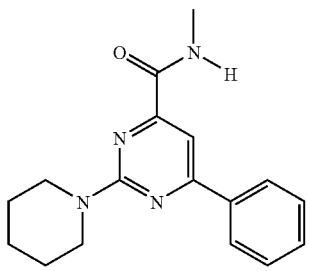 [SMILES: CNC(=O)c1cc(-c2ccccc2)nc(N2CCCCC2)n1]
233
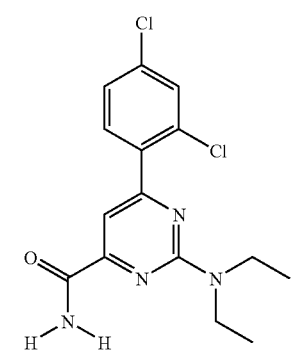
III. Synthetic Methods
The compounds of formulae I, II, and III can be produced via known synthetic methods. Schemes 1 and 2 illustrate two possible methods for producing the compounds of formula I.
Scheme 1:
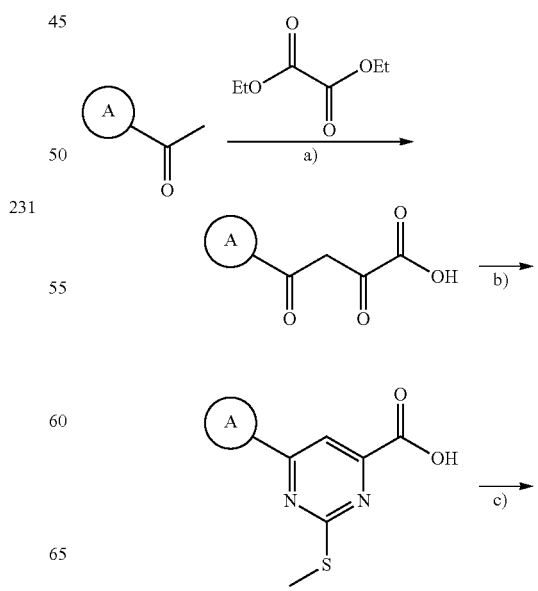

-continued

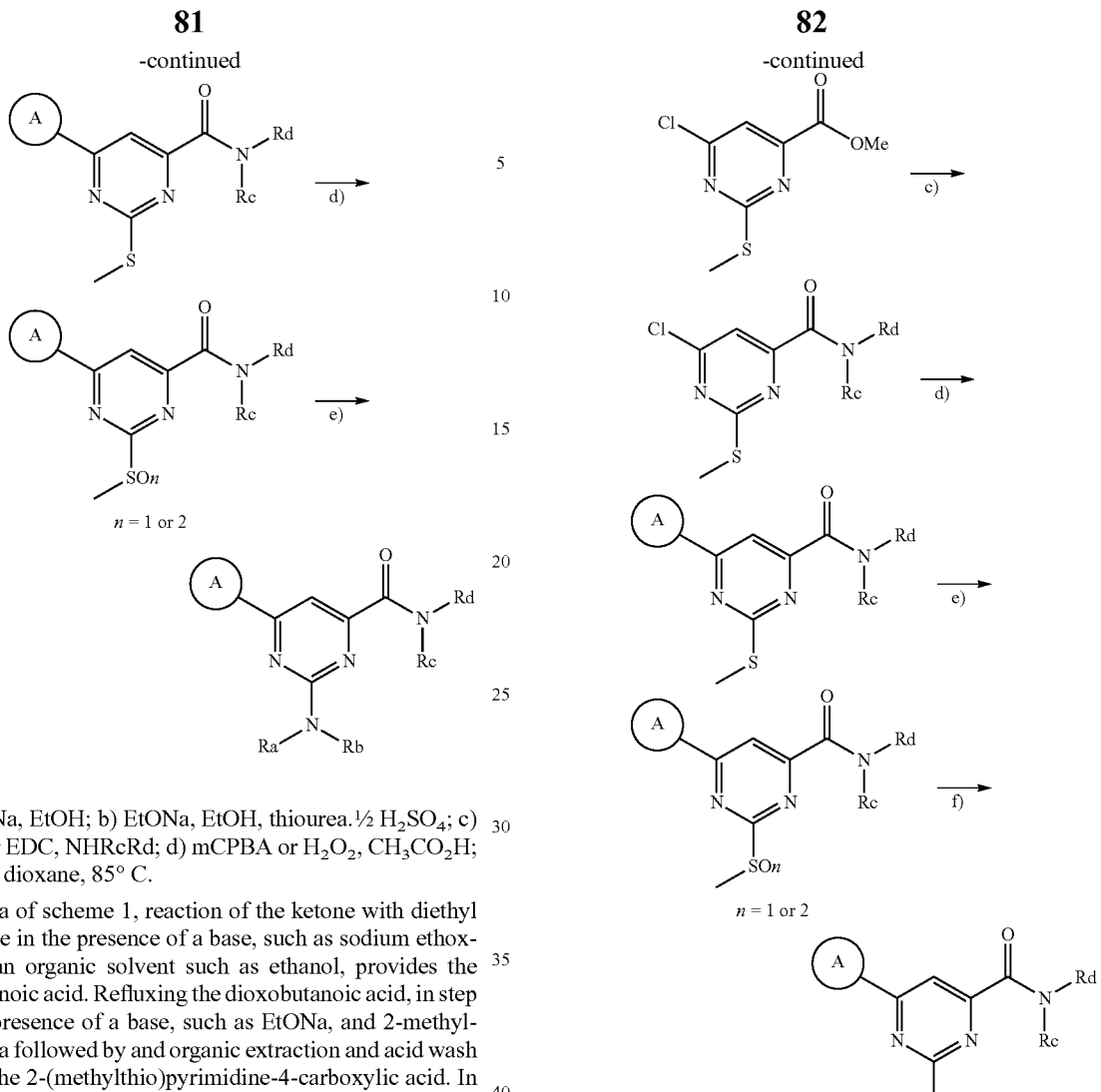

a) EtONa, EtOH; b) EtONa, EtOH, thiourea.½ H$_2$SO$_4$; c) PyBOP or EDC, NHRcRd; d) mCPBA or H$_2$O$_2$, CH$_3$CO$_2$H; HNRaRb, dioxane, 85° C.

In step a of scheme 1, reaction of the ketone with diethyl oxalacetate in the presence of a base, such as sodium ethoxide, and an organic solvent such as ethanol, provides the dioxobutanoic acid. Refluxing the dioxobutanoic acid, in step b, in the presence of a base, such as EtONa, and 2-methylisothiourea followed by and organic extraction and acid wash provides the 2-(methylthio)pyrimidine-4-carboxylic acid. In step c, the carboxylic acid is converted to the amide using standard amine coupling methodologies, such as with PyBOP or EDC, in the presence of the appropriate amine, e.g., NHRcRd. In step d, oxidation of the thiol with an oxidizing agent such as m-CPBA or H$_2$O$_2$ in CH$_3$CO$_2$H provides the sulfinyl or sulfonyl compound. In step e, reaction of the sulfinyl or sulfonyl compound with the appropriate amine, HNRaRb, in an organic solvent such as dioxane provides the compound of formula I.

Scheme 2:

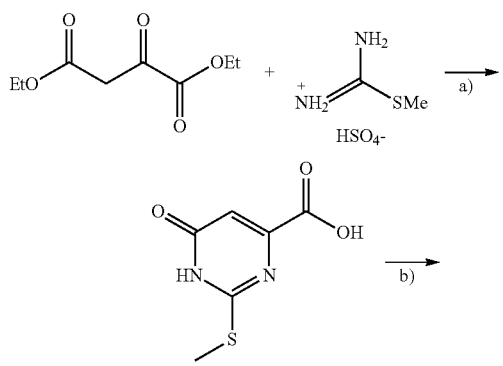

a) NaOH, H$_2$O; b) i) SOCl$_2$, PhMe reflux; ii) MeOH, DIEA, CHCl$_3$, 0° C. c) NHRcRd, CHCl$_3$; d) A-B(OR)$_2$, PdCl$_2$(dppf), K$_3$PO4, DMF/DME/H$_2$O, 75° C., e) i) mCPBA, CHCl$_3$; ii) Me$_2$S; f) HNRaRb, NMM, DMSO, 75° C.

In step a of scheme 2, reaction of diethyl diethyl oxalacetate and methylisothiourea provides the 2-methylthio-6-oxo-1,6-dihydro-pyrimidin-4-yl carboxylic acid. In step b, refluxing the carboxylic acid with tionyl chloride in an organic solvent such as tolune, followed by treatment with methanol provides the 2-methylthio-6-chloro-pyrimidin-4-yl carboxylic acid methyl ester. In step c, the methyl ester is converted to the amide using the appropriate amine, such as NHRcRd. In step d, the boronic acid derivative of Ring A (such as [Ring A]-B(OR)$_2$, is coupled to the pyrimidine-4-carboxylic amide using a coupling reagent, such as PdCl$_2$(dppf). The desired compound is produced via synthetic steps e and f, which are similar to steps d and e in scheme 1.

IV. Uses, Routes of Administration, and Formulation

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, the present invention provides a method of treating a condition, disease, or disorder implicated by ABC transporter activity. In certain embodiments, the present invention provides a method of treating a condition, disease, or disorder implicated by a deficiency of ABC transporter activity, the method comprising administering a composition comprising a compound of formula (I) to a subject, preferably a mammal, in need thereof.

In certain preferred embodiments, the present invention provides a method of treating Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease, Straussler-Scheinker disease, secretory diarrhea, polycystic kidney disease, chronic obstructive pulmonary disease (COPD), dry eye disease, and Sjögren's Syndrome, comprising the step of administering to said mammal an effective amount of a composition comprising a compound of formula (I), or a preferred embodiment thereof as set forth above.

According to an alternative preferred embodiment, the present invention provides a method of treating cystic fibrosis comprising the step of administering to said mammal a composition comprising the step of administering to said mammal an effective amount of a composition comprising a compound of formula (I), or a preferred embodiment thereof as set forth above.

According to the invention an "effective amount" of the compound or pharmaceutically acceptable composition is that amount effective for treating or lessening the severity of one or more of Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker disease, secretory diarrhea, polycystic kidney disease, chronic obstructive pulmonary disease (COPD), dry eye disease, and Sjögren's Syndrome.

The compounds and compositions, according to the method of the present invention, may be administered using any amount and any route of administration effective for treating or lessening the severity of one or more of Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker disease, secretory diarrhea, polycystic kidney disease, chronic obstructive pulmonary disease (COPD), dry eye disease, and Sjögren's Syndrome.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as modulators of ABC transporters. Thus, without wishing to be bound by any particular theory, the compounds and compositions are particularly useful for treating or lessening the severity of a disease, condition, or disorder where hyperactivity or inactivity of ABC transporters is implicated in the disease, condition, or disorder. When hyperactivity or inactivity of an ABC transporter is implicated in a particular disease, condition, or disorder, the disease, condition, or disorder may also be referred to as a "ABC transporter-mediated disease, condition or disorder". Accordingly, in another aspect, the present invention provides a method for treating or lessening the severity of a disease, condition, or disorder where hyperactivity or inactivity of an ABC transporter is implicated in the disease state.

The activity of a compound utilized in this invention as a modulator of an ABC transporter may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121; hereby incorporated by reference. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating ABC transporter activity in a biological sample or a patient (e.g., in vitro or in vivo), which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of ABC transporter activity in a biological sample is useful for a variety of purposes that are known to one of skill in the art. Examples of such purposes include, but are not limited to, the study of ABC transporters in biological and pathological phenomena; and the comparative evaluation of new modulators of ABC transporters.

In yet another embodiment, a method of modulating activity of an anion channel in vitro or in vivo, is provided comprising the step of contacting said channel with a compound of formula (I). In preferred embodiments, the anion channel is a chloride channel or a bicarbonate channel. In other preferred embodiments, the anion channel is a chloride channel.

According to an alternative embodiment, the present invention provides a method of increasing the number of functional ABC transporters in a membrane of a cell, comprising the step of contacting said cell with a compound of formula (I). The term "functional ABC transporter" as used herein means an ABC transporter that is capable of transport activity. In preferred embodiments, said functional ABC transporter is CFTR.

According to another preferred embodiment, the activity of the ABC transporter is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of a ABC transporter or a fragment thereof in a biological sample in vitro or in vivo comprising (i) a composition comprising a compound of formula (I) or any of the above embodiments; and (ii) instructions for a.) contacting the composition with the biological sample and b.) measuring activity of said ABC transporter or a fragment thereof. In one embodiment, the kit further comprises instructions for a.) contacting an additional composition with the biological sample; b.) measuring the activity of said ABC transporter or a fragment thereof in the presence of said additional compound, and c.) comparing the activity of the ABC transporter in the presence of the additional compound with the density of the ABC transporter in the presence of a composition of formula (I). In preferred embodiments, the kit is used to measure the density of CFTR.

In order that the invention described herein may be more fully understood, the following examples are set forth. It should be understood that these examples are for illustrative purposes only and are not to be construed as limiting this invention in any manner.

V. Preparations and Examples

Example 1

2-(dimethylamino)-6-(2-methoxyphenyl)pyrimidine-4-carboxamide

Step a: 4-(2-methoxyphenyl)-2,4-dioxobutanoic acid

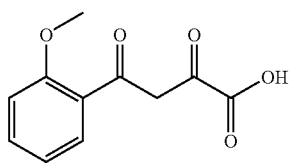 [SMILES: COc1ccccc1C(=O)CC(=O)C(=O)O]

To a stirred solution of diethyl oxalate (16 g, 110 mmol) and sodium ethoxide (100 mL, 21% by wt. in ethanol, 300 mmol) was added dropwise a solution of 2-methoxy acetophenone (15 g, 100 mmol) in ethanol (100 mL). The reaction mixture was allowed to stir at ambient temperature overnight. The resulting solution was concentrated to approximately 50 mL on a rotary evaporator, followed by partitioning between diethyl ether (100 mL) and water (250 mL). The aqueous layer was adjusted to pH=3 with conc. HCl to give a suspension with a fine white precipitate, which was heated at 100° C. for 5-10 minutes followed by cooling in an ice bath for 1 h. The precipitate was filtered, washed with water (20 mL), and dried overnight under high vacuum to give 4-(2-methoxyphenyl)-2,4-dioxobutanoic acid. $^1$H NMR (300 MHz, CDCl$_3$) δ 7.96 (q, J=9.0, 3.0 Hz, 1H), 7.53 (t, J=6.0 Hz, 1H), 7.47 (s, 0.9H keto form), 7.24 (s, 1.1H enol form), 7.06 (t, J=6.0 Hz, 1H), 7.00 (d, J=9.0 Hz, 1H), 3.97 (s, 3H). ESI-MS m/z 220.9 (M−H)$^−$.

Step b: 6-(2-methoxyphenyl)-2-(methylthio)pyrimidine-4-carboxylic acid

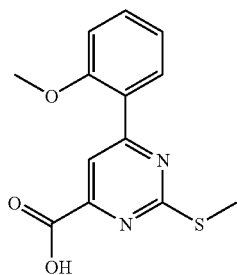

A mixture of 2,4-dioxo-4-(2-methoxyphenyl)butyric acid (15.6 g, 70 mmol), 2-methyl-isothiourea sulfate (10.4 g, 73.5 mmol) and sodium ethoxide (26 mL, 21% by wt. in ethanol, 70 mmol) in ethanol (200 mL) was heated to reflux overnight. The resulting solution was reduced to approximately 50 mL using a rotary evaporator, water (200 mL) was added to give a suspension, which was adjusted to pH >9 with 10% NaOH. The mixture was extracted with diethyl ether (100 mL). The aqueous layer was taken to pH=3 with conc. HCl solution to give a suspension, which was heated to 90° C. for 10 minutes. Upon cooling in an ice bath for 1 h, a precipitate formed, which was filtered, washed with water (20 mL), and dried overnight under vacuum to give 6-(2-methoxyphenyl)-2-(methylthio)pyrimidine-4-carboxylic acid. $^1$H NMR (300 MHz, CDCl$_3$) δ 8.45 (s, 1H), 8.10 (dd, J=7.5, 1.8 Hz, 1H), 7.48 (m, 1H), 7.09 (t, J=6.9 Hz, 1H), 7.02 (d, J=8.7 Hz, 1H), 3.94 (s, 3H), 2.67 (s, 3H). HPLC ret. time 2.02 min, 10-100% CH$_3$CN, 5 min gradient; ESI-MS m/z 277.1 (M+H)$^+$.

Step c: 6-(2-methoxyphenyl)-2-(methylthio)pyrimidine-4-carboxamide

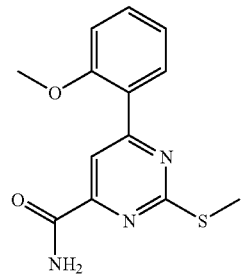

To a stirred suspension of 6-(2-methoxyphenyl)-2-(methylthio)pyrimidine-4-carboxylic acid (9.8 g, 40 mmol), triethylamine (33 mL, 240 mmol), and ammonium chloride (11 g, 200 mmol) in DMF (40 mL) was added PyBOP (21.9 g, 42 mmol) in five portions. The reaction was complete in 2 h, as determined by LCMS analysis. The reaction mixture was poured into water (1.5 L) and stirred for 10 minutes. The precipitate was collected by filtration and dried overnight under high vacuum to give 6-(2-methoxyphenyl)-2-(methylthio)pyrimidine-4-carboxamide. $^1$H NMR (300 MHz, CDCl3) δ 8.40 (s, 0.7H), 8.05 (m, 1.3H), 7.74 (bs, 1H), 7.44 (m, 1H), 7.05 (m, 2H), 5.78 (bs, 1H), 3.92 (s, 3H); 2.65 (s, 3H). HPLC ret. time 2.71 min, 10-100% CH$_3$CN, 5 min gradient; ESI-MS m/z 245.9 (M+H)$^+$.

Step d: 6-(2-methoxyphenyl)-2-(methylsulfinyl)pyrimidine-4-carboxamide and 6-(2-methoxyphenyl)-2-(methylsulfonyl)pyrimidine-4-carboxamide

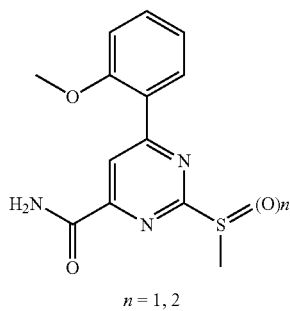

n = 1, 2

To a flask containing 6-(2-methoxyphenyl)-2-(methylthio)pyrimidine-4-carboxamide (2.75 g, 8.5 mmol) in 5 mL of DCM was added mCPBA (2.3 g, 10.2 mmol, 77% by wt., remainder 3-chlorobenzoic acid and water). After stirring for 3 h at room temperature a precipitate formed, which was filtered to yield 6-(2-methoxyphenyl)-2-(methylsulfinyl)pyrimidine-4-carboxamide and 6-(2-methoxyphenyl)-2-(methylsulfonyl)pyrimidine-4-carboxamide.as a white solid [mixture of sulfone and sulfoxide]. HPLC ret. time 1.97 min, 10-100% CH$_3$CN, 5 min gradient; ESI-MS m/z 308.1 (M+H)$^+$. The crude product was used in the next step without further purification.

The sulfone is obtained as a primary product when excess oxidizing agent, mCPBA, is used.

Step e: 2-(dimethylamino)-6-(2-methoxyphenyl) pyrimidine-4-carboxamide (192)

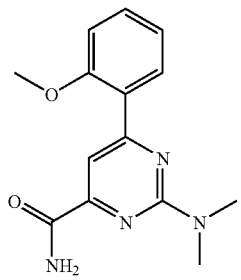

6-(2-Methoxyphenyl)-2-(methylsulfinyl)pyrimidine-4-carboxamide (46 mg, 0.15 mmol), 1,4-dioxane (2 mL), DIPEA (80 μL, 0.45 mmol), and dimethylamine hydrochloride (26 mg, 0.3 mmol) were added to a vial (8 mL). The vial was sealed and heated at 85° C. for two days. After the reaction solution cooled to room temperature, the solvent was removed under vacuum in a Savant SpeedVac. The resulting residue was purified by Prep. HPLC. $^1$H NMR (300 MHz, CDCl$_3$) δ 7.95 (q, J=7.8, 1.8 Hz, 1H), 7.88 (s, 1H), 7.77 (bs, 1H), 7.40 (m, 1H), 7.04 (t, J=9.0 Hz, 1H), 6.98 (d, J=6.0 Hz, 1H), 5.78 (bs, 1H), 3.92 (s, 3H), 3.26 (s, 6H). HPLC ret. time 2.76 min, 10-100% CH$_3$CN, 5 min gradient; ESI-MS m/z 273.1 (M+H)$^+$.

Example 2

2-(N-methylphenethylamino)-6-phenylpyrimidine-4-carboxamide

Step a: 2,4-dioxo-4-phenylbutanoic acid

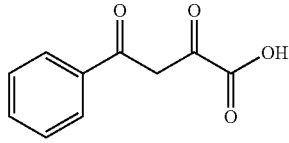 [SMILES: O=C(O)C(=O)CC(=O)c1ccccc1]

To a stirred solution of diethyl oxalate (21.9 g, 150 mmol) and sodium ethoxide (168 mL, 21% wt. solution, 450 mmol) was added dropwise a solution of acetophenone (18 g, 150 mmol) in ethanol (120 mL). The reaction mixture was allowed to stir at ambient temperature for 15 h. The reaction mixture was concentrated to ca. 70 mL and partitioned between diethyl ether (50 mL) and water (200 mL). The phases were separated, and the aqueous layer adjusted to pH=1 with conc. HCl before being extracted with diethyl ether (3×100 mL). The combined ether extracts were dried over MgSO$_4$ and evaporated to yield 2,4-dioxo-4-phenylbutanoic acid. $^1$H NMR (DMSO-d$_6$, 300 MHz) δ 8.05 (d, J=7.2 Hz, 1.8H enol form), 7.96 (d, J=6.9 Hz, 0.2H keto form), 7.69 (t, J=7.5 Hz, 1H), 7.56 (t, J=8.1 Hz, 2H), 7.08 (s, 0.9H enol form), 4.56 (s, 0.1H keto form). $^{13}$C NMR (DMSO-d$_6$, 75 MHz) δ 190.7, 170.7, 163.6, 135.1, 134.6, 129.7, 128.4, 98.5.

Step b: 2-methylsulfanyl-6-phenylpyrimidine-4-carboxylic acid

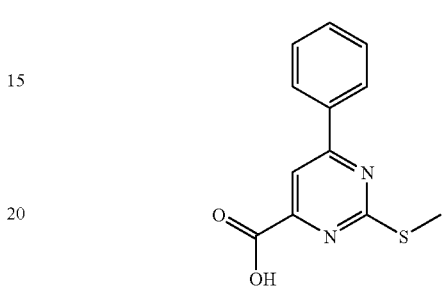

A mixture of 2,4-dioxo-4-phenylbutanoic acid (19.2 g, 100 mmol), 2-methylisothiourea sulfate (27.8 g, 100 mmol) and sodium ethoxide (37 mL, 21% wt. solution, 100 mmol) in ethanol (200 mL) was heated to reflux overnight. After removal of volatiles, water was added (200 mL) to give a suspension, which was adjusted to pH>9 with 10% NaOH. The mixture was extracted with diethyl ether (2×100 mL). The aqueous layer was taken to pH=2 with conc. HCl and extracted with diethyl ether (4×100 mL). The combined ethereal extracts were evaporated, and the residue was dried in vacuo overnight to afford 22.0 g of 2-methylsulfanyl-6-phenylpyrimidine-4-carboxylic acid as a yellow solid. $^1$H NMR (DMSO-d$_6$, 300 MHz) δ 8.24 (dd, J=7.8, 1.8 Hz, 2H), 8.12 (s, 1H), 7.58 (m, 3H), 2.64 (s, 3H). $^{13}$C NMR (DMSO-d$_6$, 75 MHz) δ 172.8, 165.7, 165.6, 157.9, 135.8, 132.5, 129.8, 128.0, 14.6. HPLC ret. time 1.95 min, 10-100% CH$_3$CN, 5 min run. ESI-MS m/z 247.1 (M+H)$^+$.

Step c: 2-(methylthio)-6-phenylpyrimidine-4-carboxamide

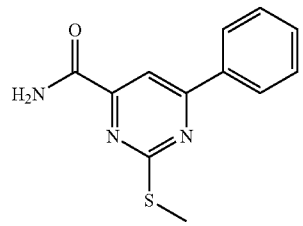 [SMILES: CSc1nc(C(N)=O)cc(-c2ccccc2)n1]

N-Methylmorpholine (2.31 mL, 21 mmol) was added dropwise by syringe to a mixture of 2-methylsulfanyl-6-phenylpyrimidine-4-carboxylic acid (3.45 g, 14 mmol), ammonium chloride (4.27 g, 80 mmol), HOBt (2.84 g, 21 mmol), and EDC (4.0 g, 21 mmol) in DMF (40 mL) at room temperature. The reaction solution was stirred at room temperature for 3 h before the DMF was removed by rotary evaporation. Column chromatography (SiO$_2$, DCM/EtOAc 5:1) afforded 3.23 g of 2-(methylthio)-6-phenylpyrimidine-4-carboxamide as a white solid. $^1$H NMR (DMSO-d$_6$, 300 MHz) δ 8.25 (m, 2H), 8.13 (s, 1H), 7.59 (m, 3H), 2.62 (s, 3H). HPLC ret. time 2.71 min, 10-100% CH$_3$CN, 5 min gradient. ESI-MS m/z 246.1 (M+H)$^+$.

Step d: 2-(methanesulfonyl)-6-phenylpyrimidine-4-carboxamide

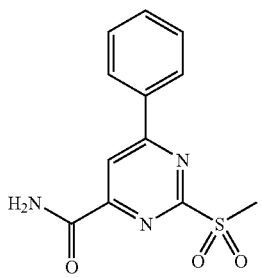 [SMILES: CS(=O)(=O)c1nc(C(N)=O)cc(-c2ccccc2)n1]

To a flask containing 2-methylsulfanyl-6-phenylpyrimidine-4-carboxamide (2.0 g, 8.2 mmol) in 100 mL of DCM was added mCPBA (30 mmol, 5.18 g, 77% by wt., remainder 3-chlorobenzoic acid and water). After stirring at room temperature for 3 h, a white precipitate formed, which was filtered off and washed on the filter with cold DCM (20 mL) to yield 2-(methanesulfonyl)-6-phenylpyrimidine-4-carboxamide as a white solid.

$^1$H NMR (DMSO-d$_6$, 300 MHz) δ 8.67 (s, 1H), 8.50 (s, 1H), 8.34 (dd, J=7.8, 1.5 Hz, 2H), 8.18 (s, 1H), 7.63 (m, 3H), 3.60 (s, 3H). HPLC ret. time 2.10 min, 10-100% CH$_3$CN, 5 min run. ESI-MS m/z 278.1 (M+H)$^+$.

Step e: 2-(N-methylphenethylamino)-6-phenylpyrimidine-4-carboxamide (title compound)

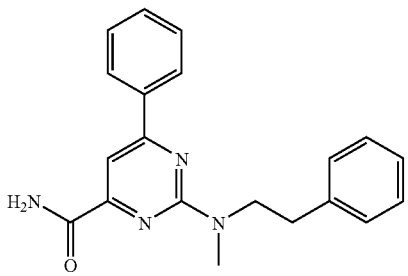 [SMILES: CN(CCc1ccccc1)c1nc(C(N)=O)cc(-c2ccccc2)n1]

2-Methanesulfonyl-6-phenylpyrimidine-4-carboxamide (70 mg, 0.25 mmol), 1,4-dioxane (4 mL), DIPEA (0.3 mL, 2.0 mmol) and N-methylphenethylamine (82 mg, 0.6 mmol) were added to a 8 mL vial. The vial was sealed and heated at 85° C. for two days. The reaction mixture was allowed to cool to room temperature, and the solvent then removed by centrifugal evaporation. The residue was purified by preparative HPLC to afford 43 mg of 2-(N-methylphenethylamino)-6-phenylpyrimidine-4-carboxamide. $^1$H NMR (CDCl$_3$, 300 MHz) δ 8.14 (m, 2H), 7.74 (s, 1H), 7.67 (br s, 1H), 7.47 (m, 3H), 7.25 (m, 5H), 5.79 (br s, 1H), 3.95 (t, J=6.9 Hz, 2H), 3.21 (s, 3H), 2.97 (t, J=6.9 Hz, 2H). HPLC ret. time 3.25 min, 10-100% CH$_3$CN, 5 min run. ESI-MS m/z 333.3 (M+H)$^+$.

Example 3

2-diethylamino-6-(2,6-dimethoxy-phenyl)-pyrimidine-4-carboxylic acid amide

Step a: 2-methylsulfanyl-6-oxo-1,6-dihydro-pyrimidine-4-carboxylic acid

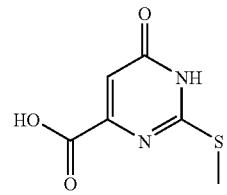

Neat diethyl oxalacetate (23.5 g, 125 mmol) was added to a solution of sodium hydroxide (15 g, 0.375 mol, 3 eq) in water (150 mL), giving a yellow solution. Solid S-methylisothiourea sulfate (17.4 g, 62.5 mmol, 0.5 eq) was added to the stirred solution. The mixture was stirred 15 hours. Concentrated HCl (40 mL, 0.48 mol) was added bringing the pH to 1, the resultant pale orange-pink suspension was stirred vigorously for 2 hours then filtered. The filter cake was washed with water (100 mL), and dried under high vacuum to afford 2-methylsulfanyl-6-oxo-1,6-dihydro-pyrimidine-4-carboxylic acid as an off-white solid. $^1$H NMR (500 MHz, DMSO-d$_6$) ☐ 13.22 (br s, 1H), 6.60 (s, 1H), 3.37 (br s, 1H), 2.53 (s, 3H); ESI-MS m/z 186.9 (M+H)$^+$.

Step b: 6-chloro-2-methylsulfanyl-pyrimidine-4-carboxylic acid methyl ester

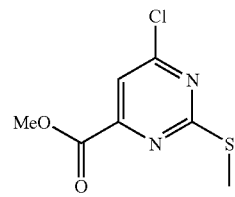

A 250 mL flask was charged with 2-methylsulfanyl-6-oxo-1,6-dihydro-pyrimidine-4-carboxylic acid (11.6 g, 62.5 mmol), toluene (60 mL), thionyl chloride (60 mL, 0.8 mol, 13 eq.), DMF (0.3 mL), and pyridine (1 mL), and the resultant stirred suspension was heated to reflux. The suspension clarified after 30 min. After 3 hours at reflux, the mixture was concentrated in vacuo, and co-evaporated with additional toluene (30 mL). The biphasic brown residue was dissolved in chloroform (100 mL), cooled to 0° C., and DIEA (56 mL, 0.31 mol, 5 eq.) added dropwise over 20 min followed by methanol (12.7 mL, 0.31 mol, 5 eq.) over 5 min. The mixture was warmed to room temperature, and poured into saturated aqueous sodium bicarbonate (350 mL). The organic layer was washed with saturated aqueous ammonium chloride (350 mL), dried (Na$_2$SO$_4$), filtered, and concentrated in vacuo to a brown semi-solid. Overnight drying under high vacuum afforded 6-chloro-2-methylsulfanyl-pyrimidine-4-carboxylic acid methyl ester that was taken to the next step without further purification. ¹H NMR (500 MHz, CDCl₃) ☐ 7.60 (s, 1H), 3.98 (s, 3H), 2.60 (s, 3H); ESI-MS m/z 218.9 (M+H)⁺.

Step c:
6-chloro-2-methylsulfanyl-pyrimidine-4-carboxylic acid amide

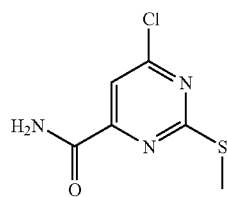

A 500 mL flask was charged with the 6-chloro-2-methylsulfanyl-pyrimidine-4-carboxylic acid methyl ester (4.37 g, 20 mmol), and chloroform (30 mL). Ammonia (57 mL, 7 M in methanol, 0.4 mol, 20 eq.) was added with stirring. HPLC analysis after 20 minutes indicated no starting methyl ester remained. The mixture was sparged with nitrogen for 30 min, then concentrated in vacuo, and dried under high vacuum to afford the 6-chloro-2-methylsulfanyl-pyrimidine-4-carboxylic acid amide (4.21 g, quant.) in sufficient purity for use in the next step. ¹H NMR (500 MHz, CDCl₃) ☐ 7.76 (s, 1H), 7.60 (br s, 1H), 5.97 (br s, 1H), 2.61 (s, 3H); ESI-MS m/z 204.1 (M+H)⁺.

Step d: 6-(2,6-dimethoxy-phenyl)-2-methylsulfanyl-pyrimidine-4-carboxylic acid amide

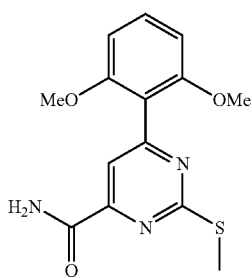 [SMILES: COc1cccc(OC)c1-c1cc(C(N)=O)nc(SC)n1]

A 7 mL teflon-faced screw-cap vial was charged with 2,6-dimethoxyphenyl-boronic acid (218 mg, 1.2 mmol, 2 eq.) and dichloro-bis-(diphenylphosphinoferrocene)-palladium-dichloromethane adduct (49 mg, 60 μmol, 10 mol %). In a glove box under a nitrogen atmosphere (O₂ content<=0.5%), the vial was charged with a solution of the 6-chloro-2-methylsulfanyl-pyrimidine-4-carboxylic acid amide (122 mg, 0.6 mmol) in degassed DMF/DME (1/1, 4.5 mL), and a degassed aqueous 1 M solution of potassium phosphate (1.0 mL, 1 mmol, 1.7 eq.). The vial was sealed, withdrawn from the glove box, and agitated in an incubator shaker at 75° C. for 16 hours. The cooled mixture was then diluted with chloroform (15 mL), and washed with brine (20 mL, 2×10 mL), and aqueous 1 M potassium carbonate (10 mL). The organic layer (solution of 6-(2,6-dimethoxy-phenyl)-2-methylsulfanyl-pyrimidine-4-carboxylic acid amide in chloroform) was then used directly in the next step.

Step e: 6-(2,6-dimethoxy-phenyl)-2-methanesulfonyl-pyrimidine-4-carboxylic acid amide

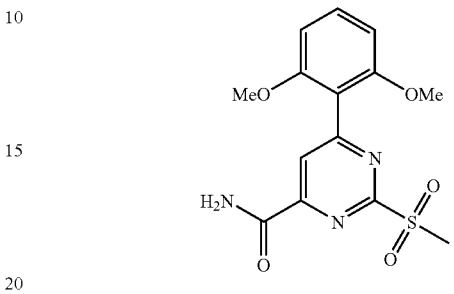

A 50 mL Falcon centrifuge tube containing a solution of 6-(2,6-dimethoxy-phenyl)-2-methylsulfanyl-pyrimidine-4-carboxylic acid amide from the previous step (assumed 0.6 mmol) in chloroform (15 mL) was charged with solid mCPBA (0.57 g, 70% purity, the remaining 30% was comprised of water and benzoic acid, 2.4 mmol, 4 eq., ca. 25% by weight water), and the mixture shaken at room temperature overnight. Dimethyl sulfide (0.22 mL, 3 mmol, 5 eq.) was added to the resultant light brown-orange suspension to quench residual MCPBA, and the mixture shaken for 2 hours. The mixture was then washed with aqueous 1 M sodium hydroxide (10 mL), brine (10 mL), dried (Na₂SO₄), filtered and concentrated to dryness in a centrifugal evaporator. The residue 6-(2,6-dimethoxy-phenyl)-2-methanesulfonyl-pyrimidine-4-carboxylic acid amide was then dissolved in DMSO (1.8 mL), and used directly in the next reaction.

Step f: 2-diethylamino-6-(2,6-dimethoxy-phenyl)-pyrimidine-4-carboxylic acid amide

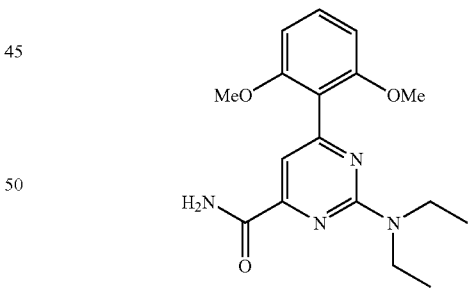

A 4 mL screw-cap vial was charged with a solution of 6-(2,6-dimethoxy-phenyl)-2-methanesulfonyl-pyrimidine-4-carboxylic acid amide (assumed 0.3 mmol) in DMSO (0.9 mL). A solution of diethylamine and N-methyl-morpholine (NMM) in DMSO (0.3 mL, 3 M in both, 0.9 mmol, 3 eq.) was added, and the sealed vial was heated at 75° C. for 22 hours. The mixture was then submitted for purification by preparative HPLC to afford 18 mg (18%) of the 2-diethylamino-6-(2,6-dimethoxy-phenyl)-pyrimidine-4-carboxylic acid amide. ¹H NMR (300 MHz, CDCl₃) ☐ 7.79 (br s, 1H), 7.30 (t, J=8.3 Hz, 1H), 7.26 (s, 1H), 6.61 (d, J=8.3 Hz, 2H), 6.16 (brs, 1H), 3.74 (s, 6H), 3.66 (q, J=6.9 Hz, 4H), 1.22 (t, J=6.9 Hz, 6H); HPLC ret. time 2.85 min., 10-100% CH$_3$CN, 5 min gradient; ESI-MS m/z 330.2 (M+H)$^+$.

Example 4

Additional Compounds

The remaining compounds described in TABLE 1 were produced using the procedures described herein along with known synthetic methods. TABLE 2 includes physical data characterizing each synthesized compound.

TABLE 2

| Compd No. | LC-MS M + 1 | LC-RT min | NMR |
|---|---|---|---|
| 1 | 324. | 3.39 | |
| 2 | 308.1 | 2.81 | |
| 3 | 390. | 3.48 | |
| 4 | 286.1 | 2.45 | |
| 5 | 314.2 | 3.2 | 1H NMR (300 MHz, CDCl$_3$) δ 7.98-7.93 (m, 2H), 7.73 (br s, 1H), 7.37 (dt, J = 1.7, 7.8 Hz, 1H), 7.03 (t, J = 7.5 Hz, 1H), 6.97 (d, J = 8.3 Hz, 1H), 5.66 (br s, 1H), 4.13 (q, J = 6.9 Hz, 2H), 3.70 (q, J = 7.0 Hz, 4H), 1.48 (t, J = 6.9 Hz, 3H), 1.24 (t, J = 7.0 Hz, 6H) |
| 6 | 318.1 | 3.14 | |
| 7 | 256.1 | 2.93 | 1H NMR (300 MHz, CDCl$_3$) δ 8.15 (m, 2H), 7.73 (m, 2H), 7.46 (m, 3H), 5.68 (s, 1H), 3.80 (m, 2H), 3.26 (s, 3H), 1.25 (t, J = 9.0 Hz, 3H). |
| 8 | 342.2 | 3.02 | 1H NMR (300 MHz, CDCl$_3$) δ 7.87 (s, 1H), 7.71 (br s, 1H), 7.52 (d, J = 2.7 Hz, 1H), 6.98-6.87 (m, 3H), 5.74 (br s, 1H), 3.89-3.81 (m, 10H), 1.76-1.57 (m, 6H) |
| 9 | 243.1 | 3.08 | |
| 10 | 338.1 | 3.38 | |
| 11 | 310.2 | 3.44 | 1H NMR (300 MHz, CDCl$_3$) δ 7.69 (br s, 1H), 7.34 (s, 1H), 7.28-7.11 (m, 3H), 5.54 (br s, 1H), 3.84 (app t, J = 5.3 Hz, 4H), 2.33 (s, 3H), 2.30 (s, 3H), 1.73-1.51 (m, 6H) |
| 12 | 334.1 | 3.24 | |
| 13 | 309. | 2.92 | |
| 14 | 268. | 2.99 | |
| 15 | 310.1 | 3.01 | |
| 16 | 282.1 | 3.18 | |
| 17 | 368.2 | 3.36 | |
| 18 | 319. | 2.46 | |
| 19 | 314.2 | 2.71 | |
| 20 | 314.2 | 3.21 | |
| 21 | 290.1 | 3.39 | 1H NMR (300 MHz, CDCl$_3$) δ 7.69 (br s, 1H), 7.57 (d, J = 3.7 Hz, 1H), 7.49 (s, 1H), 6.78 (dd, J = 1.0, 3.7 Hz, 1H), 5.48 (br s, 1H), 3.65 (q, J = 7.0 Hz, 4H), 2.53 (s, 3H), 1.24 (t, J = 7.0 Hz, 6H) |
| 22 | 313.2 | 2.99 | |
| 23 | 299.3 | 3.89 | |
| 24 | 362.2 | 3.32 | 1H NMR (300 MHz, CDCl$_3$) δ 7.94 (dd, J = 1.4, 7.7 Hz, 1H), 7.81 (d, J = 0.5 Hz, 1H), 7.68 (br s, 1H), 7.43-7.15 (m, 4H), 7.13-6.81 (m, 1H), 5.72 (br s, 1H), 3.63 (q, J = 7.0 Hz, 4H), 1.18 (t, J = 7.0 Hz, 6H) |
| 25 | 272.1 | 2.89 | |
| 26 | 269.1 | 3.32 | |
| 27 | 268. | 2.81 | |
| 28 | 420. | 3.33 | |
| 29 | 354.1 | 3.32 | |
| 30 | 256.9 | 3.03 | |
| 31 | 272. | 2.83 | |
| 32 | 296.2 | 3.37 | |
| 33 | 300. | 2.9 | |
| 34 | 284.2 | 3.26 | 1H NMR (300 MHz, CDCl$_3$) δ 8.13 (m, 2H), 7.72 (s, 2H), 7.46 (m, 3H), 5.60 (s, 1H), 3.70 (m, 2H), 3.63 (m, 2H), 1.72 (m, 4H), 1.26 (t, J = 7.2 Hz, 3H), 0.98 (t, J = 7.2 Hz, 3H). |
| 35 | 328.2 | 3.04 | |
| 36 | 310.2 | 3.45 | |
| 37 | 372. | 3.59 | |
| 38 | 332. | 3.25 | 1H-NMR (CDCl$_3$, 300 MHz) δ 8.14 (m, 2H), 7.74 (s, 1H), 7.67 (br s, 1H), 7.47 (m, 3H), 7.23 (m, 5H), 5.79 (br s, 1H), 3.95 (t, J = 6.9 Hz, 2H), 3.21 (s, 3H), 2.97 (t, J = 6.9 Hz, 2H). |
| 39 | 340.2 | 3.36 | |
| 40 | 310.2 | 3.38 | |
| 41 | 282.2 | 2.91 | |
| 42 | 408. | 2.99 | |
| 43 | 312. | 2.46 | |
| 44 | 340. | 2.73 | |
| 45 | 400. | 3.18 | |
| 46 | 280. | 3.14 | |
| 47 | 285.1 | 3.65 | |
| 48 | 284.1 | 2.58 | 1H NMR (300 MHz, CDCl$_3$) δ 7.79 (s, 1H), 7.65 (m, 3H), 7.37 (m, 1H), 7.02 (m, 1H), 5.97 (m, 2H), 5.46 (s, 1H), 5.28 (d, J = 15.6 Hz, 1H), 5.16 (d, J = 8.7 Hz, 1H), 4.16 (d, J = 5.7 Hz, 2H), 3.87 (s, 3H). |
| 49 | 390. | 2.96 | |
| 50 | 332. | 3.26 | |
| 51 | 271.1 | 3.23 | |
| 52 | 360.2 | 3.47 | |
| 53 | 356. | 3.41 | |
| 54 | 330. | 3.27 | |
| 55 | 312.2 | 3.47 | |
| 56 | 284.2 | 3.32 | |
| 57 | 266.3 | 2.71 | |
| 58 | 265.9 | 1.99 | |
| 59 | 354. | 3.05 | |
| 60 | 404. | 3.13 | |
| 61 | 284.2 | 3.25 | |
| 62 | 327.2 | 2.47 | |
| 63 | 371. | 3.11 | |
| 64 | 256.9 | 3.03 | |
| 65 | 342.2 | 3.07 | |
| 66 | 290.1 | 3.21 | |
| 67 | 288.1 | 3.27 | |
| 68 | 296. | 3.38 | |
| 69 | 294. | 3.15 | |
| 70 | 302.1 | 3.22 | |
| 71 | 271.3 | 3.15 | |
| 72 | 350.1 | 3.12 | 1H NMR (300 MHz, CDCl$_3$) δ 7.77 (d, J = 7.5 Hz, 1H), 7.67 (br s, 1H), 7.64-7.47 (m, 3H), 7.35 (s, 1H), 5.60 (br s, 1H), 3.96-3.77 (m, 4H), 1.73-1.52 (m, 6H) |
| 73 | 324. | 3.63 | |
| 74 | 300.2 | 3.08 | |
| 75 | 338.1 | 3.27 | |
| 76 | 342.2 | 3.4 | 1H NMR (300 MHz, CDCl$_3$) δ 7.88-7.73 (m, 3H), 7.29-7.11 (m, 1H), 6.92 (d, J = 8.4 Hz, 1H), 5.87 (br s, 1H), 3.87 (s, 3H), 3.70 (q, J = 6.9 Hz, 4H), 2.92 (heptet, J = 6.8 Hz, 1H), 1.25 (app t, J = 6.9 Hz, 12H) |
| 77 | 272.1 | 2.69 | |
| 78 | 326. | 3.32 | |
| 79 | 266. | 2.91 | |
| 80 | 328.1 | 2.45 | |

TABLE 2-continued

| Compd No. | LC-MS M + 1 | LC-RT min | NMR |
|---|---|---|---|
| 81 | 326.1 | 3.4 | |
| 82 | 330.2 | 2.85 | 1H NMR (300 MHz, CDCl₃) δ 7.79-7.72 (m, 3H), 7.66 (s, 1H), 6.95 (d, J = 8.1 Hz, 1H), 5.71 (br s, 1H), 3.97 (s, 3H), 3.94 (s, 3H), 3.72 (q, J = 7.0 Hz, 4H), 1.27 (t, J = 7.0 Hz, 6H) |
| 83 | 267. | 2.29 | |
| 84 | 354.1 | 3.32 | |
| 85 | 356.2 | 3.31 | |
| 86 | 310. | 3.43 | |
| 87 | 310. | 3.42 | 1H-NMR (CDCl₃, 300 MHz) δ 8.11 (m, 2H), 7.72 (s, 1H), 7.71 (br s, 1H), 7.45 (m, 3H), 5.77 (br s, 1H), 3.69 (t, J = 7.2 Hz, 2H), 3.60 (d, J = 6.3 Hz, 2H), 1.71 (m, 2H), 1.20 (m, 1H), 0.97 (t, J = 7.2 Hz, 3H), 0.54 (m, 2H), 0.33 (m, 2H). |
| 88 | 316.1 | 2.44 | 1H NMR (300 MHz, CDCl₃) δ 7.76 (m, 1H), 7.65 (m, 2H), 7.36 (m, J = 8.1 Hz 1H), 7.00 (d, J = 7.5 Hz 1H), 6.04 (s, 1H), 5.62 (s, 1H), 3.87 (s, 3H), 3.62 (m, 2H), 3.53 (d, J = 6.0 Hz, 2H), 3.36 (s, 3H), 1.96 (m, 2H). |
| 89 | 340.2 | 3.31 | |
| 90 | 332. | 2.01 | |
| 91 | 298.9 | 3.92 | |
| 92 | 394. | 3.34 | 1H-NMR (CDCl₃, 300 MHz) δ 8.11 (m, 2H), 7.83 (s, 1H), 7.49 (br s, 1H), 7.43 (m, 3H), 7.29 (m, 10H), 5.58 (br s, 1H), 5.04 (br s, 2H), 4.89 (br s, 2H) |
| 93 | 318. | 3.27 | |
| 94 | 288.1 | 3.39 | |
| 95 | 350.1 | 3.3 | |
| 96 | 442. | 3.11 | 1H-NMR (CDCl₃, 300 MHz) δ 8.13 (m, 2H), 7.78 (s, 1H), 7.76 (s, 1H), 7.67 (m, 2H), 7.47 (m, 5H), 5.85 (br s, 1H), 4.91 (d, J = 12.6 Hz, 2H), 3.51 (m, 2H), 2.14 (m, 2H), 2.07 (br s, 1H), 1.89 (d, J = 12.6 Hz, 2H). |
| 97 | 360.9 | 4.2 | |
| 98 | 304.1 | 3.3 | |
| 99 | 354. | 3.01 | |
| 100 | 300.2 | 2.53 | |
| 101 | 348. | 2.73 | 1H-NMR (CDCl₃, 300 MHz) δ 8.12 (m, 2H), 7.79 (s, 1H), 7.64 (br s, 1H), 7.48 (m, 3H), 7.30 (m, 5H), 5.85 (br s, 1H), 5.16 (t, J = 5.7 Hz, 1H), 3.98 (d, J = 5.7 Hz, 2H), 3.17 (s, 3H). |
| 102 | 272. | 2.61 | |
| 103 | 242.1 | 2.47 | 1H-NMR (CDCl₃, 300 MHz) δ 8.09 (m, 2H), 7.91 (br s 1H), 7.80 (s, 1H), 7.46 (m, 3H), 5.23 (br s, 1H), 3.09 (d, J = 5.1 Hz, 3H), 3.03 (d, J = 5.1 Hz, 3H). |
| 104 | 355. | 4.05 | 1H NMR (300 MHz, CDCl₃) δ 8.14 (m, 1H), 7.72 (m, 2H), 7.43 (m, 3H), 5.59 (s, 1H), 3.63 (m, 4H), 1.57 (m, 6H), 0.99 (d, J = 6.6 Hz, 12H). |
| 105 | 330.1 | 3.06 | |
| 106 | 350.1 | 3.4 | |
| 107 | 306.1 | 3.11 | |
| 108 | 330.2 | 2.77 | 1H NMR (300 MHz, CDCl₃) δ 7.79 (br s, 1H), 7.30 (t, J = 8.3 Hz, 1H), 7.26 (s, 1H), 6.61 (d, J = 8.3 Hz, 2H), 6.16 (br s, 1H), 3.74 (s, 6H), 3.66 (q, J = 6.9 Hz, 4H), 1.22 (t, J = 6.9 Hz, 6H) |
| 109 | 300. | 3.17 | |
| 110 | 300. | 3.12 | |
| 111 | 307.1 | 2.97 | |
| 112 | 282.9 | 3.3 | |
| 113 | 310. | 3.44 | |
| 114 | 296.2 | 3.33 | |
| 115 | 346.1 | 3.3 | |
| 116 | 298.2 | 3.55 | |
| 117 | 298.9 | 3.51 | |
| 118 | 312. | 3.55 | |
| 119 | 271.1 | 3.48 | H NMR (400 MHz, DMSO-d6) δ 8.16 (m, 2H), 8.06 (s, 1H), 7.80 (s, 1H), 7.58 (s, 1H), 7.55 (m, 3H), 3.75 (q, J = 6.9 Hz, 4H), 1.19 (t, J = 6.5 Hz, 6H) |
| 120 | 298.2 | 3.37 | |
| 121 | 298.2 | 3.4 | |
| 122 | 300.1 | 3.34 | |
| 123 | 316.1 | 1.53 | |
| 124 | 342.2 | 3.02 | |
| 125 | 306.1 | 2.95 | |
| 126 | 305.3 | 3.23 | |
| 127 | 326.2 | 3.22 | |
| 128 | 322. | 2.75 | |
| 129 | 310. | 3.09 | |
| 130 | 307.1 | 2.98 | |
| 131 | 302.2 | 3.44 | |
| 132 | 405.1 | 3.28 | |
| 133 | 318.1 | 3.09 | |
| 134 | 312. | 2.86 | |
| 135 | 310. | 3.07 | |
| 136 | 296.9 | 3.43 | |
| 137 | 330.1 | 3.14 | |
| 138 | 272.1 | 2.5 | |
| 139 | 414. | 2.6 | |
| 140 | 350.1 | 3.57 | |
| 141 | 327.1 | 3.9 | H NMR (400 MHz, DMSO-d6) δ 8.17 (m, 2H), 7.53 (m, 3H), 7.18 (s, 1H), 3.67 (s, 4H), 3.45 (m, 2H), 3.28 (q, J = 7.0 Hz, 2H), 1.16 (m, 12H) |
| 142 | 312. | 3.2 | |
| 143 | 388. | 2.93 | 1H-NMR (CDCl₃, 300 MHz) δ 8.10 (m, 2H), 7.72 (s, 1H), 7.67 (br d, J = 3.6 Hz, 1H), 7.46 (m, 3H), 7.27 (m, 5H), 5.83 (br d, J = 3.6 Hz, 1H), 5.65 (d, J = 13.2 Hz, 2H), 3.41 (m, 2H), 2.80 (s, 2H), 1.10 (m, 4H). |
| 144 | 338.1 | 3.34 | |
| 145 | 282.1 | 2.42 | |
| 146 | 374.2 | 3.36 | |
| 147 | 304.1 | 3.31 | |
| 148 | 336. | 3.67 | |
| 149 | 296.2 | 3.27 | |
| 150 | 338. | 3.47 | |
| 151 | 306.1 | 3.53 | 1H NMR (300 MHz, CDCl₃) δ 7.70-7.60 (m, 2H), 7.63 (s, 1H), 6.91 (app t, J = 8.3 Hz, 1H), 5.57 (br s, 1H), 3.72 (q, J = 7.0 Hz, 4H), 1.26 (t, J = 7.0 Hz, 6H) |
| 152 | 366.1 | 3.23 | |
| 153 | 294.1 | 3.2 | |
| 154 | 252. | 2.5 | 1H-NMR (CDCl₃, 300 MHz) δ 8.11 (m, 2H), 7.88 (s, 1H), 7.71 (br s, 1H), 7.47 (m, 3H), 5.83 (br s, 1H), 5.47 (br s, 1H), 4.32 (m, 2H), 2.24 (t, J = 2.7 Hz, 1H). |
| 155 | 362.1 | 2.7 | |
| 156 | 300.2 | 2.55 | |
| 157 | 338.7 | 3.94 | |
| 158 | 300.2 | 3.16 | 1H NMR (300 MHz, CDCl₃) δ 8.03 (s, 1H), 7.99 (dt, J = 6.5, 2.1 Hz, 1H), 7.02 (s, 1H), 4.76 (s, 2H), 4.67 (heptet, J = 6.9 Hz, 1H), 3.69 (q, J = 7.0 Hz, 4H), 3.43 (q, J = 7.4 Hz, 2H), 1.31 t, J = 6.1 Hz, 3H), 1.26-1.14 (m, 6H), 1.22 (d, J = 6.9 Hz, 6H) |
| 159 | 284.2 | 3.23 | |
| 160 | 288.1 | 3.27 | |
| 161 | 326.2 | 3.25 | |
| 162 | 308.1 | 2.94 | |

TABLE 2-continued

| Compd No. | LC-MS M + 1 | LC-RT min | NMR |
|---|---|---|---|
| 163 | 306.1 | 3.13 | |
| 164 | 319.3 | 3.57 | |
| 165 | 296.2 | 3.28 | |
| 166 | 324.2 | 3.52 | |
| 167 | 284.1 | 2.54 | |
| 168 | 312.2 | 3.1 | |
| 169 | 286. | 2.85 | |
| 170 | 338.1 | 3.42 | |
| 171 | 327.3 | 4.24 | |
| 172 | 330.2 | 3.01 | |
| 173 | 324.1 | 2.61 | |
| 174 | 332.2 | 2.74 | |
| 175 | 314.2 | 3.48 | |
| 176 | 324. | 2.6 | |
| 177 | 381. | 2.69 | |
| 178 | 284. | 2.61 | |
| 179 | 229.1 | 2.58 | |
| 180 | 383. | 3.15 | |
| 181 | 326. | 2.48 | 1H-NMR (CDCl₃, 300 MHz) δ 8.11 (m, 2H), 7.71 (s, 1H), 7.69 (br s, 1H), 7.45 (m, 3H), 5.82 (br s, 1H), 4.89 (d, J = 13.2 Hz, 2H), 3.75 (t, J = 6.6 Hz, 2H), 2.96 (m, 2H), 1.84 (d, J = 12.0 Hz, 2H), 1.75 (m, 1H), 1.57 (q, J = 6.3 Hz, 2H), 1.27 (m, 2H). |
| 182 | 366.1 | 3.37 | |
| 183 | 254.9 | 2.98 | |
| 184 | 326.2 | 3.63 | |
| 185 | 350.1 | 3.32 | 1H NMR (300 MHz, CDCl₃) δ 8.37 (br s, 1H), 8.30 (d, J = 7.6 Hz, 1H), 7.77-7.64 (m, 3H), 7.59 (t, J = 7.9 Hz, 1H), 5.62 (br s, 1H), 3.95-3.85 (m, 4H), 1.77-1.60 (m, 6H) |
| 186 | 298.2 | 3.41 | |
| 187 | 433.3 | 3.57 | |
| 188 | 296. | 3.25 | |
| 189 | 298.1 | 2.76 | |
| 190 | 358.2 | 3.01 | |
| 191 | 244.1 | 1.98 | |
| 192 | 300.1 | 3.44 | |
| 193 | 328. | 2.48 | |
| 194 | 326.2 | 3.26 | |
| 195 | 454.1 | 3.37 | |
| 196 | 326. | 3.62 | |
| 197 | 340. | 3.38 | |
| 198 | 326.2 | 3.26 | |
| 199 | 350.1 | 3.65 | |
| 200 | 338.1 | 3.51 | |
| 201 | 312.2 | 3.59 | |
| 202 | 350.1 | 3.36 | |
| 203 | 298.1 | 2.74 | |
| 204 | 266. | 2.72 | |
| 205 | 312. | 3.17 | |
| 206 | 298. | 3.41 | |
| 207 | 298.2 | 3.18 | |
| 208 | 272. | 2.77 | |
| 209 | 314. | 2.71 | |
| 210 | 338.1 | 3.23 | |
| 211 | 314.1 | 2.51 | |
| 212 | 314.2 | 3.21 | |
| 213 | 366.1 | 3.35 | |
| 214 | 326.1 | 3.3 | |
| 215 | 243.1 | 2.81 | 1H-NMR (CDCl₃, 300 MHz) δ 8.09 (m, 2H), 7.78 (s, 1H), 7.71 (br s, 1H), 7.47 (m, 3H), 5.72 (br s, 1H), 5.25 (br s, 1H), 3.55 (m, 2H), 1.30 (t, J = 7.5 Hz, 3H). |
| 216 | 294. | 2.67 | |
| 217 | 330.2 | 2.98 | 1H NMR (300 MHz, CDCl₃) δ 7.89 (s, 1H), 7.76 (br s, 1H), 7.56 (d, J = 2.8 Hz, 1H), 6.98-6.89 (m, 3H), 5.83 (br s, 1H), 3.85 (s, 3H), 3.82 (s, 3H), 3.69 (q, J = 7.0 Hz, 4), 1.24 (t, J = 7.0 Hz, 6H) |
| 218 | 347. | 2.82 | |
| 219 | 318.1 | 3.57 | |
| 220 | 284. | 2.68 | |
| 221 | 296.2 | 3.47 | |
| 222 | 310. | 3.28 | |
| 223 | 328.2 | 2.97 | |
| 224 | 354.2 | 3.4 | |
| 225 | 338.1 | 3.29 | |
| 226 | 338.1 | 3.57 | |
| 227 | 326.1 | 3.04 | |
| 228 | 316. | 2.45 | |
| 229 | 301.2 | 2.93 | |
| 230 | 284.2 | 3.43 | |
| 231 | 258.1 | 2.31 | |
| 232 | 296.2 | 3.33 | |
| 233 | 338.1 | 3.31 | |

VI. Assays

Assays for Detecting and Measuring ☐F508-CFTR Correction Properties of Compounds A. Membrane Potential Optical Methods for Assaying ☐F508-CFTR Modulation Properties of Compounds The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

1. Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ☐F508-CFTR. The cells were subsequently rinsed 3× with Krebs Ringers solution and loaded with the voltage-sensitive dyes. To activate ΔF508-CFTR, 10 μM forskolin and the CFTR potentiator, genistein (20 μM), were added along with Cl⁻-free medium to each well. The addition of Cl⁻-free medium promoted Cl⁻ efflux in response to ΔF508-CFTR activation and the resulting membrane depolarization was optically monitored using the FRET-based voltage-sensor dyes.

2. Identification of Potentiator Compounds

To identify potentiators of ΔF508-CFTR, a double-addition HTS assay format was developed. During the first addition, a Cl⁻-free medium with or without test compound was added to each well. After 22 sec, a second addition of Cl⁻-free medium containing 2-10 μM forskolin was added to activate ΔF508-CFTR. The extracellular Cl⁻ concentration following both additions was 28 mM, which promoted Cl⁻ efflux in response to ΔF508-CFTR activation and the resulting membrane depolarization was optically monitored using the FRET-based voltage-sensor dyes.

3. Solutions

Bath Solution #1: (in mM) NaCl 160, KCl 4.5, $CaCl_2$ 2, $MgCl_2$ 1, HEPES 10, pH 7.4 with NaOH.

Chloride-free bath solution: Chloride salts in Bath Solution #1 are substituted with gluconate salts.

CC2-DMPE: Prepared as a 10 mM stock solution in DMSO and stored at −20° C.

$DiSBAC_2(3)$: Prepared as a 10 mM stock in DMSO and stored at −20° C.

4. Cell Culture

NIH3T3 mouse fibroblasts stably expressing ΔF508-CFTR are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1× NEAA, β-ME, 1× pen/strep, and 25 mM HEPES in 175 cm² culture flasks. For all optical assays, the cells were seeded at 30,000/well in 384-well matrigel-coated plates and cultured for 2 hrs at 37° C. before culturing at 27° C. for 24 hrs for the potentiator assay. For the correction assays, the cells are cultured at 27° C. or 37° C. with and without compounds for 16-24 hoursB.

Electrophysiological Assays for Assaying ΔF508-CFTR Modulation Properties of Compounds

1. Using Chamber Assay

Using chamber experiments were performed on polarized epithelial cells expressing ΔF508-CFTR to further characterize the ΔF508-CFTR modulators identified in the optical assays. $FRT^{\Delta F508\text{-}CFTR}$ epithelial cells grown on Costar Snapwell cell culture inserts were mounted in an Ussing chamber (Physiologic Instruments, Inc., San Diego, Calif.), and the monolayers were continuously short-circuited using a Voltage-clamp System (Department of Bioengineering, University of Iowa, Iowa, and, Physiologic Instruments, Inc., San Diego, Calif.). Transepithelial resistance was measured by applying a 2-mV pulse. Under these conditions, the FRT epithelia demonstrated resistances of 4 KΩ/cm² or more. The solutions were maintained at 27° C. and bubbled with air. The electrode offset potential and fluid resistance were corrected using a cell-free insert. Under these conditions, the current reflects the flow of Cl⁻ through ΔF508-CFTR expressed in the apical membrane. The $I_{SC}$ was digitally acquired using an MP100A-CE interface and AcqKnowledge software (v3.2.6; BIOPAC Systems, Santa Barbara, Calif.).

2. Identification of Correction Compounds

Typical protocol utilized a basolateral to apical membrane Cl⁻ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

3. Identification of potentiator Compounds

Typical protocol utilized a basolateral to apical membrane Cl⁻ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl⁻ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

4. Solutions

Basolateral solution (in mM): NaCl (135), $CaCl_2$ (1.2), $MgCl_2$ (1.2), $K_2HPO_4$ (2.4), $KHPO_4$ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

5. Cell Culture

Fisher rat epithelial (FRT) cells expressing ΔF508-CFTR ($FRT^{\Delta F508\text{-}CFTR}$) were used for Ussing chamber experiments for the putative ΔF508-CFTR modulators identified from our optical assays. The cells were cultured on Costar Snapwell cell culture inserts and cultured for five days at 37° C. and 5% $CO_2$ in Coon's modified Ham's F-12 medium supplemented with 5% fetal calf serum, 100 U/ml penicillin, and 100 μg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

6. Whole-Cell Recordings

The macroscopic ☐F508-CFTR current ($I_{\square F508}$) in temperature- and test compound-corrected NIH3T3 cells stably expressing ☐F508-CFTR were monitored using the perforated-patch, whole-cell recording. Briefly, voltage-clamp recordings of $I_{\square F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 M Ω when filled with the intracellular solution. Under these recording conditions, the calculated reversal potential for Cl⁻ ($E_{Cl}$) at room temperature was −28 mV. All recordings had a seal resistance >20 G Ω and a series resistance <15 M Ω. Pulse generation, data acquisition, and analysis were performed using a PC equipped with a Digidata 1320 A/D interface in conjunction with Clampex 8 (Axon Instruments Inc.). The bath contained <250 ☐l of saline and was continuously perifused at a rate of 2 ml/min using a gravity-driven perfusion system.

7. Identification of Correction Compounds

To determine the activity of correction compounds for increasing the density of functional ☐F508-CFTR in the plasma membrane, we used the above-described perforated-patch-recording techniques to measure the current density following 24-hr treatment with the correction compounds. To fully activate ☐F508-CFTR, 10 ☐M forskolin and 20 ☐M genistein were added to the cells. Under our recording conditions, the current density following 24-hr incubation at 27° C. was higher than that observed following 24-hr incubation at 37° C. These results are consistent with the known effects of low-temperature incubation on the density of ☐F508-CFTR in the plasma membrane. To determine the effects of correction compounds on CFTR current density, the cells were incubated with 10 ☐M of the test compound for 24 hours at 37° C. and the current density was compared to the 27° C. and 37° C. controls (% activity). Prior to recording, the cells were washed 3× with extracellular recording medium to remove any remaining test compound. Preincubation with 10 ☐M of correction compounds significantly increased the cAMP- and genistein-dependent current compared to the 37° C. controls.

8. Identification of Potentiator Compounds

The ability of ☐F508-CFTR potentiators to increase the macroscopic ☐F508-CFTR Cl⁻ current ($I_{\square F508}$) in NIH3T3 cells stably expressing ☐F508-CFTR was also investigated using perforated-patch-recording techniques. The potentiators identified from the optical assays evoked a dose-dependent increase in $I_{\square F508}$ with similar potency and efficacy observed in the optical assays. In all cells examined, the reversal potential before and during potentiator application was around −30 mV, which is the calculated $E_{Cl}$ (−28 mV).

9. Solutions

Intracellular solution (in mM): Cs-aspartate (90), CsCl (50), MgCl₂ (1), HEPES (10), and 240 ☐g/ml amphotericin-B (pH adjusted to 7.35 with CsOH).

Extracellular solution (in mM): N-methyl-D-glucamine (NMDG)-Cl (150), MgCl₂ (2), CaCl₂ (2), HEPES (10) (pH adjusted to 7.35 with HCl).

10. Cell Culture

NIH3T3 mouse fibroblasts stably expressing ☐F508-CFTR are used for whole-cell recordings. The cells are maintained at 37° C. in 5% CO₂ and 90% humidity in Dulbecco's modified Eagle's medium supplemented with 2 mM glutamine, 10% fetal bovine serum, 1× NEAA, ☐ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

11. Single-channel recordings

The single-channel activities of temperature-corrected ☐F508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 M Ω when filled with the extracellular solution. The ☐F508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ☐F508-CFTR activity during the rapid perifusion, the non-specific phosphatase inhibitor F⁻ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≤2 active channels. The maximum number of simultaneous openings determined the number of active channels during the course of an experiment. To determine the single-channel current amplitude, the data recorded from 120 sec of ☐F508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o = I/i(N)$, where I=mean current, i=single-channel current amplitude, and N=number of active channels in patch.

12. Solutions

Extracellular solution (in mM): NMDG (150), aspartic acid (150), CaCl₂ (5), MgCl₂ (2), and HEPES (10) (pH adjusted to 7.35 with Tris base).

Intracellular solution (in mM): NMDG-Cl (150), MgCl₂ (2), EGTA (5), TES (10), and Tris base (14) (pH adjusted to 7.35 with HCl).

13. Cell Culture

NIH3T3 mouse fibroblasts stably expressing ΔF508-CFTR are used for excised-membrane patch-clamp recordings. The cells are maintained at 37° C. in 5% $CO_2$ and 90% humidity in Dulbecco's modified Eagle's medium supplemented with 2 mM glutamine, 10% fetal bovine serum, 1× NEAA, β-ME, 1× pen/strep, and 25 mM HEPES in 175 $cm^2$ culture flasks. For single channel recordings, 2,500-5,000 cells were seeded on poly-L-lysine-coated glass coverslips and cultured for 24-48 hrs at 27° C. before use.

Table 3 contains the assay results for the compounds in Table 1. The potency ranges in Table 3 were determined are as follows: +++ corresponds to EC50 potencies less than 1.0 μM, ++ corresponds to EC50 potencies between 1.0 μM and 5.0 μM, and + corresponds to EC50 potencies greater than 5.0 μM. The efficacy ranges in Table 3 were determined as follows: +++ corresponds to Efficacy greater than 100, ++ corresponds to Efficacy between 100 and 50, and + corresponds to Efficacy less than 50.

TABLE 3

| Compd No. | EC50 | Efficacy |
|---|---|---|
| 1 | + | ++ |
| 2 | + | ++ |
| 3 | + | ++ |
| 4 | + | +++ |
| 5 | +++ | +++ |
| 6 | ++ | ++ |
| 7 | ++ | +++ |
| 8 | ++ | ++ |
| 9 | + | ++ |
| 10 | + | ++ |
| 11 | ++ | ++ |
| 12 | +++ | ++ |
| 13 | + | ++ |
| 14 | ++ | +++ |
| 15 | + | ++ |
| 16 | ++ | ++ |
| 17 | ++ | ++ |
| 18 | + | ++ |
| 19 | ++ | ++ |
| 20 | +++ | ++ |
| 21 | ++ | +++ |
| 22 | + | ++ |
| 23 | ++ | ++ |
| 24 | +++ | ++ |
| 25 | + | + |
| 26 | ++ | ++ |
| 27 | + | ++ |
| 28 | + | ++ |
| 29 | +++ | ++ |
| 30 | + | ++ |
| 31 | + | + |
| 32 | + | ++ |
| 33 | ++ | +++ |
| 34 | ++ | +++ |
| 35 | +++ | +++ |
| 36 | ++ | + |
| 37 | + | ++ |
| 38 | ++ | +++ |
| 39 | + | +++ |
| 40 | + | ++ |
| 41 | + | + |
| 42 | + | + |
| 43 | + | + |
| 44 | + | ++ |
| 45 | ++ | ++ |
| 46 | ++ | +++ |
| 47 | ++ | +++ |
| 48 | + | ++ |
| 49 | + | ++ |
| 50 | +++ | +++ |
| 51 | + | ++ |
| 52 | ++ | ++ |
| 53 | + | ++ |
| 54 | ++ | ++ |
| 55 | +++ | ++ |
| 56 | ++ | +++ |
| 57 | + | + |
| 58 | + | + |
| 59 | ++ | + |
| 60 | + | ++ |
| 61 | ++ | ++ |
| 62 | + | ++ |
| 63 | ++ | ++ |
| 64 | + | ++ |
| 65 | + | ++ |
| 66 | +++ | +++ |
| 67 | ++ | +++ |
| 68 | ++ | ++ |
| 69 | ++ | +++ |
| 70 | ++ | + |
| 71 | + | ++ |
| 72 | ++ | ++ |
| 73 | ++ | + |
| 74 | ++ | +++ |
| 75 | +++ | ++ |
| 76 | +++ | +++ |
| 77 | + | + |
| 78 | ++ | ++ |
| 79 | ++ | +++ |
| 80 | + | + |
| 81 | ++ | +++ |
| 82 | +++ | ++ |
| 83 | + | + |
| 84 | +++ | ++ |
| 85 | +++ | ++ |
| 86 | +++ | ++ |
| 87 | ++ | ++ |
| 88 | + | + |
| 89 | ++ | +++ |
| 90 | + | + |
| 91 | ++ | +++ |
| 92 | ++ | ++ |
| 93 | + | ++ |
| 94 | ++ | +++ |
| 95 | ++ | ++ |
| 96 | + | ++ |
| 97 | + | ++ |
| 98 | +++ | +++ |
| 99 | ++ | + |
| 100 | ++ | ++ |
| 101 | + | +++ |
| 102 | + | ++ |
| 103 | +++ | + |
| 104 | ++ | + |
| 105 | + | +++ |
| 106 | ++ | +++ |
| 107 | +++ | ++ |
| 108 | + | ++ |
| 109 | +++ | +++ |
| 110 | +++ | +++ |
| 111 | + | ++ |
| 112 | + | + |
| 113 | ++ | ++ |
| 114 | ++ | +++ |
| 115 | ++ | ++ |
| 116 | ++ | +++ |
| 117 | + | +++ |
| 118 | +++ | ++ |
| 119 | +++ | +++ |
| 120 | +++ | ++ |
| 121 | ++ | +++ |
| 122 | + | +++ |
| 123 | + | + |
| 124 | ++ | +++ |
| 125 | +++ | ++ |
| 126 | + | ++ |
| 127 | ++ | ++ |
| 128 | + | + |

TABLE 3-continued

| Compd No. | EC50 | Efficacy |
|---|---|---|
| 129 | + | ++ |
| 130 | + | + |
| 131 | ++ | +++ |
| 132 | + | +++ |
| 133 | +++ | ++ |
| 134 | + | ++ |
| 135 | + | ++ |
| 136 | + | ++ |
| 137 | ++ | ++ |
| 138 | + | ++ |
| 139 | + | ++ |
| 140 | ++ | ++ |
| 141 | ++ | ++ |
| 142 | + | ++ |
| 143 | + | + |
| 144 | + | ++ |
| 145 | + | ++ |
| 146 | ++ | +++ |
| 147 | +++ | ++ |
| 148 | ++ | ++ |
| 149 | + | ++ |
| 150 | ++ | ++ |
| 151 | ++ | +++ |
| 152 | ++ | ++ |
| 153 | + | ++ |
| 154 | + | + |
| 155 | + | ++ |
| 156 | + | + |
| 157 | + | + |
| 158 | + | ++ |
| 159 | ++ | +++ |
| 160 | + | ++ |
| 161 | ++ | +++ |
| 162 | ++ | ++ |
| 163 | +++ | ++ |
| 164 | ++ | ++ |
| 165 | + | +++ |
| 166 | + | + |
| 167 | + | ++ |
| 168 | + | +++ |
| 169 | + | +++ |
| 170 | ++ | + |
| 171 | +++ | ++ |
| 172 | ++ | +++ |
| 173 | + | ++ |
| 174 | + | ++ |
| 175 | + | ++ |
| 176 | + | ++ |
| 177 | + | ++ |
| 178 | ++ | +++ |
| 179 | + | + |
| 180 | + | ++ |
| 181 | + | ++ |
| 182 | ++ | + |
| 183 | + | ++ |
| 184 | +++ | ++ |
| 185 | + | + |
| 186 | ++ | +++ |
| 187 | ++ | ++ |
| 188 | +++ | +++ |
| 189 | + | + |
| 190 | +++ | ++ |
| 191 | + | + |
| 192 | ++ | ++ |
| 193 | ++ | +++ |
| 194 | ++ | +++ |
| 195 | + | ++ |
| 196 | ++ | + |
| 197 | ++ | ++ |
| 198 | ++ | + |
| 199 | ++ | ++ |
| 200 | +++ | ++ |
| 201 | ++ | +++ |
| 202 | ++ | ++ |
| 203 | + | +++ |
| 204 | ++ | ++ |
| 205 | + | ++ |
| 206 | ++ | ++ |
| 207 | ++ | +++ |
| 208 | + | + |
| 209 | ++ | ++ |
| 210 | +++ | ++ |
| 211 | + | ++ |
| 212 | +++ | +++ |
| 213 | ++ | + |
| 214 | +++ | ++ |
| 215 | + | ++ |
| 216 | + | ++ |
| 217 | +++ | ++ |
| 218 | ++ | +++ |
| 219 | ++ | + |
| 220 | + | + |
| 221 | ++ | + |
| 222 | + | ++ |
| 223 | ++ | +++ |
| 224 | + | + |
| 225 | +++ | +++ |
| 226 | ++ | ++ |
| 227 | + | ++ |
| 228 | + | ++ |
| 229 | ++ | ++ |
| 230 | ++ | +++ |
| 231 | + | ++ |
| 232 | ++ | + |
| 233 | +++ | ++ |

VII. Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:
1. A compound of the formula:

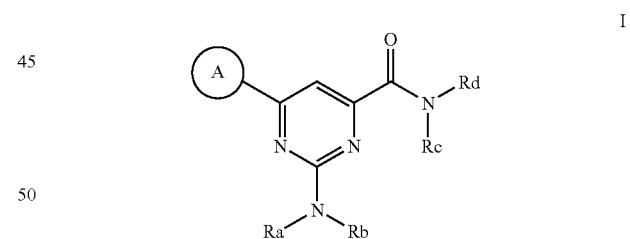

wherein
Ra and Rb are each independently an optionally substituted hydroxyalkyl, an optionally substituted alkyloxyalkyl, an optionally substituted (heterocycloalkyl)alkyl, an optionally substituted (cycloalkyl)alkyl, an optionally substituted alkyloxycarbonylalkyl, an optionally substituted alkenyl, an optionally substituted alkenyl, an optionally substituted aralkyl or an optionally substituted heteroaralkyl;
or Ra and Rb together with the nitrogen atom to which they are bound form an optionally substituted heterocycloaliphatic, or an optionally substituted heteroaryl;
Each Rc is independently H;
Each Rd is independently H;

Ring A is an aryl or heteroaryl, each optionally substituted with 1-4 Re;

Each Re is independently carboxy, amino, nitro, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, sulfonyl, sulfinyl, sulfanyl, sulfoxy, sulfamoyl, sulfamide, ketal, carbamoyl, cyano, halo, urea, thiourea, haloalkyl, or —Z—Rf, in which each alkyl, cycloalkyl, heterocycloalkyl, aryl, and heteroaryl portion of the Re substituents is optionally substituted with 1-3 of Rg, or two Re, on adjacent A ring atoms, together with the A ring atoms to which they are bound form a heterocycloaliphatic ring;

Each Z is absent, —O—, or —S—;

Each Rf is independently hydrogen, alkyl, carboxyalkyl, hydroxyalkyl, alkenyl, alkynyl, cycloalkyl, (cycloalkyl)alkyl, heterocycloalkyl, (heterocycloalkyl)alkyl, aryl, heteroaryl, aralkyl, heteroaralkyl, aroyl, heteroaroyl, alkoxycarbonyl, alkylcarbonyl, aminocarbonyl, or acyl, in which each alkyl, alkenyl, alkynyl, cycloalkyl, heterocycloalkyl, aryl, and heteroaryl portion of the Rf substituents is optionally substituted with 1-3 of Rg;

Each Rg is independently halo, cyano, alkoxy, hydroxyl, nitro, haloalkyl, and alkyl;

with the proviso that

Ring A is not 7-chloro-2-(4-fluorophenyl)pyrazolo[1,5-a]pyridine-3-yl or 7-cyclopentylamino-2-(4-fluorophenyl)pyrazolo[1,5-a]pyridine-3-yl.

2. The compound of claim 1, wherein Ring A is aryl optionally substituted with 1-4 of Re.

3. The compound of claim 2, wherein the aryl is optionally substituted with 1-4 of alkyl, hydroxyalkyl, haloalkyl, alkoxy, halo, hydroxy, alkoxycarbonyl, aryloxy, S(O)$_2$alkyl, cyano, alkylcarbonylamino, methylenedioxy, or acyl.

4. The compound of claim 3, wherein the aryl is phenyl.

5. The compound of claim 1, wherein Ring A is heteroaryl.

6. The compound of claim 5, wherein the heteroaryl is optionally substituted with 1-4 of alkyl, hydroxyalkyl, haloalkyl, alkoxy, halo, hydroxyl, alkoxycarbonyl, aryloxy, sulfoxy, or acyl.

7. The compound of claim 6, wherein Ring A is thiophene, pyrimidinyl, benzothiophene, or pyridinyl, furanyl.

8. The compound of claim 1, wherein Ra and Rb together form an optionally substituted heterocycloaliphatic or an optionally substituted heteroaryl.

9. The compound of claim 8, wherein Ra and Rb together form an optionally substituted heterocycloaliphatic.

10. The compound of claim 9, wherein Ra and Rb form an optionally substituted heterocycloalkyl.

11. The compound of claim 10, wherein the heterocycloalkyl is optionally substituted with 1-3 of halo, haloalkyl, alkyl, alkyloxycarbonyl, alkylcarbonyl, hydroxyalkyl, sulfonyl, sulfinyl, aminocarbonyl, cyano, sulfoxy, acetal, ketal, an optionally substituted aryl, an optionally substituted alkoxy, an optionally substituted aralkyl, an optionally aroyl, or an optionally substituted heteroaryl.

12. The compound of claim 11, wherein the heterocycloalkyl is a piperidine, piperazine, morpholino, thiomorpholino, tetrahydropyridinyl, decahydroisoquinolinyl, pyrrolidinyl, thiazolidinyl, or azetidinyl ring, in which each ring is optionally substituted with 1-3 of halo, haloalkyl, alkyl, alkyloxycarbonyl, alkylcarbonyl, hydroxyalkyl, sulfonyl, sulfinyl, aminocarbonyl, cyano, sulfoxy, acetal, ketal, an optionally substituted aryl, an optionally substituted alkoxy, an optionally substituted aralkyl, an optionally aroyl, or an optionally substituted heteroaryl.

13. The compound of claim 9, wherein Ra and Rb form an optionally substituted heteroaryl.

14. The compound of claim 13, wherein the heteroaryl is optionally substituted with 1-3 of halo, haloalkyl, alkyl, alkyloxycarbonyl, alkylcarbonyl, hydroxyalkyl, sulfonyl, sulfinyl, aminocarbonyl, cyano, sulfoxy, acetal, ketal, an optionally substituted aryl, an optionally substituted alkoxy, an optionally substituted aralkyl, an optionally aroyl, or an optionally substituted heteroaryl.

15. The compound of claim 13, wherein the heteroaryl is a tetrahydroisoquinolinyl, perhydroisoquinoline, an imidazolyl, or a pyrazolyl ring, in which each ring is optionally substituted with 1-3 of halo, haloalkyl, alkyl, alkyloxycarbonyl, alkylcarbonyl, hydroxyalkyl, sulfonyl, sulfinyl, aminocarbonyl, cyano, sulfoxy, acetal, ketal, an optionally substituted aryl, an optionally substituted alkoxy, an optionally substituted aralkyl, an optionally aroyl, or an optionally substituted heteroaryl.

16. The compound of claim 1, wherein Ring A is substituted with at least one Re.

17. The compound of claim 16, wherein Ring A is substituted with one Re ortho relative to the attachment between Ring A and the pyrimidine.

18. The compound of claim 16, wherein Ring A is substituted with one Re meta relative to the attachment between Ring A and the pyrimidine.

19. The compound of claim 16, wherein Ring A is substituted with one Re para relative to the attachment between Ring A and the pyrimidine.

20. The compound of claim 1, wherein Ring A is substituted with two Re.

21. The compound of claim 20, wherein the two Re are ortho and meta relative to the attachment between Ring A and the pyrimidine.

22. A compound selected from:

2-azepan-1-yl-6-phenyl-pyrimidine-4-carboxamide 2-(4-acetyl-4-phenyl-1-piperidyl)-6-phenyl-pyrimidine-4-carboxamide 2-(4-methyl-1-piperidyl)-6-phenyl-pyrimidine-4-carboxamide 6-(3-methoxyphenyl)-2-morpholino-pyrimidine-4-carboxamide 2-(butyl-propyl-amino)-6-phenyl-pyrimidine-4-carboxamide 2-[4-(4-chlorophenyl)-4-hydroxy-1-piperidyl]-6-phenyl-pyrimidine-4-carboxamide 6-(3,5-dichlorophenyl)-2-(1-piperidyl)pyrimidine-4-carboxamide 2-diethylamino-6-(6-methoxy-3-pyridyl)-pyrimidine-4-carboxamide 2-diisobutylamino-6-phenyl-pyrimidine-4-carboxamide 6-(3-furyl)-2-(1-piperidyl)pyrimidine-4-carboxamide 2-(methyl-pentyl-amino)-6-phenyl-pyrimidine-4-carboxamide 6-(2,3-dichlorophenyl)-2-diethylamino-pyrimidine-4-carboxamide 3-(6-carbamoyl-2-diethylamino-pyrimidin-4-yl)benzoic acid isopropyl ester 6-(2,3-difluorophenyl)-2-(1-piperidyl)pyrimidine-4-carboxamide 2-(2,6-dimethylmorpholin-4-yl)-6-phenyl-pyrimidine-4-carboxamide 6-phenyl-2-pyrrolidin-1-yl-pyrimidine-4-carboxamide 6-(2,5-dimethoxyphenyl)-2-(1-piperidyl)pyrimidine-4-carboxamide 2-[4-hydroxy-4-[3-(trifluoromethyl)phenyl]-1-piperidyl]-6-phenyl-pyrimidine-4-carboxamide
6-(4-methoxyphenyl)-2-(1,2,3,6-tetrahydropyridin-1-yl)pyrimidine-4-carboxamide
6-(2,5-dichlorophenyl)-2-(1-piperidyl)pyrimidine-4-carboxamide
6-benzothiophen-3-yl-2-diethylamino-pyrimidine-4-carboxamide
2-diethylamino-6-(2,6-dimethoxyphenyl)-pyrimidine-4-carboxamide
2-diethylamino-6-(3-ethoxyphenyl)-pyrimidine-4-carboxamide
2-(allyl-methyl-amino)-6-phenyl-pyrimidine-4-carboxamide
2-(cyclopropylmethyl-propyl-amino)-6-(3-methoxyphenyl)-pyrimidine-4-carboxamide
2-dibenzylamino-6-phenyl-pyrimidine-4-carboxamide
2-(butyl-ethyl-amino)-6-phenyl-pyrimidine-4-carboxamide
6-(3-fluorophenyl)-2-(1-piperidyl)pyrimidine-4-carboxamide
2-diethylamino-6-(3,5-difluorophenyl)-pyrimidine-4-carboxamide
6-(5-isopropyl-2-methoxy-phenyl)-2-(1-piperidyl)pyrimidine-4-carboxamide
2-[(4-carbamoyl-6-phenyl-pyrimidin-2-yl)-methyl-amino]acetic acid ethyl ester
2-(ethyl-(2-hydroxyethyl)amino)-6-(3-methoxyphenyl)-pyrimidine-4-carboxamide
2-diethylamino-6-(2-fluorophenyl)-pyrimidine-4-carboxamide
2-(1-piperidyl)-6-[2-(trifluoromethyl)phenyl]-pyrimidine-4-carboxamide
2-[4-(4-methoxyphenyl)sulfonylpiperazin-1-yl]-6-phenyl-pyrimidine-4-carboxamide
6-(4-ethoxyphenyl)-2-(1-piperidyl)pyrimidine-4-carboxamide
2-cyclopentylamino-6-phenyl-pyrimidine-4-carboxamide
2-dipropylamino-6-phenyl-pyrimidine-4-carboxamide
6-(4-methoxyphenyl)-2-(1-piperidyl)pyrimidine-4-carboxamide
2-dimethylamino-6-phenyl-pyrimidine-4-carboxamide
2-diethylamino-6-(3-methoxyphenyl)-pyrimidine-4-carboxamide
2-diethylamino-6-(5-methyl-2-thienyl)-pyrimidine-4-carboxamide
2-diethylamino-6-(2-methoxyphenyl)-pyrimidine-4-carboxamide
2-(1-piperidyl)-6-(p-tolyl)pyrimidine-4-carboxamide
2-diethylamino-6-(5-fluoro-2-methoxy-phenyl)-pyrimidine-4-carboxamide
6-(3-methoxyphenyl)-2-(1,2,3,6-tetrahydropyridin-1-yl)pyrimidine-4-carboxamide
2-diethylamino-6-(4-isobutylphenyl)-pyrimidine-4-carboxamide
2-diethylamino-6-(5-isopropyl-2-methoxy-phenyl)-pyrimidine-4-carboxamide
6-phenyl-2-(4-phenyl-1,2,3,6-tetrahydropyridin-1-yl)-pyrimidine-4-carboxamide
2-diethylamino-6-(3,4-dimethylphenyl)-pyrimidine-4-carboxamide
2-diethylamino-6-phenyl-pyrimidine-4-carboxamide
6-(3-chlorophenyl)-2-diethylamino-pyrimidine-4-carboxamide
2-diethylamino-6-(3,4-dimethoxyphenyl)-pyrimidine-4-carboxamide
2-diethylamino-6-[3-(trifluoromethyl)phenyl]-pyrimidine-4-carboxamide
6-(3,4-dichlorophenyl)-2-diethylamino-pyrimidine-4-carboxamide
6-(2-methoxyphenyl)-2-(1-piperidyl)pyrimidine-4-carboxamide
6-phenyl-2-(1,2,3,4-tetrahydroisoquinolin-2-yl)pyrimidine-4-carboxamide
2-diethylamino-6-(m-tolyl)pyrimidine-4-carboxamide
6-phenyl-2-(1-piperidyl)pyrimidine-4-carboxamide
6-(5-chloro-2-methoxy-phenyl)-2-(1-piperidyl)pyrimidine-4-carboxamide
2-diethylamino-6-(2,5-dimethoxyphenyl)-pyrimidine-4-carboxamide
6-phenyl-2-(4-propyl-1-piperidyl)-pyrimidine-4-carboxamide
6-(4-isopropylphenyl)-2-(1-piperidyl)pyrimidine-4-carboxamide
2-dimethylamino-6-(3-methoxyphenyl)-pyrimidine-4-carboxamide
2-diethylamino-6-(4-fluoro-3-methyl-phenyl)-pyrimidine-4-carboxamide
2-diethylamino-6-(p-tolyl)pyrimidine-4-carboxamide
2-diethylamino-6-[3-(hydroxymethyl)phenyl]-pyrimidine-4-carboxamide
2-diethylamino-6-(4-ethylphenyl)-pyrimidine-4-carboxamide
2-(ethyl-(2-hydroxyethyl)amino)-6-(2-methoxyphenyl)-pyrimidine-4-carboxamide
6-phenyl-2-thiazolidin-3-yl-pyrimidine-4-carboxamide
2-(1,2,3,4,4a,5,6,7,8,8a-decahydroisoquinolin-2-yl)-6-phenyl-pyrimidine-4-carboxamide
6-(2-fluoro-3-methoxy-phenyl)-2-(1-piperidyl)pyrimidine-4-carboxamide
2-[4-(4-chlorophenyl)-1,2,3,6-tetrahydropyridin-1-yl]-6-phenyl-pyrimidine-4-carboxamide
2-diethylamino-6-(4-methoxyphenyl)-pyrimidine-4-carboxamide
2-diethylamino-6-(2-phenoxyphenyl)-pyrimidine-4-carboxamide
6-benzothiophen-3-yl-2-(1-piperidyl)pyrimidine-4-carboxamide
2-(cyclopropylmethyl-propyl-amino)-6-(2-methoxyphenyl)-pyrimidine-4-carboxamide
6-phenyl-2-(1,4-thiazinan-4-yl)pyrimidine-4-carboxamide
2-(1,4-dioxa-8-azaspiro[4.5]dec-8-yl)-6-phenyl-pyrimidine-4-carboxamide
2-(methyl-phenethyl-amino)-6-phenyl-pyrimidine-4-carboxamide
6-(2,3-dimethylphenyl)-2-(1-piperidyl)pyrimidine-4-carboxamide
2-(methyl-prop-2-ynyl-amino)-6-phenyl-pyrimidine-4-carboxamide
6-(2-fluorophenyl)-2-(1-piperidyl)pyrimidine-4-carboxamide
2-(2-furylmethyl-methyl-amino)-6-phenyl-pyrimidine-4-carboxamide
6-(2,5-dichlorophenyl)-2-diethylamino-pyrimidine-4-carboxamide
3-(6-carbamoyl-2-diethylamino-pyrimidin-4-yl)benzoic acid methyl ester
6-(3,5-difluorophenyl)-2-(1-piperidyl)pyrimidine-4-carboxamide
2-(1-piperidyl)-6-[4-(trifluoromethoxy)phenyl]-pyrimidine-4-carboxamide 2-(benzyl-ethyl-amino)-6-phenyl-pyrimidine-4-carboxamide
6-(2,4-dichlorophenyl)-2-(1-piperidyl)pyrimidine-4-carboxamide
6-(6-methoxy-3-pyridyl)-2-(1-piperidyl)pyrimidine-4-carboxamide
2-[ethyl-[2-(2-pyridyl)ethyl]amino]-6-phenyl-pyrimidine-4-carboxamide
2-(2-hydroxyethyl-propyl-amino)-6-phenyl-pyrimidine-4-carboxamide
2-morpholino-6-phenyl-pyrimidine-4-carboxamide
2-diethylamino-6-(2,4-dimethoxypyrimidin-5-yl)-pyrimidine-4-carboxamide
6-(2-ethoxyphenyl)-2-(1-piperidyl)pyrimidine-4-carboxamide
2-(4-cyano-4-phenyl-1-piperidyl)-6-phenyl-pyrimidine-4-carboxamide
2-[3-(diethylcarbamoyl)-1-piperidyl]-6-phenyl-pyrimidine-4-carboxamide
6-(3,4-dichlorophenyl)-2-(1-piperidyl)pyrimidine-4-carboxamide
6-(4-cyanophenyl)-2-(1-piperidyl)pyrimidine-4-carboxamide
2-(1-piperidyl)-6-[3-(trifluoromethyl)phenyl]-pyrimidine-4-carboxamide
2-(ethyl-(2-methylprop-2-enyl)amino)-6-phenyl-pyrimidine-4-carboxamide
2-[bis(2-ethoxyethyl)amino]-6-phenyl-pyrimidine-4-carboxamide
2-diethylamino-6-[3-(trifluoromethoxy)phenyl]-pyrimidine-4-carboxamide
4-(6-carbamoyl-2-diethylamino-pyrimidin-4-yl)benzoic acid methyl ester
6-benzothiophen-2-yl-2-diethylamino-pyrimidine-4-carboxamide
6-(2-phenoxyphenyl)-2-(1-piperidyl)pyrimidine-4-carboxamide
2-(cyclopropylmethyl-propyl-amino)-6-phenyl-pyrimidine-4-carboxamide
2-azepan-1-yl-6-(4-methoxyphenyl)-pyrimidine-4-carboxamide
2-diethylamino-6-(4-ethylsulfonylphenyl)-pyrimidine-4-carboxamide
6-(4-methyl-2-thienyl)-2-(1-piperidyl)pyrimidine-4-carboxamide
6-(4-chlorophenyl)-2-diethylamino-pyrimidine-4-carboxamide
3ξ-carbamoyl-2-(1-piperidyl)pyrimidin-4-yl]benzoic acid isopropyl ester
2-diethylamino-6-(4-ethoxyphenyl)-pyrimidine-4-carboxamide
2-diethylamino-6-(2,3-dimethylphenyl)-pyrimidine-4-carboxamide
6-(m-tolyl)-2-(1-piperidyl)pyrimidine-4-carboxamide
2-(1-piperidyl)-6-[2-(trifluoromethoxy)phenyl]-pyrimidine-4-carboxamide
2-(ethyl-methyl-amino)-6-phenyl-pyrimidine-4-carboxamide
2-[4-(4-fluorobenzoyl)-1-piperidyl]-6-phenyl-pyrimidine-4-carboxamide
2-dibutylamino-6-phenyl-pyrimidine-4-carboxamide
6-(4-fluoro-3-methyl-phenyl)-2-(1-piperidyl)pyrimidine-4-carboxamide
6-(5-fluoro-2-methoxy-phenyl)-2-(1-piperidyl)pyrimidine-4-carboxamide
6-(3-ethoxyphenyl)-2-(1-piperidyl)pyrimidine-4-carboxamide
6-(3,4-dimethoxyphenyl)-2-(1-piperidyl)pyrimidine-4-carboxamide
2-(methyl-(3-pyridylmethyl)amino)-6-phenyl-pyrimidine-4-carboxamide
2-diethylamino-6-(4-fluorophenyl)-pyrimidine-4-carboxamide
2-diethylamino-6-(4-methyl-2-thienyl)-pyrimidine-4-carboxamide
2-diethylamino-6-(2-ethoxyphenyl)-pyrimidine-4-carboxamide
2-diisopentylamino-6-phenyl-pyrimidine-4-carboxamide
2-(cyanomethyl-methyl-amino)-6-phenyl-pyrimidine-4-carboxamide
2-[4-(2-hydroxyethyl)-1-piperidyl]-6-phenyl-pyrimidine-4-carboxamide
6-(3,5-dichlorophenyl)-2-diethylamino-pyrimidine-4-carboxamide
2-(4-benzyl-1-piperidyl)-6-phenyl-pyrimidine-4-carboxamide
2-(benzyl-butyl-amino)-6-phenyl-pyrimidine-4-carboxamide
2-[4-(4-chlorobenzoyl)-1-piperidyl]-6-phenyl-pyrimidine-4-carboxamide
2-diethylamino-6-(2,4-difluorophenyl)-pyrimidine-4-carboxamide
1-(4-carbamoyl-6-phenyl-pyrimidin-2-yl)piperidine-3-carboxylic acid ethyl ester
2-(6,7-dimethoxy-1,2,3,4-tetrahydroisoquinolin-2-yl)-6-phenyl-pyrimidine-4-carboxamide
6-(2,3-dichlorophenyl)-2-(1-piperidyl)pyrimidine-4-carboxamide
2-[3-(hydroxymethyl)-1-piperidyl]-6-phenyl-pyrimidine-4-carboxamide
2-diethylamino-6-(4-isopropylphenyl)-pyrimidine-4-carboxamide
6-(3-cyanophenyl)-2-(1-piperidyl)pyrimidine-4-carboxamide
6-(5-chloro-2-methoxy-phenyl)-2-diethylamino-pyrimidine-4-carboxamide
2-(4-benzyl-4-hydroxy-1-piperidyl)-6-phenyl-pyrimidine-4-carboxamide
2-(benzyl-methyl-amino)-6-phenyl-pyrimidine-4-carboxamide
2-diethylamino-6-(3-fluorophenyl)-pyrimidine-4-carboxamide
1-(4-carbamoyl-6-phenyl-pyrimidin-2-yl)piperidine-4-carboxylic acid ethyl ester
2-(1H-imidazol-1-yl)-6-phenyl-pyrimidine-4-carboxamide
2-(2,5-dihydro-1H-pyrrol-1-yl)-6-phenyl-pyrimidine-4-carboxamide
2-azocan-1-yl-6-phenyl-pyrimidine-4-carboxamide
6-(2,4-dimethoxyphenyl)-2-(1-piperidyl)pyrimidine-4-carboxamide
2-dimethylamino-6-(4-methoxyphenyl)-pyrimidine-4-carboxamide
2-azepan-1-yl-6-(3-methoxyphenyl)-pyrimidine-4-carboxamide
2-[4-(2-oxo-1,3-dihydrobenzoimidazol-1-yl)-1-piperidyl]-6-phenyl-pyrimidine-4-carboxamide
2-(1-piperidyl)-6-[3-(trifluoromethoxy)phenyl]-pyrimidine-4-carboxamide
2-dimethylamino-6-(2-methoxyphenyl)-pyrimidine-4-carboxamide
2-(ethyl-propyl-amino)-6-phenyl-pyrimidine-4-carboxamide
6-phenyl-2-(1H-pyrazol-1-yl)pyrimidine-4-carboxamide 2-diallylamino-6-phenyl-pyrimidine-4-carboxamide
2-(hexyl-methyl-amino)-6-phenyl-pyrimidine-4-carboxamide
2-diethylamino-6-(2,4-dimethoxyphenyl)-pyrimidine-4-carboxamide
2-(3-methyl-1-piperidyl)-6-phenyl-pyrimidine-4-carboxamide
2-azetidin-1-yl-6-phenyl-pyrimidine-4-carboxamide
2-(3,5-dimethyl-1-piperidyl)-6-phenyl-pyrimidine-4-carboxamide
2-(butyl-(cyanomethyl)amino)-6-phenyl-pyrimidine-4-carboxamide
6-benzothiophen-2-yl-2-(1-piperidyl)pyrimidine-4-carboxamide
2-[(2-hydroxy-2-phenyl-ethyl)-methyl-amino]-6-phenyl-pyrimidine-4-carboxamide
6-(2,4-dichlorophenyl)-2-diethylamino-pyrimidine-4-carboxamide
2-(butyl-(2-hydroxyethyl)amino)-6-phenyl-pyrimidine-4-carboxamide
6-(2-methoxyphenyl)-2-(1,2,3,6-tetrahydropyridin-1-yl)pyrimidine-4-carboxamide
6-(3-methoxyphenyl)-2-(1-piperidyl)pyrimidine-4-carboxamide
2-diethylamino-6-[4-(trifluoromethyl)phenyl]-pyrimidine-4-carboxamide
2-diethylamino-6-[4-(trifluoromethoxy)phenyl]-pyrimidine-4-carboxamide
6-phenyl-2-(1,2,3,6-tetrahydropyridin-1-yl)pyrimidine-4-carboxamide
2-(ethyl-(2-hydroxyethyl)amino)-6-phenyl-pyrimidine-4-carboxamide
2-[2-(1H-indol-3-yl)ethyl-methyl-amino]-6-phenyl-pyrimidine-4-carboxamide
6-(3-acetylaminophenyl)-2-diethylamino-pyrimidine-4-carboxamide
2-[bis(2-hydroxyethyl)amino]-6-(2-methoxyphenyl)-pyrimidine-4-carboxamide
2-diethylamino-6-(2,5-difluorophenyl)-pyrimidine-4-carboxamide
6-(3,4-dimethylphenyl)-2-(1-piperidyl)pyrimidine-4-carboxamide
6-benzo[1,3]dioxol-5-yl-2-(1-piperidyl)pyrimidine-4-carboxamide
2-diethylamino-6-(o-tolyl)pyrimidine-4-carboxamide
2-(cyclopropylmethyl-propyl-amino)-6-(4-methoxyphenyl)-pyrimidine-4-carboxamide
2-(isopentyl-methyl-amino)-6-phenyl-pyrimidine-4-carboxamide
2-(isobutyl-methyl-amino)-6-phenyl-pyrimidine-4-carboxamide
2-diethylamino-6-(2,6-difluorophenyl)-pyrimidine-4-carboxamide
6-(o-tolyl)-2-(1-piperidyl)pyrimidine-4-carboxamide.

23. A pharmaceutical composition comprising a compound as described in claim 1 and a pharmaceutical carrier.

* * * * *